(12) United States Patent
Shabat et al.

(10) Patent No.: US 11,649,475 B2
(45) Date of Patent: May 16, 2023

(54) DIOXETANE COMPOUNDS AND THEIR USE FOR THE DETECTION OF MICROORGANISMS

(71) Applicants: NEMIS Technologies AG, Dübendorf (CH); Ramot at Tel-Aviv University Ltd., Tel-Aviv (IL)

(72) Inventors: Doron Shabat, Tel-Aviv (IL); Michal Eli Roth-Konforti, Tel-Aviv (IL); Nir Hananya, Tel-Aviv (IL); Ori Green, Tel-Aviv (IL); Urs Spitz, St. Gallen (CH); Lukas Wick, Winterthur (CH); Julian Ihssen, St. Gallen (CH); Raffael Vorberg, Rümlang (CH); Riccardo Cribiu, Zürich (CH); Zuzana Babjaková, Koplotov (SK); Chunyan Yao, Radolfzell am Bodensee (DE)

(73) Assignees: Ramot at Tel-Aviv University Ltd., Tel-Aviv (IL); NEMIS Technologies AG, Au (CH)

( * ) Notice: Subject to any disclaimer, the term of this patent is extended or adjusted under 35 U.S.C. 154(b) by 0 days.

(21) Appl. No.: 17/058,623

(22) PCT Filed: May 24, 2019

(86) PCT No.: PCT/EP2019/063418
§ 371 (c)(1),
(2) Date: Nov. 24, 2020

(87) PCT Pub. No.: WO2019/224338
PCT Pub. Date: Nov. 28, 2019

(65) Prior Publication Data
US 2021/0214766 A1    Jul. 15, 2021

(30) Foreign Application Priority Data
May 25, 2018 (EP) .................................... 18174403

(51) Int. Cl.
| C07D 321/00 | (2006.01) |
| C07D 407/04 | (2006.01) |
| C12Q 1/10 | (2006.01) |
| C12Q 1/04 | (2006.01) |
| C12Q 1/14 | (2006.01) |
| C12Q 1/22 | (2006.01) |
| C12Q 1/44 | (2006.01) |
| C12Q 1/54 | (2006.01) |
| G01N 21/76 | (2006.01) |

(52) U.S. Cl.
CPC ............ C12Q 1/10 (2013.01); C07D 321/00 (2013.01); C07D 407/04 (2013.01); C12Q 1/04 (2013.01); C12Q 1/14 (2013.01); C12Q 1/22 (2013.01); C12Q 1/44 (2013.01); C12Q 1/54 (2013.01); G01N 21/76 (2013.01)

(58) Field of Classification Search
CPC ... C07D 321/00; C07D 407/04; C07H 15/203
See application file for complete search history.

(56) References Cited

U.S. PATENT DOCUMENTS

| 5,223,402 A | 6/1993 | Abbas et al. |
| 2007/0225498 A1 | 9/2007 | Giri et al. |

FOREIGN PATENT DOCUMENTS

| WO | WO-2009139811 A2 * | 11/2009 | ............... C12Q 1/66 |
| WO | WO 2017/130191 * | 8/2017 | |

OTHER PUBLICATIONS

International Search Report received in PCT/EP2019/063418, dated Jul. 23, 2019.
Adams et al., "A New Synthesis of Atranol (2,6-Dihydroxy-4-methylbenzaldehyde) and the Corresponding Cinnamic Acid" Journal of the American Chemical Society, 70: 2120-2122 (1948).
Alouane et al., "Self-Immolative Spacers: Kinetic Aspects, Structure—Property Relationships, and Applications" Angewandte Reviews International Edition, 54: 7492-7509 (2015).
Green et al., "Opening a Gateway for Chemiluminescence Cell Imaging: Distinctive Methodology for Design of Bright Chemiluminescent Dioxetane Probes" ACS central science, 3: 349-358 (2017).

(Continued)

*Primary Examiner* — Valerie Rodriguez-Garcia
(74) *Attorney, Agent, or Firm* — Knobbe, Martens, Olson & Bear, LLP

(57) ABSTRACT

Dioxetane compounds represented by Formula I below, and methods of using the dioxetane compounds in the detection of presence or absence, quantification, and identification of microorganisms including bacteria, bacterial fragments (e.g., LPS, endotoxin), viruses, and fungi by means of chemiluminescence.

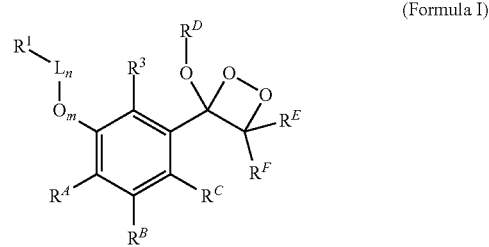

(Formula I)

16 Claims, 5 Drawing Sheets

(56) References Cited

OTHER PUBLICATIONS

Green et al., "Opening a Gateway for Chemiluminescence Cell Imaging: Distinctive Methodology for Design of Bright Chemiluminescent Dioxetane Probes" Supporting Information (2017).
Gonzaga et al., "Perspectives About Self-Immolative Drug Delivery Systems" Journal of Pharmaceutical Sciences, 109:3262-3281 (2020).
Kisin-Finfer et al., "New repertoire of 'donor-two-acceptor' NIR fluorogenic dyes" Bioorganic & Medicinal Chemistry, 21: 3602-3608 (2013).
Indian Office Action issued in Application No. 202027048200, dated Mar. 29, 2022 (6 pages).

* cited by examiner

DIOXETANE COMPOUNDS AND THEIR USE FOR THE DETECTION OF MICROORGANISMS

FIELD OF THE INVENTION

The present invention relates to dioxetane compounds, their use for the detection of presence or absence, quantification and identification of microorganisms including bacteria, bacterial fragments (e.g., LPS, endotoxin), viruses, fungi as well as other pathogens by means of chemiluminescent indication of action of metabolic, reagent or reference enzymes on suitable molecular probes, indication of hydrogen peroxide resulting from enzymatic oxidation of microbial metabolites or nutrients by reagent enzymes or detection of inorganic phosphate playing roles of nutrient, substrate, metabolic product or by-product of action by a reagent enzyme.

BACKGROUND OF THE INVENTION

Bacterial contamination, for example of food, water, blood reserves and the like, poses a major health issue. According to the World Health Organization, waterborne diseases, i.e. diseases caused by pathogenic micro-organisms that are transmitted in water, are linked to significant disease burden worldwide. For example, waterborne diarrheal diseases are responsible for an estimated two million deaths each year, with the majority occurring in children under the age of five.

Thus, methods and means for detecting microorganisms, in particular bacteria, are highly sought after. In this respect, it has been found that genera or species of bacteria can be specifically detected using compounds that generate a detectable signal (e.g., light) upon cleavage by specific enzymes produced by these bacteria. Due to their superior sensitivity and higher signal-to-noise ratio compared to methods based on fluorescence or coloration, detection methods based on chemiluminescence are particularly favored for the detection of microorganisms, in particular bacteria. In particular, it has been shown that chemiluminescence leads to remarkably high signal-to-noise ratios (S/N) that are about 100 to 1000 times higher than those achieved with fluorescence. This, in turn, leads to a remarkably higher sensitivity of chemiluminescence compared to fluorescence.

A well-established system for the detection of microorganisms is the luciferase-luciferin system. D-luciferin is a bioluminogenic compound that is oxidized by luciferase (an oxidoreductase) in the presence of molecular oxygen, ATP and magnesium to a metastable intermediate which in turn decays to emit blue-green light. D-luciferin can be masked with enzyme labile groups, restricting light emission in the presence of luciferase to situations where also the enzyme acting on the enzyme labile group is present. For example, Masuda-Nishimura et al. have reported the detection of coliform bacteria with D-luciferin-6-O-beta-D-galactopyranoside as luminogenic substrate (Masuda-Nishimura et al. (2000), Letters in Applied Microbiology, 30: 130-135).

In recent years, chemical probes have been developed that, unlike most of the currently used chemi- and bioluminescent probes, do not require an oxidation step to trigger its (chemi)luminescence and, thus, can detect a wide range of chemical and biological activities. These chemiluminescent probes contain a stable dioxetan moiety. WO 2017/130191 discloses such dioxetane-based chemiluminescent probes and their use for diagnostics purposes and in vivo imaging.

In addition, Green et al. (Green, O., Eilon, T., Hananya, N., Gutkin, S., Bauer, C R., Shabat, D., *ACS Central Sci.*, 2017, 4, 349-58) disclose chemiluminescent dioxetane probes suitable for use under aqueous conditions, which are masked with enzyme-labile groups and suitable for the detection of enzyme activities.

However, the successful use of chemiluminescent dioxetane probes in the field of microbiology for the detection of specific microorganisms has not been reported so far. In fact, the development of chemiluminescent probes for detecting microorganisms under "real-life" conditions is a particularly difficult challenge due to complex interactions between the probe, the enzyme of the microorganism required for removing enzyme-labile protecting group, and the environment of the chemiluminescent reaction (i.e. the medium comprising the microorganisms). A suitable chemiluminescent probe for the detection of microorganisms must (i) be non-toxic for the microorganism to be detected, (ii) have a high stability in aqueous medium, (iii) be capable of generating a strong chemiluminescent signal in a given medium, and (iv) be able to reach the site of the enzyme that removes the enzyme-labile protecting group (e.g., the periplasmic space, the outside or inside surface of the inner membrane of gram-negative bacteria, the cytosol etc.). Moreover, for obvious reasons, the chemiluminescent probes for the detection of microorganism should be inexpensive and convenient to use.

Due to the above requirements, the question whether a chemiluminescent dioxetane probe is suitable for the "real-life" detection of a microorganism (in aqueous media) cannot be derived or predicted from its chemical structure. Even if a probe shows good performance under "laboratory" conditions, it may be unsuitable for "real-life" applications. Thus, extensive experiments are required for determining whether a specific probe is suitable for the detection of microorganisms under "real-life" conditions.

At present, the luciferase-luciferin system is the only efficient "real-life" (bio)lumiscencent means available for the detection of microorganisms. However, despite being the current industry standard, this system has a number of drawbacks. For example, it is a complex multi-component system (standard composition: 1. pro-luciferin enzyme substrate (e.g., luciferin-beta-D-galactopyranoside), 2. luciferase, 3. bovine serum albumin, 4. ATP, 5. EDTA, 6. D/L-cysteine, 7. MgSO$_4$, 8. sodium pyrophosphate), which is generally more complex than a one-component system. Further, the luciferase-luciferin system requires the use of luciferase, which makes its use quite costly and limits shelf-life due to the notorious instability of commercially available luciferase. Moreover, the sensitivity of the luciferase-luciferin system is limited, thus leaving room for improvement. In general, chemiluminescence is preferred over bioluminescence as it shows a sensitivity that is about 10 to 100 times higher than that achieved with biolumines-cence, in particular the bioluminescent luciferase-luciferin system, and, particularly important, allows for a remarkably simple and straightforward application, in particular compared to very complex bioluminescentluciferase-luciferin system.

OBJECT OF THE INVENTION

In view of the above, it is the object of the present invention to provide probes as well as methods for the detection of presence or absence, quantification and identification of microorganisms including bacteria, bacterial fragments (e.g., LPS, endotoxin), viruses, fungi as well as other pathogens that overcome the disadvantages of commonly applied luciferase-luciferin systems, in particular have a significantly increased sensitivity and are easier to use than a luciferase-luciferin based system.

In particular, chemiluminescent probes (and methods) should be provided that can be used to detect the presence or absence, quantification and identification of microorganisms including bacteria, bacterial fragments (e.g., LPS, endotoxin), viruses, fungi as well as other pathogens by means of chemiluminescent indication, e.g. chemiluminescent indication of action of metabolic, reagent or reference enzymes on suitable molecular probes, indication of hydrogen peroxide resulting from enzymatic oxidation of microbial metabolites or nutrients by reagent enzymes or detection of inorganic phosphate playing roles of nutrient, substrate, metabolic product or by-product of action by a reagent enzyme.

SUMMARY OF THE INVENTION

The above object is achieved by specific dioxetane compounds suitable for use in the detection of presence or absence, quantification and identification of microorganisms including bacteria, bacterial fragments (e.g., LPS, endotoxin), viruses, fungi as well as other pathogens by means of chemiluminescence. As set out in more detail below, it was surprisingly found that the dioxetane compounds according to the present invention are highly efficient probes that enable the detection of presence or absence, quantification and identification of microorganisms including bacteria, bacterial fragments (e.g., LPS, endotoxin), viruses, fungi as well as other pathogens in a more sensitive and simpler way as the commonly applied luciferase-luciferin system.

In a first aspect, the present invention provides a compound of Formula I

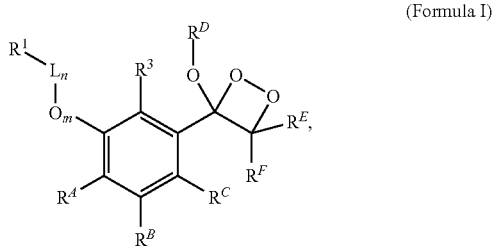

(Formula I)

wherein
$R^1$ is an analyte-responsive group selected from an enzyme-labile group and a boron-containing group having the formula —B(Z)(Z') or —B(Z")$_3^-$Kat$^+$;
Z and Z' are independently selected from $R^4$ and OR$^5$, wherein $R^4$ is selected from the group consisting of —OH, —O$^-$Kat$^+$, optionally substituted C$_1$-C4 alkyl, optionally substituted C2-C4 heteroalkyl, optionally substituted C2-C4 alkenyl, optionally substituted C2-C4 heteroalkenyl, optionally substituted C2-C4 alkynyl, optionally substituted C2-C4 heteroalkynyl, optionally substituted C5-C6 aryl, optionally substituted C5-C6 heteroaryl, optionally substituted C6-C10 aralykl, and optionally substituted C6-C10 heteroaralkyl, and $R^5$ is selected from the group consisting of —H, optionally substituted C1-C4 alkyl, optionally substituted C2-C4 heteroalkyl, optionally substituted C2-C4 alkenyl, optionally substituted C2-C4 heteroalkenyl, optionally substituted C2-C4 alkynyl, optionally substituted C2-C4 heteroalkynyl, optionally substituted C5-C6 aryl, optionally substituted C5-C6 heteroaryl, optionally substituted C6-C10 aralykl, and optionally substituted C6-C10 heteroaralkyl, or wherein two $R^4$, two $R^5$ or one $R^4$ and one $R^5$ together with their intervening atoms form a 5- to 7-membered optionally substituted heterocyclic ring, preferably a saturated optionally substituted heterocyclic ring;
Z" is selected from F, Cl, Br, I, preferably Z" is F;
Kat$^+$ is an organic or anorganic cation, preferably an alkali metal cation;
L is a self-immolative linker group which, upon acting of an analyte on the analyte-responsive group $R^1$, is released from the remainder part of the compound of Formula I, wherein L is optionally functionalized with a peptide, preferably a cell penetrating peptide, an endolysine or a protein;
if $R^1$ is an enzyme-labile group, n is 1 and m is 1 or n is 0 and m is 1, and
if $R^1$ is —B(Z)(Z') or —B(Z")$_3^-$Kat$^+$, n and m are both 0 or both 1;
if $R^1$ is

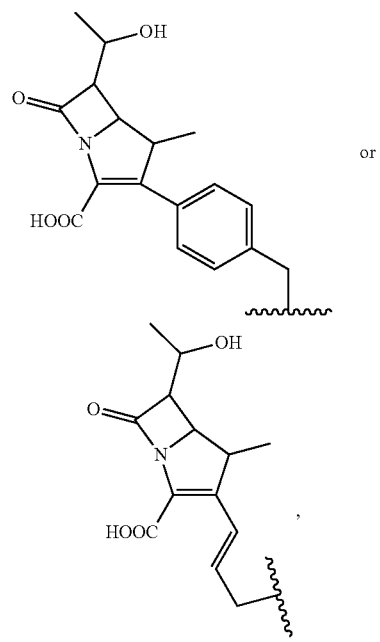

n is 0 and m is 1;
$R^A$ and $R^C$ are independently selected from H, F, Cl, Br, I, CF$_3$ and $R^2$-Q-, preferably from H, Cl and $R^2$-Q, or one of $R^A$ and $R^C$ together with $R^B$ forms an optionally substituted cyclic or heterocyclic structure that extends the pi-system of the central aromatic ring and the other one is H or $R^2$-Q-; provided that $R^A$ and $R^C$ are not both H;
$R^B$ is H or forms together with one of $R^A$ and $R^C$ said optionally substituted cyclic or heterocyclic structure;
Q is group comprising a pi-system that is conjugated with the pi-system of the central aromatic ring of the compound of Formula I;
$R^2$ is a group selected from cyano, nitro, sulfoxide, sulfon, optionally substituted aryl, optionally substituted alkenyl,

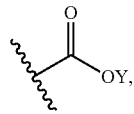

carbonyl, carbonyl having the structure

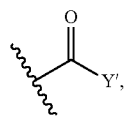

amide, amide having the structure

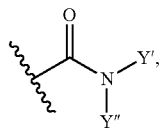

wherein Y is H, an optionally substituted C1-C12 alkyl or an alkali metal ion,
wherein Y' and Y" are independently selected from H, and optionally substituted C1-C12 alkyl or together with the nitrogen atom form an optionally substituted heterocyclic structure, preferably an optionally substituted maleimide group; and
$R^3$ is H, F, Cl, Br, I, $CF_3$ or $R^2$-Q-;
provided that at least one of $R^A$ and $R^C$, preferably $R^A$, is H, F, Cl, Br, I or $CF_3$, preferably Cl, if $R^3$ is $R^2$-Q-;
$R^D$ is selected from a linear or branched C1-C18 alkyl or C3-C7 cycloalkyl;
$R^E$ and $R^F$ are independently selected from a branched C3-C18 alkyl or C3-C7 cycloalkyl, or $R^E$ and $R^F$ together with the carbon atom to which they are attached form an optionally substituted fused, spiro or polycyclic ring.

In a second aspect, the present invention is directed to the use of a compound of Formula I for the detection of a target analyte (e.g., hydrogen peroxide), a target microorganism or a target metabolite, preferably a microorganism, e.g. a bacterium and to a method for the detection of a target analyte, a target microorganism or a target metabolite.

In a third aspect, the present invention is directed to the use of a compound of Formula I for the detection of growth substrates, nutrients, and/or metabolites by enzymatic oxidation of said growth substrates, nutrients, and metabolites and to a method for the detection of growth substrates, nutrients, and/or metabolites by enzymatic oxidation of said growth substrates, nutrients, and metabolites.

In a fourth aspect, the present invention is directed to the use of a compound of Formula I for the detection of bacterial endotoxins using limulus factor C and to a method for the detection of bacterial endotoxins using limulus factor C.

In a fifth aspect, the present invention is directed to the use of a compound of Formula I for testing of pasteurization of dairy products and to a method of testing of pasteurization of dairy products.

In a sixth aspect, the present invention is directed to the use of a compound of Formula I for testing of antibiotic resistance in microorganisms and to a method for testing of antibiotic resistance in microorganisms.

In a seventh aspect, the present invention is directed to the use of a compound of Formula I for the detection of inorganic phosphate and to a method for the detection of inorganic phosphate.

In an eights aspect, the present invention is directed to the use of a compound of Formula I for monitoring of a sterilization process, in particular through detection of alpha-D-glucosidase activity of the indicator microorganism *Geobacillus stearothermophilus*, and to a method for monitoring of a sterilization process, in particular by detecting alpha-D-glucosidase activity of the indicator microorganism *Geobacillus stearothermophilus*.

In a ninth aspect, the present invention is directed to the use of a compound of Formula I for endpoint and online detection of antibiotic resistance of bacteria and for antibiotic susceptibility testing as well as to a method for endpoint and online detection of antibiotic resistance of bacteria and for antibiotic susceptibility testing.

Preferred embodiments of the present invention are set forth in the appended claims. Further embodiments and other objects, advantages and features of the present invention will become apparent from the following detailed description of the invention and the examples.

DETAILED DESCRIPTION OF THE PREFERRED EMBODIMENT

Figure 1:
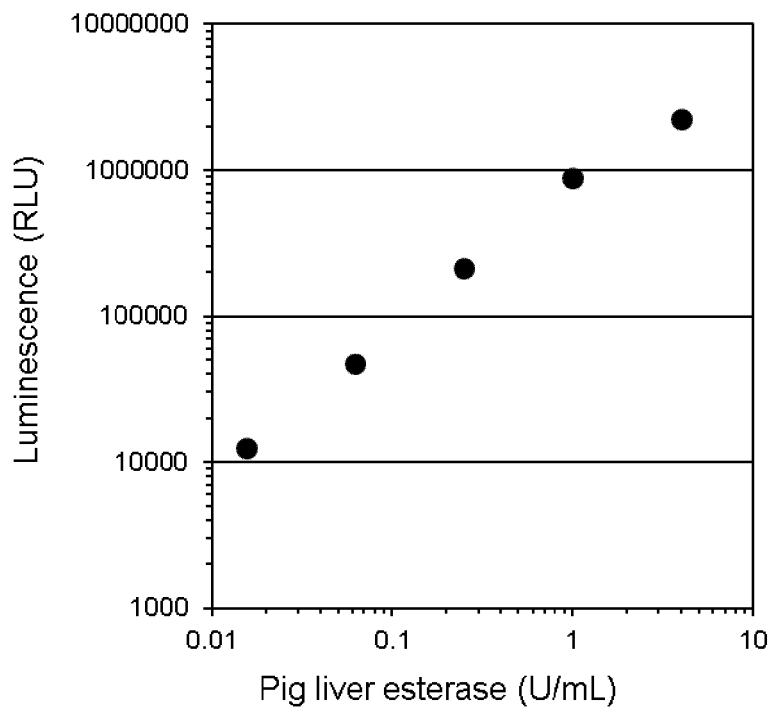
FIG. 1 shows the luminescence of Compound IIa (maximal RLU values within the 20 min measurement period) in the presence of various concentrations of pig liver esterase.

The present invention is based on the surprising finding that, although a luciferase-luciferin-based system shows a number of drawbacks (as set out above), such a system is currently the only "real-life" bio- or chemiluminescent system available for the detection of microorganisms. In this respect, the inventors of the present invention have surprisingly found that dioxetane compounds of Formula I are highly efficient probes for detecting microorganisms. In particular, it has been found that dioxetane compounds of Formula I are chemiluminescent even in aqueous media and show a remarkably high sensitivity when used for the detection of microorganisms, which is significantly higher than that of a commonly applied luciferase-luciferin system. Moreover, important properties of the inventive compounds, e.g. the membrane-permeability and/or solubility, can be modified by varying the substituent $R^2$, if present. Furthermore, it has been found that the dioxetane compounds of Formula I are stable in aqueous media and in particular stable in microbial growth media. In particular, it has been found that dioxetane-based compounds of Formula I allow for an easy, straight-forward, cheap and reliable detection of microorganisms. The compounds can simply be added to the medium comprising the microorganism as they are without the need for any further compounds. In particular, it has been found that dioxetane compounds of Formula I are superior to the commonly-used luciferase-luciferin-based system.

In a first aspect, the present invention relates to a compound of Formula I

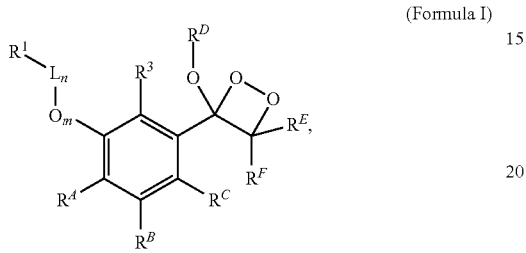
(Formula I)

wherein

R¹ is an analyte-responsive group selected from an enzyme-labile group and a boron-containing group having the formula —B(Z)(Z') or —B(Z")₃⁻Kat⁺;

Z and Z' are independently selected from R⁴ and OR⁵, wherein R⁴ is selected from the group consisting of —OH, —O⁻Kat⁺, optionally substituted C1-C4 alkyl, optionally substituted C2-C4 heteroalkyl, optionally substituted C2-C4 alkenyl, optionally substituted C2-C4 heteroalkenyl, optionally substituted C2-C4 alkynyl, optionally substituted C2-C4 heteroalkynyl, optionally substituted C5-C6 aryl, optionally substituted C5-C6 heteroaryl, optionally substituted C6-C10 aralykl, and optionally substituted C6-C10 heteroaralkyl, and R⁵ is selected from the group consisting of —H, optionally substituted C1-C4 alkyl, optionally substituted C2-C4 heteroalkyl, optionally substituted C2-C4 alkenyl, optionally substituted C2-C4 heteroalkenyl, optionally substituted C2-C4 alkynyl, optionally substituted C2-C4 heteroalkynyl, optionally substituted C5-C6 aryl, optionally substituted C5-C6 heteroaryl, optionally substituted C6-C10 aralykl, and optionally substituted C6-C10 heteroaralkyl, or wherein two R⁴, two R⁵ or one R⁴ and one R⁵ together with their intervening atoms form a 5- to 7-membered optionally substituted heterocyclic ring, preferably a saturated optionally substituted heterocyclic ring;

Z" is selected from F, Cl, Br, I, preferably Z" is F;

Kat⁺ is an organic or anorganic cation, preferably an alkali metal cation;

L is a self-immolative linker group which, upon acting of an analyte on the analyte-responsive group R¹, is released from the remainder part of the compound of Formula I, wherein L is optionally functionalized with a peptide, preferably a cell penetrating peptide, an endolysine or a protein;

if R¹ is an enzyme-labile group, n is 1 and m is 1 or n is 0 and m is 1, and if R¹ is —B(Z)(Z') or —B(Z")₃⁻Kat⁺, n and m are both 0 or both 1;

if R¹ is

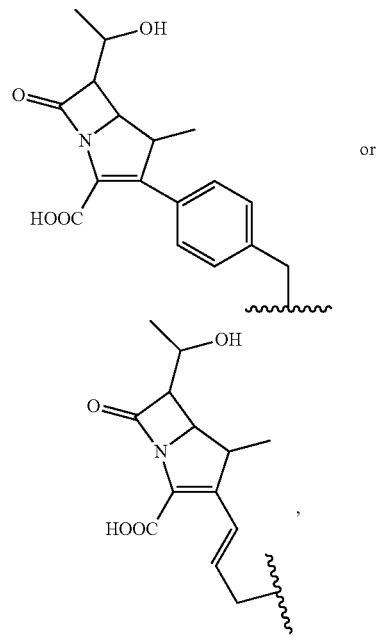

n is 0 and m is 1;

R⁴ and R^C are independently selected from H, F, Cl, Br, CF₃ and R²-Q-, preferably from H, Cl and R²-Q-, or one of R^A and R^C together with R^B forms an optionally substituted cyclic or heterocyclic structure that extends the pi-system of the central aromatic ring and the other one is H or R²-Q-; provided that R^A and R^C are not both H;

R^B is H or forms together with one of R^A and R^C said optionally substituted cyclic or heterocyclic structure;

Q is group comprising a pi-system that is conjugated with the pi-system of the central aromatic ring of the compound of Formula I;

R² is a group selected from cyano, nitro, sulfoxide, sulfon, optionally substituted aryl, optionally substituted alkenyl,

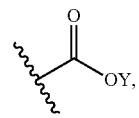

carbonyl, carbonyl having the structure

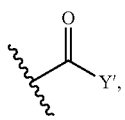

amide, amide having the structure

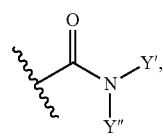

wherein Y is H, an optionally substituted C1-C12 alkyl or an alkali metal ion, wherein Y' and Y" are independently selected from H, and optionally substituted C1-C12 alkyl or together with the nitrogen atom form an optionally substituted heterocyclic structure, preferably an optionally substituted maleimide group; and $R^3$ is H, F, Cl, Br, I, $CF_3$ or $R^2$-Q-;

provided that at least one of $R^A$ and $R^C$, preferably $R^A$, is H, F, Cl, Br, I or $CF_3$, preferably Cl, if $R^3$ is $R^2$-Q-;

$R^D$ is selected from a linear or branched C1-C18 alkyl or C3-C7 cycloalkyl;

$R^E$ and $R^F$ are independently selected from a branched C3-C18 alkyl or C3-C7 cycloalkyl, or $R^E$ and $R^F$ together with the carbon atom to which they are attached form an optionally substituted fused, spiro or polycyclic ring.

The term "alkyl", as used herein, refers to a linear or branched hydrocarbon radical and includes, for example, methyl, ethyl, n-propyl, isopropyl, n-butyl, sec-butyl, tert-butyl, n-pentyl and so on. Thus, e.g., the term "$C_1$-$C_{12}$ alkyl" (or "C1-C12 alkyl"), as used herein, refers to an "alkyl" having 1 to 12 carbon atoms.

The term "alkenyl", as used herein, refers to a linear or branched hydrocarbon radical having one or more carbon-carbon double bonds.

The term "alkynyl", as used herein, refers to a linear or branched hydrocarbon radical having one or more carbon-carbon triple bonds.

The terms "heteroalkyl," "heteroalkenyl," and "heteroalkynyl", as used herein, refer to the corresponding hydrocarbyl (alkyl, alkenyl, and alkynyl) group, which contain one or more O, S or N heteroatoms or combinations thereof within the backbone residue; thus, at least one carbon atom of a corresponding alkyl, alkenyl, or alkynyl group is replaced by one of the specified heteroatoms to form a heteroalkyl, heteroalkenyl, or heteroalkynyl group.

The term "aryl", as used herein, refers to an aromatic carbocyclic group consisting of a single ring or condensed multiple rings such as, but not limited to, phenyl, naphthyl, phenanthryl, and biphenyl. The "aryl" may be substituted or unsubstituted.

The term "heteroaryl", as used herein, refers to an aromatic group containing at least one heteroatom (i.e. an atom different from carbon or hydrogen, e.g. N, S, O, P, Se, Te, preferably N, S, O, P) as a ring member.

Suitable substituents on an "optionally substituted" or "substituted" group are independently halogen; —$(CH_2)_{0-4}$R°; —$(CH_2)_{0-4}$OR°; —O$(CH_2)_{0-4}$R°, —O—$(CH_2)_{0-4}$C(O)OR°; —$(CH_2)_{0-4}$CH(OR°)$_2$; —$(CH_2)_{0-4}$SR°; —$(CH_2)_{0-4}$Ph, which may be substituted with R°; —$(CH_2)_{0-4}$O$(CH_2)_{0-1}$Ph which may be substituted with R°; —CH=CHPh, which may be substituted with R°; —$(CH_2)_{0-4}$O$(CH_2)_{0-1}$-pyridyl which may be substituted with R°; —$NO_2$; —CN; —$N_3$; —$(CH_2)_{0-4}$N(R°)$_2$; —$(CH_2)_{0-4}$N(R°)C(O)R°; —N(R°)C(S)R°; —$(CH_2)_{0-4}$N(R°)C(O)NR°$_2$; —N(R°)C(S)NR°$_2$; —$(CH_2)_{0-4}$N(R°)C(O)OR°; —N(R°)N(R°)C(O)R°; —N(R°)N(R°)C(O)NR°$_2$; —N(R°)N(R°)C(O)OR°; —$(CH_2)_{0-4}$C(O)R°; —C(S)R°; —$(CH_2)_{0-4}$C(O)OR°; —$(CH_2)_{0-4}$C(O)SR°; —$(CH_2)_{0-4}$C(O)OSiR°$_3$; —$(CH_2)_{0-4}$OC(O)R°; —OC(O)$(CH_2)_{0-4}$SR—; —$(CH_2)_{0-4}$SC(O)R°; —$(CH_2)_{0-4}$C(O)NR°$_2$; —C(S)NR°$_2$; —C(S)SR°; —SC(S)SR°, —$(CH_2)_{0-4}$OC(O)NR°$_2$; —C(O)N(OR°)R°; —C(O)C(O)R°; —C(O)$CH_2$C(O)R°; —C(NOR°)R°; —$(CH_2)_{0-4}$SSR°; —$(CH_2)_{0-4}$S(O)$_2$R°; —$(CH_2)_{0-4}$S(O)$_2$OR°; —$(CH_2)_{0-4}$OS(O)$_2$R°; —S(O)$_2$NR°$_2$; —$(CH_2)_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —($C_{1-4}$ straight or branched alkylene)O—N(R°)$_2$; or —($C_{1-4}$ straight or branched alkylene)C(O)O—N(R°)$_2$, wherein each R° is independently hydrogen, $C_{1-6}$ alkyl, —$CH_2$Ph, —O$(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur; or =O, =S, =NNR°$_2$, =NNHC(O)R°, =NNHC(O)OR°, =NNHS(O)$_2$R°, =NR°, =NOR°, —O(C(R°$_2$))$_{2-3}$O—, or —S(C(R°$_2$))$_{2-3}$S—, wherein each independent occurrence of R° is selected from hydrogen, $C_{1-6}$ alkyl, or an unsubstituted 5-6-membered saturated, partially unsaturated, or aryl ring having 0-4 heteroatoms independently selected from nitrogen, oxygen, or sulfur.

When n or m is 0, this means that the respective substituent is absent. Thus, when m is 0, linker L is directly bound to the central aromatic ring (i.e. the aromatic ring shown in Formula I). Otherwise, when n is 0, $R^1$ is bound to the oxygen atom (if m is 1) or to the central aromatic ring (if m is 0).

The symbol " ~~~~ " terminating a bond of a chemical moiety, as used herein, indicates the connection to another moiety. For example, a compound of Formula I, wherein n is 0, m is 1 and $R^1$ is

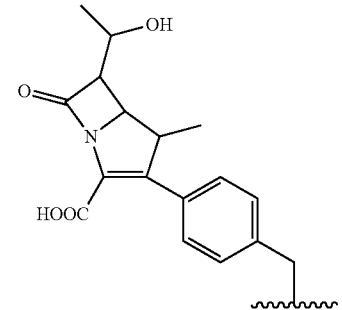 [SMILES: *Cc1ccc(C2=C(C(=O)O)N3C(=O)C(C(C)O)C3C2C)cc1]

represents a compound of the following structure:

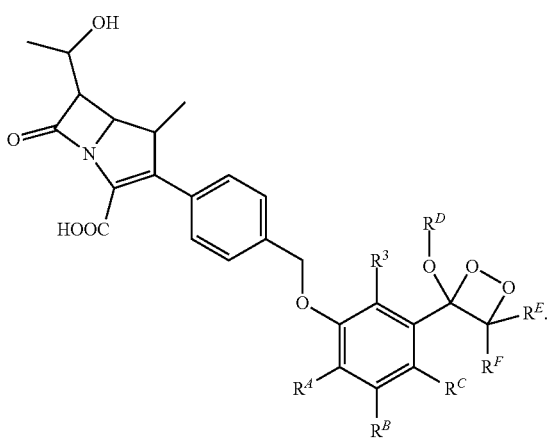

The term "dioxetane compound", as used herein, refers to a compound comprising the moiety

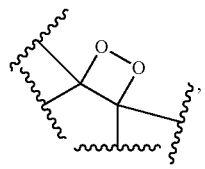 [SMILES: *C1(*)OOC1(*)*]

more specifically to a compound of Formula I.

The term "analyte-responsive group", as used herein, refers to a group that can be removed (at least in part) or modified by means of a specific analyte, wherein removal or modification is such that luminescence is triggered. Preferably, when n is 1 (i.e., linker group L is present), the action of an analyte on the analyte-responsive group transforms the analyte-responsive group $R^1$ into a —OH or —NH$_2$ moiety (when L comprises group X, the moiety "X—R$^1$" is preferably transformed to a —OH or —NH$_2$ moiety) such that elimination of the linker group "L", e.g. 1,6-elimination, is triggered. When n is 0 (i.e., linker group L is not present), it is preferred that the action of an analyte on the analyte-responsive group $R^1$ transforms the analyte-responsive group $R^1$ to —OH or another acidic group (when m is 1, the moiety "O—R" is transformed to —OH or another acidic group).

The term "enzyme-labile group", as used herein, refers to a group that can be removed (at least in part) or modified by means of a specific enzyme.

The term target analyte, a target microorganism or a target metabolite, as used herein, refers to an analyte, microorganism or metabolite that is to be detected by means of a compound Formula I.

Preferably, $R^A$ and $R^C$ are independently selected from H and $R^2$-Q-, or one of $R^A$ and $R^C$ together with $R^B$ forms an optionally substituted cyclic or heterocyclic structure that extends the pi-system of the central aromatic ring and the other one is H or $R^2$-Q-, and $R^3$ is H, F, Cl, Br, I.

According to a preferred embodiment, one of $R^A$ and $R^C$ together with $R^B$ forms an optionally substituted cyclic or heterocyclic structure that extends the pi-system of the central aromatic ring and the other one is H or $R^2$-Q-;

According to another preferred embodiment, one of $R^A$ and $R^C$ is $R^2$-Q- and the other one is H. According to a particularly preferred embodiment, $R^A$ is $R^2$-Q- and $R^C$ is H. According to another preferred embodiment $R^C$ is $R^2$-Q- and $R^A$ is H.

Q is a group comprising a pi-system that is conjugated with the pi-system of the central aromatic ring of the compound of Formula. It has been shown that, due to said conjugation, group Q (potentially together with group $R^2$ attached thereto) can be used to tailor design the luminescence of the compound of Formula I. For example, it has been shown that group Q may influence the emission wavelength, the kinetics of emission (flash emission vs. glow emission) and the quantum yield.

According to a preferred embodiment, Q is selected from the group consisting of —(H$_2$C=CH$_2$)$_q$—,

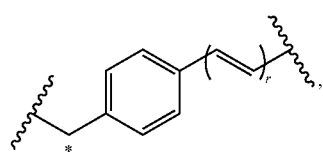

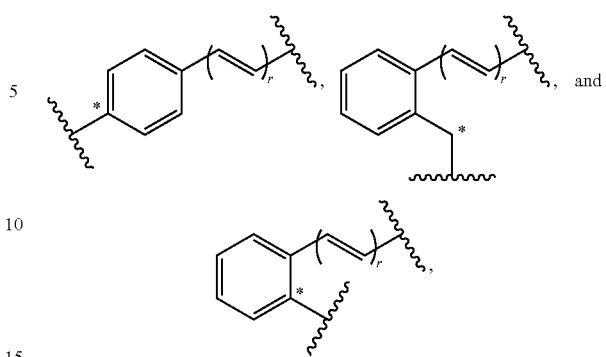

wherein the asterisk (*) indicates the atom that is connected to $R^2$. q and r are selected from the group consisting of 1, 2, 3, 4, 5, and 6, preferably q and r are 1. According to a particularly preferred embodiment, Q is —(H$_2$C=CH$_2$)$_q$—, more preferably Q is —H$_2$C=CH$_2$—.

According to another preferred embodiment, one of $R^A$ and $R^C$ together with $R^B$ forms an optionally substituted cyclic or heterocyclic structure that extends the pi-system of the central aromatic ring. In this case, the other one of $R^A$ and $R^C$ is $R^2$-Q or H, preferably H. "Extends the pi-system of the central aromatic ring" means that the optionally substituted cyclic or heterocyclic structure comprises a pi-system that conjugates with the pi-system of the central aromatic ring.

Preferably, the optionally substituted cyclic or heterocyclic structure formed by one of $R^A$ and $R^C$ together with $R^B$ is a 6-membered ring. More preferably, said 6-membered ring is selected from the group consisting of

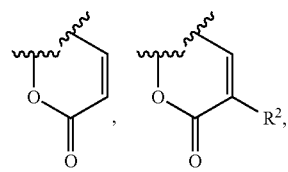

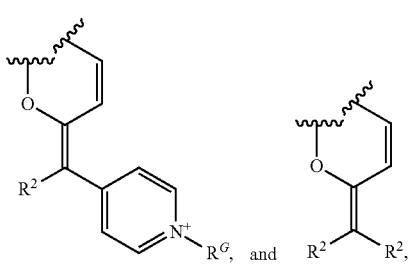

wherein $R^G$ is selected from a substituted or unsubstituted C1-C12 alkyl and wherein $R^2$ is as defined above and below. It is understood that the above moieties may be connected to $R^A$ and $R^B$ or $R^C$ and $R^B$ in any way. This means that a compound of Formula I, wherein $R^A$ together with $R^B$ forms the moiety

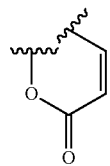

includes both of the following options:

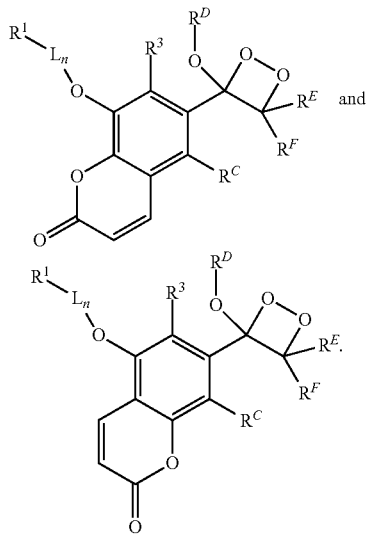

It is particularly preferred a the optionally substituted cyclic or heterocyclic structure formed by one of $R^A$ and $R^C$ together with $R^B$ is unsubstituted

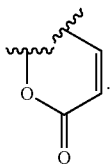 [SMILES: */C=C\C(=O)O*]

Surprisingly, it has been found that a compound of Formula I comprising said cyclic structure

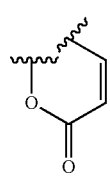

formed by one of $R^A$ and $R^C$ together with $R^B$, in particular $R^C$ together $R^B$, upon removal (at least in part) or modification of the $R^1$ group by means of an interaction with an analyte shows a very long-lasting luminescence (glow emission). In contrast, a compound of Formula I, wherein one of $R^A$ and $R^C$ is $R^2$-Q-, in particular MeOOC—CH=CH—, shows a short but intense emission (flash emission) (see Example 13). Further, it has surprisingly been found that a compound of Formula I comprising the cyclic structure

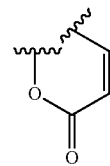 [SMILES: */C=C\C(=O)O*]

formed by one of $R^A$ and $R^C$ together with $R^B$, in particular $R^C$ together $R^B$, shows an extraordinary high luminescence quantum yield of more than 50%, which has not been achieved so far.

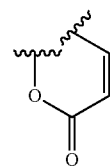 [SMILES: */C=C\C(=O)O*]

Thus, a compound of Formula I comprising the cyclic structure 0 formed by one of $R^A$ and $R^C$ together with $R^B$, in particular $R^C$ together $R^B$, shows an about 20 times higher luminescence intensity than a compound of Formula I, wherein one of $R^A$ and $R^C$ is $R^2$-Q-, in particular MeOOC—CH=CH— (see Example 13).

It has further been found that the luminescent properties can further be fine-tuned by means of substituent $R^3$ (see Example 13). According to a preferred embodiment, $R^E$ and $R^F$ together with the carbon atom to which they are attached form an optionally substituted fused, spiro or bridged cyclic or polycyclic ring. The primary function of groups $R^E$ and $R^F$ is to sterically protect the dioxetane moiety of the compound of Formula I.

Preferably, said optionally substituted fused, spiro or bridged cyclic or polycyclic ring is selected from an optionally substituted propellane; an optionally substituted bicyclus defined by the formula [A.B.1]pentane, [A.B.1]hexane, [A.B.1]heptane, [A.B.1]octane, [A.B.1]nonane, [A.B.1]decane, [A.B.1]undecane, [A.B.1]dodecane, wherein A and B are independently selected from 1, 2, 3, 4, and 5; or optionally substituted adamantine. More preferably, $R^E$ and $R^F$ together with the carbon atom to which they are attached preferably form an optionally substituted

moiety, an optionally substituted

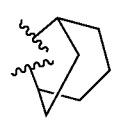

moiety, or an optionally substituted

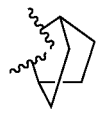

moiety. Even more preferably, $R^E$ and $R^F$ together with the carbon atom to which they are attached form an optionally substituted

moiety. Particularly preferably, $R^E$ and $R^F$ together with the carbon atom to which they are attached form an unsubstituted

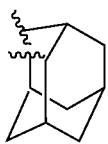

moiety.

According to a preferred embodiment, $R^D$ is methyl, ethyl, or isopropyl. Preferably, $R^D$ is methyl.

Particularly preferred compounds are selected from the group consisting of

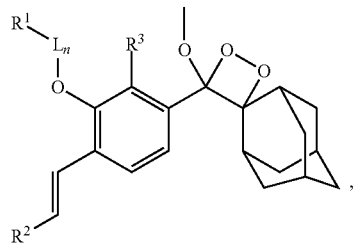

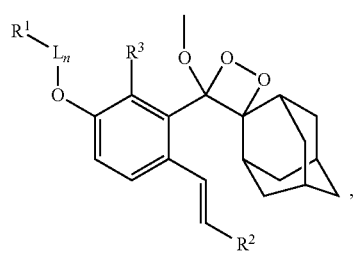

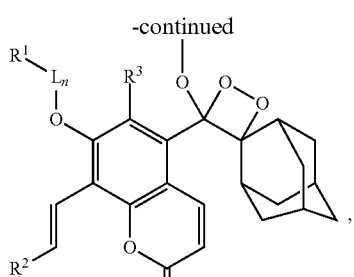

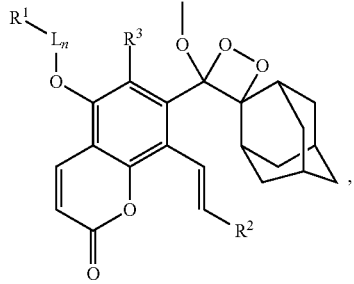

-continued

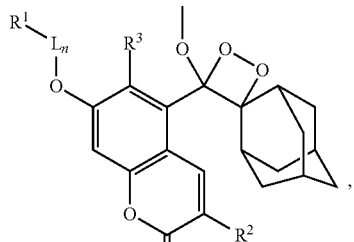

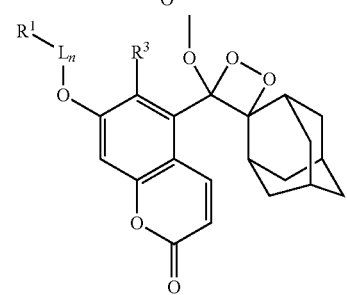

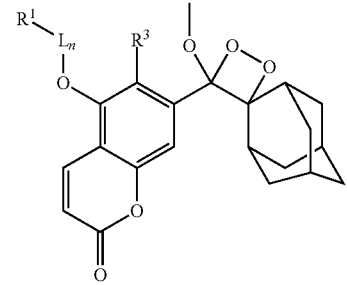

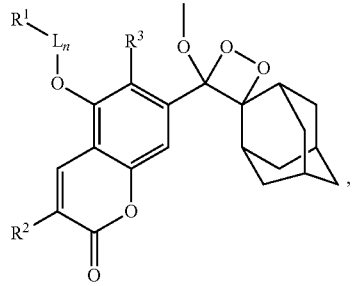

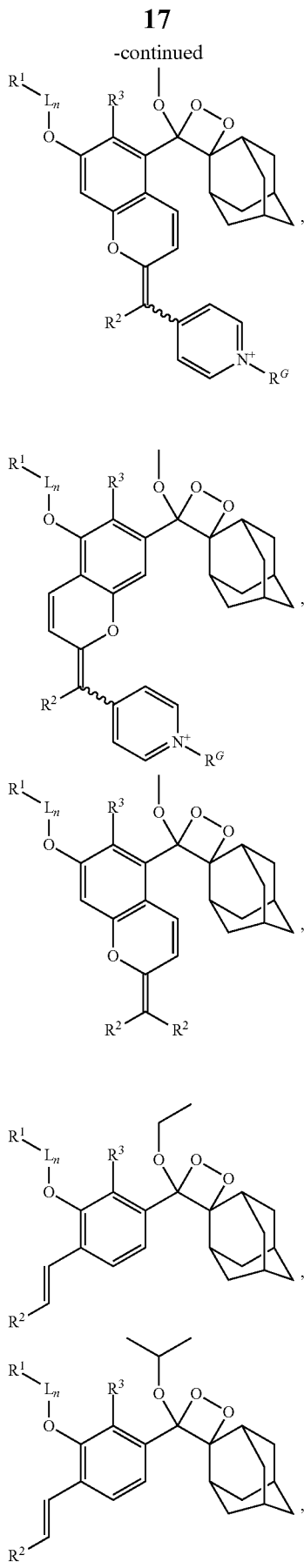

According to a preferred embodiment, the compound of Formula I is represented by Formula I'

(Formula I')

According to a preferred embodiment, $R^1$ is an enzyme-labile group. Preferably, $R^1$ is selected from the group consisting of acetyl, butyryl, octanoyl, nonanoyl, myo-inositol phosphoryl, phosphoryl, an amino acidyl group, L-pyroglutamic acidyl, a di-peptidyl group, a tri-peptidyl group, beta-D-galactopyranosidyl, alpha-D-galactopyranosidyl, alpha-D-glucopyranosidyl, beta-D-glucopyranosidyl, beta-D-glucuronyl, beta-D-glucuronyl sodium salt, n-acetyl-beta-D-galactosaminidyl, N-acetylneuraminidyl, cellobiosidyl, alpha-D-ribofuranosidyl, beta-D-ribofuranosidyl, choline phosphoryl, —$NO_2$, stearoyl, palmitoyl, oleoyl, linoleyl, Tos-L-alanyl, alpha-mannosyl, beta-mannosyl, alpha-fucosyl, beta-fucosyl, alpha-ideuronosyl, beta-ideuronosyl, alpha-(oligo)maltoesyl, a group having the formula —B(Z)(Z'), wherein Z and Z' are as defined above, —B(Z")$_3$⁻Kat⁺, an oxalylester, SucOMe-Arg-Pro-Tyrosinyl, a beta-lactamase-labile group, preferably a beta-lactam antibiotic, more preferably a penicillin, a cephalosporin of generation 1 to 5, a cephamycin, or a carbapenem, Ac-QLQ-, Ac-FQLQ-, Ac-EFQLQ-, Ac-DEFQLQ-.

Preferred cephalosporins of generation 1 to 5 are selected from cefacteril, cefradin, cefroxadin, cefaloglycin, cefaclor, cefalexin, cefadroxil, cefatrizin, cefazedon, cefapirin, ceftezol, cefazolin, cefezaflur, cefalotin, cefaloridin, cefalonium, wherein the carbon atom next to the carbon atom to which the carboxylic acid group is attached is used to bind the cephalosporin the compound of Formula I,

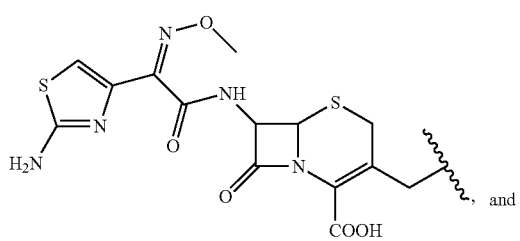
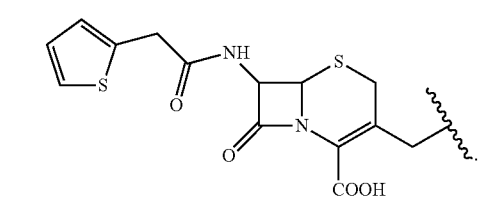
Preferred carbapenems are selected from
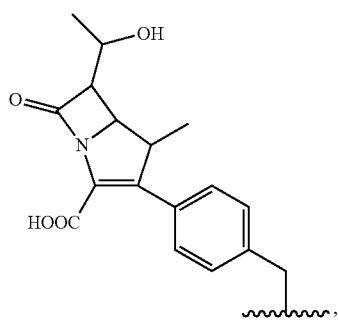
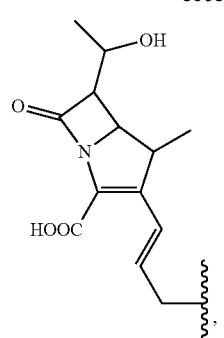
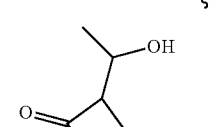
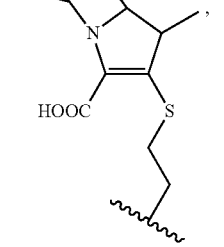
preferably
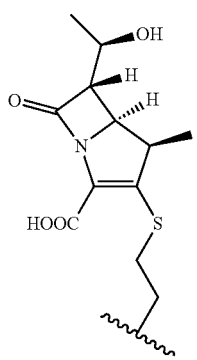 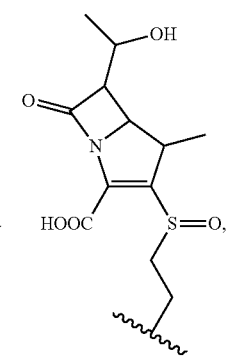
preferably
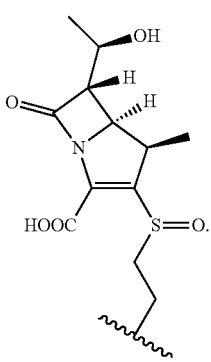 [SMILES: *CCS(=O)C1=C(C(=O)O)N2C(=O)[C@H]([C@@H](C)O)[C@H]2[C@H]1C]
A particularly preferred carbapenem is the moiety
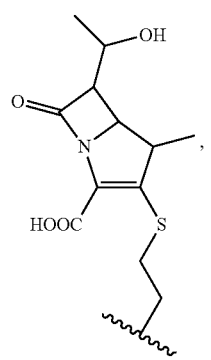 [SMILES: *CCSC1=C(C(=O)O)N2C(=O)C(C(C)O)C2C1C]

preferably

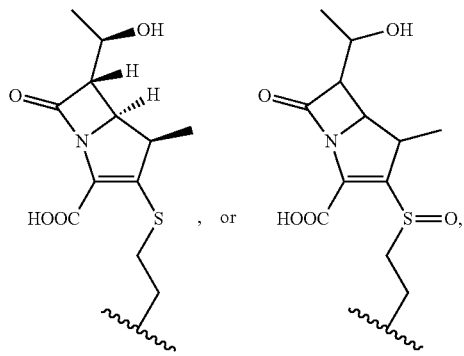 [SMILES: *CCSC1=C(C(=O)O)N2C(=O)[C@H]([C@@H](C)O)[C@H]2[C@H]1C ; *CCS(=O)C1=C(C(=O)O)N2C(=O)C(C(C)O)C2C1C]

preferably

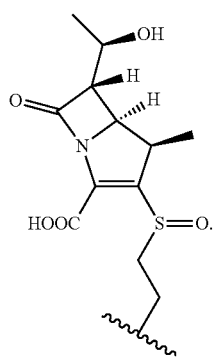 [SMILES: *CCS(=O)C1=C(C(=O)O)N2C(=O)[C@H]([C@@H](C)O)[C@H]2[C@H]1C]

It has surprisingly been found that these moieties are more stable than other carbapenem moieties described herein and show a significantly lower background, which is believed to be due to the beta lactam stabilizing sulfide or sulfoxide group.

Particularly preferred beta-lactamase-labile groups are selected from the group consisting of

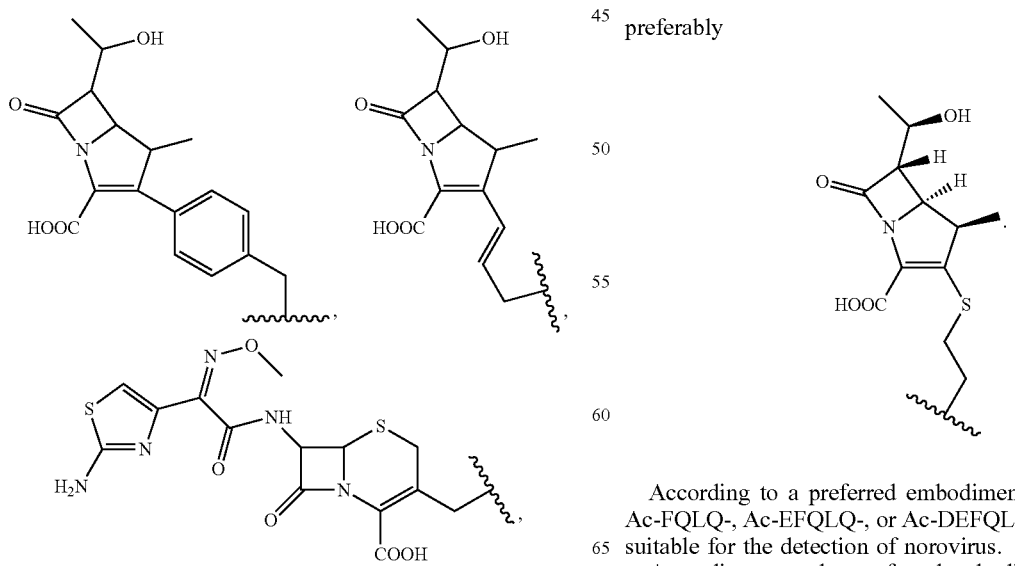

preferably

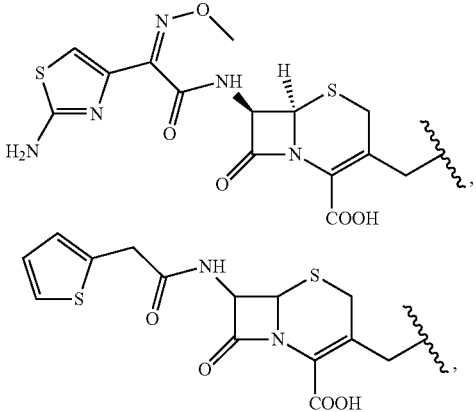

preferably

According to a preferred embodiment, $R^1$ is Ac-QLQ-, Ac-FQLQ-, Ac-EFQLQ-, or Ac-DEFQL-. These groups are suitable for the detection of norovirus.

According to another preferred embodiment, $R^1$ is a group having the formula —B(Z)(Z') or —BF$_3^-$Kat$^+$, wherein preferably at least one of Z and Z' is OR$^5$, more preferably both of Z and Z' are OR$^5$, or wherein the group having the formula —B(Z)(Z') is preferably selected from the group consisting of —B(OH)$_2$, —BF$_3^-$Kat$^+$,

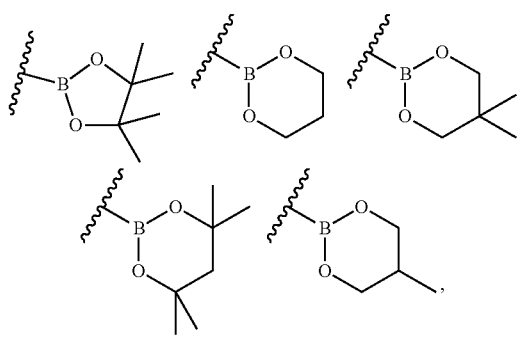

and is more preferably

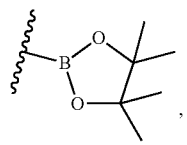 [SMILES: *B1OC(C)(C)C(C)(C)O1]

—B(OH)$_2$, or —BF$_3^-$Kat$^+$.

The linker group "L" has several advantages that were not known before the present invention was made. One the one hand, it leads to a better hydrolysis-stability of the compound of Formula I, which is particularly important, because the compound of Formula I is preferably used in aqueous media. On the other hand, it leads to a good availability of group R$^1$ by sterically distancing the group R$^1$ from the remainder part of the compound of Formula I. Better (hydrolysis) stability leads to a less unspecific hydrolysis, thereby to a lower background, which leads to a better signal to noise ratio and, consequently, to a higher sensitivity. Increasing the availability of group R$^1$ leads to a better binding to a target analyte, in particular an enzyme, and thereby to a higher turnover, which leads to an increased signal to noise ratio and, consequently, to a higher sensitivity. Furthermore, the improved bio-availability improves the detection of membrane-bound enzymes.

Preferably, L is a self-immolative group that, upon acting of an analyte on the analyte-responsive group R$^1$ (thereby leading to an at least partial removal or modification of the analyte-responsive group R$^1$), is released from the remainder part of the compound of Formula I. L is the preferred moiety for attachment of a peptide (preferably a cell penetrating peptide), an endolysine or a protein to the compound of Formula I. In particular, it has been found that functionalization of L with these groups does not quench luminescence of a compound of Formula I. Without wishing to be bound by any theory, it is believed that the reason for this surprising phenomenon is the fact that the linker L is generally cleaved off from the remainder part of the compound of Formula I before luminescence is triggered. Thus, in one embodiment, L is functionalized with a peptide (preferably a cell penetrating peptide), an endolysine or a protein. In another embodiment, L is not functionalized with a peptide (preferably a cell penetrating peptide), an endolysine or a protein.

Preferably, L is selected from the group consisting of

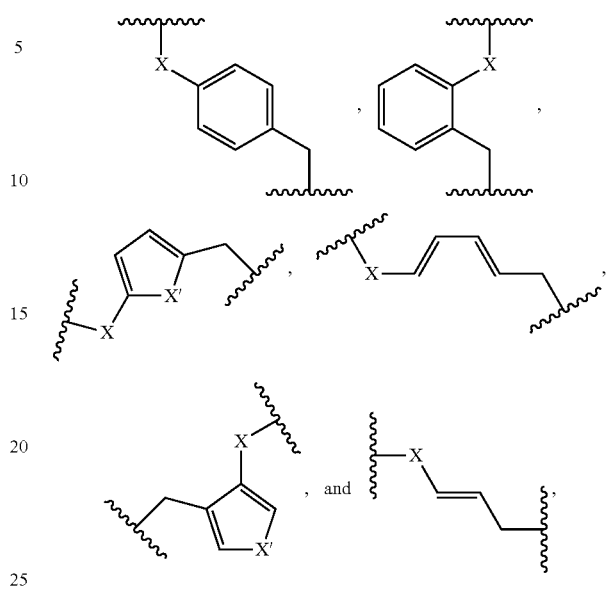

wherein
each of these linkers may be functionalized with a peptide, preferably a cell penetrating peptide, an endolysine or a protein and wherein
X is —O—, —N$^+$(R$^G$)$_2$—, preferably —N$^+$(CH$_3$)$_2$—, or —NH—, wherein X is absent if R$^1$ is —B(Z)(Z') or —NO$_2$, X' is selected from S, O, NH, and NR$^G$; and X is connected to R$^1$.

Preferably, L is

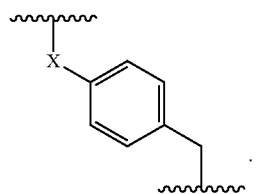

Preferably, X is —N$^+$(CH$_3$)$_2$— when R$^1$ is

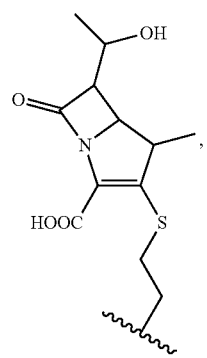 [SMILES: *CCSC1=C(C(=O)O)N2C(=O)C(C(C)O)C2C1C]

preferably

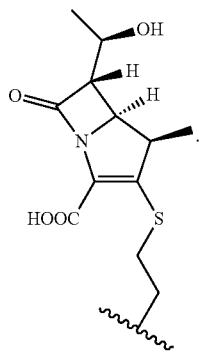 [SMILES: *CCSC1=C(C(=O)O)N2C(=O)[C@H]([C@@H](C)O)[C@H]2[C@H]1C]

According to a preferred embodiment, X is —O—. According to another preferred embodiment, X is —NH—.

According to a preferred embodiment, n is 1 and m is 1. According to another preferred embodiment, n is 0 and m is 1.

According to a preferred embodiment, $R^2$ is a water-solubilizing group.

Preferably, $R^2$ is selected from the group consisting of cyano and

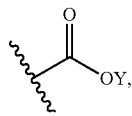

wherein Y is H or an optionally substituted C1-C12 alkyl or an alkali metal ion, wherein the alkali metal ion is preferably sodium or potassium and the optionally substituted $C_1$-$C_{12}$ alkyl is preferably methyl, ethyl propyl, isopropyl, butyl, isobutyl, or tert-butyl.

Preferably, $R^2$ is

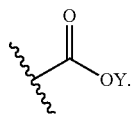

In embodiments where $R^2$ is

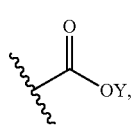

Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl propyl, isopropyl, butyl, isobutyl, or tert-butyl. Preferably, Y is —H, or an optionally substituted $C_1$-$C_{12}$ alkyl, wherein the $C_1$-$C_{12}$ alkyl is preferably methyl, ethyl propyl, isopropyl, butyl, isobutyl, or tert-butyl. More preferably, Y is —H or methyl. Even more preferably, $R^2$ is —COOH or —COO—.

According to a preferred embodiment, $R^3$ is selected from the group consisting H and Cl, preferably Cl.

Preferred compounds of Formula I are selected from the group consisting of compounds of Formula II, IIa, III, IIIa, IV, IVa, V, Va, VI, VIa, Vb, Vc, VII and VIa:

(Formula II)

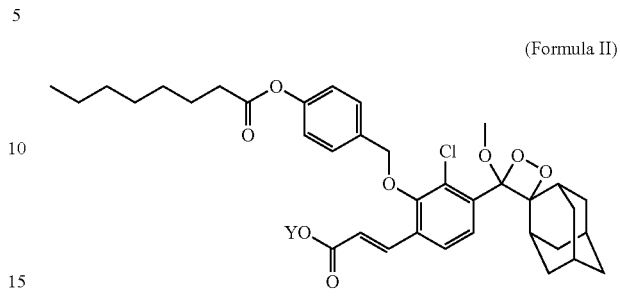

(Formula IIa)

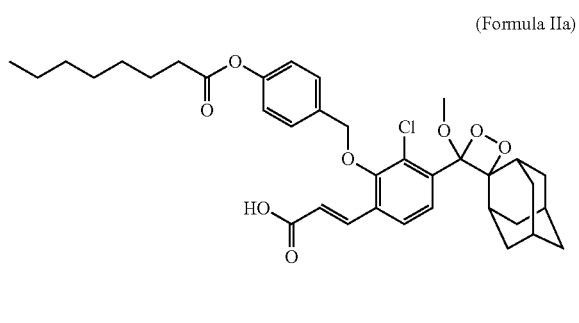

(Formula III)

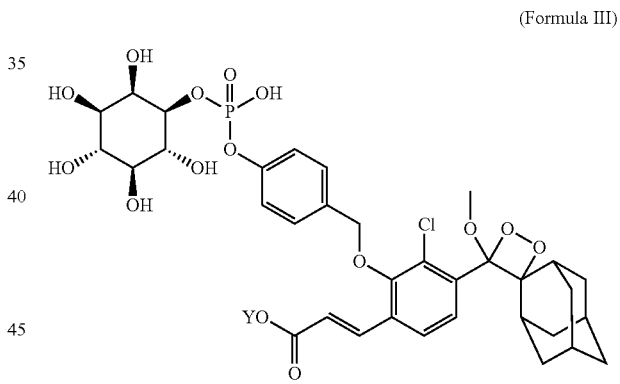

(Formula IIIa)

(Formula IIIb)
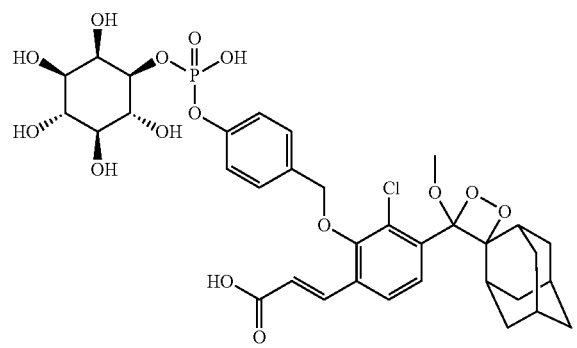
(Formula IV)
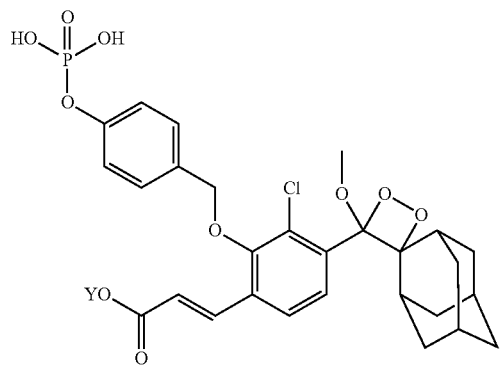
(Formula IVa)
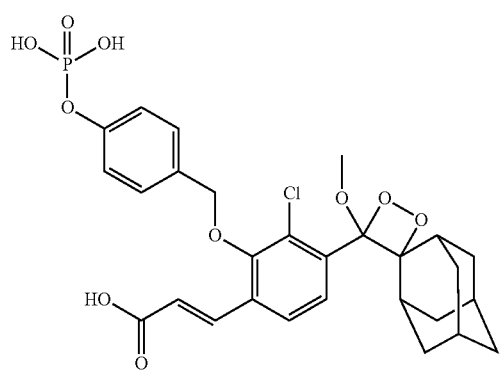
(Formula V)
(Formula Va)
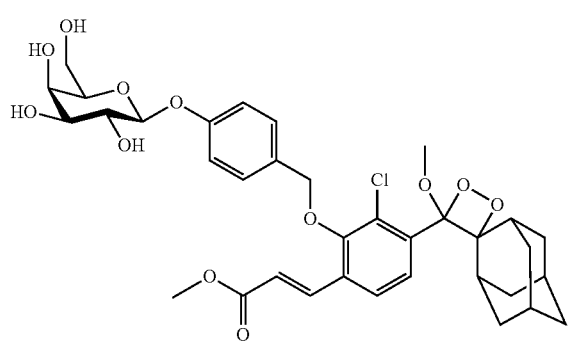
(Formula Vb)
(Formula VI)
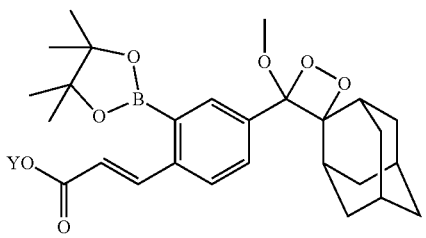
(Formula VIa)
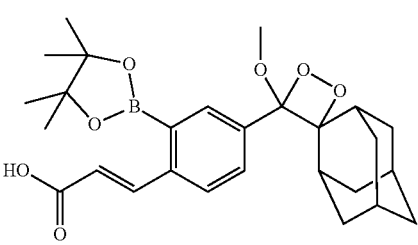
(Formula VIb)
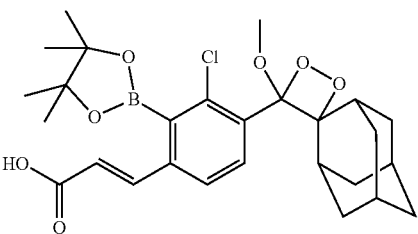

-continued (Formula VIc)

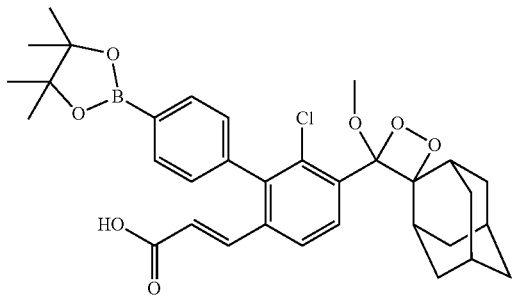

(Formula VII)

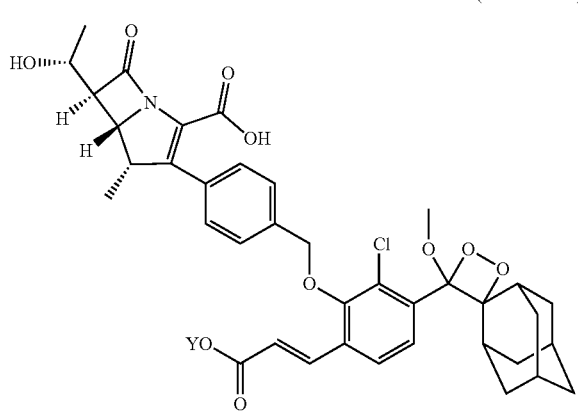

(Formula VIIa)

(Formula VIIb)

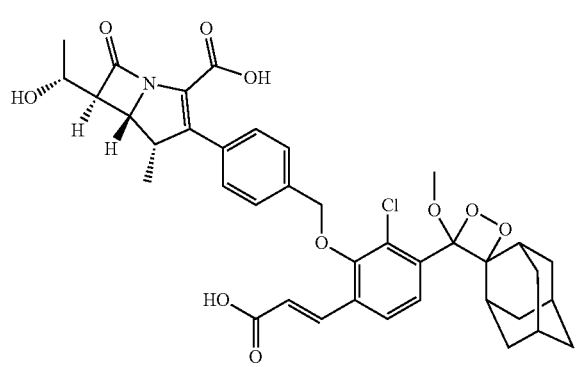

-continued (Formula VIII)

(Formula VIIIa)

wherein Y is H, an optionally substituted C1-C12 alkyl or an alkali metal ion. Particularly preferred compounds are those where Y is H.

The compound of Formula II, in particular Va, has been proven to be particularly suitable for the detection of *Salmonella*, in particular *Salmonella enterica*.

The compound of Formula III, in particular IIb, has been proven to be particularly suitable for the detection of *Listeria* in particular *Listeria monocytogenes*.

The compound of Formula IV, in particular IVa, has been proven to be particularly suitable for the detection of *Staphylococcus aureus*.

The compound of Formula V, in particular Vb, has been proven to be particularly suitable for the detection of coliform and *E. coli*.

The compound of Formula VI, in particular Vc, has been proven to be particularly suitable for the detection of $H_2O_2$, irrespective of its origin.

The compounds of Formula VII and VII, preferably VIIb and VIIIa, have been shown to be particularly suitable for distinguishing carbapenem resistant bacteria from carbapenem sensitive bacteria.

In general, it has been found that when group $R^1$ is present, the compound of Formula I is stable even in aqueous media and no photons are emitted. Removal (at least in part) or modification of the $R^1$ group by means of an interaction with an analyte generates an unstable species, which decomposes through a chemiexcitation process to yield in an excited intermediate, which in turn decays to its ground state through an emission of a photon. Thus, the analyte-responsive group $R^1$ restricts light emission to situations where also an analyte acting on the analyte-responsive group $R^1$ is present.

When $R^1$ is an enzyme-labile group, the compound of Formula I is suitable for the detection of an enzyme and, consequently, for the detection of a microorganism expressing this enzyme. Upon contact with the enzyme, said enzyme-labile group $R^1$ is removed (at least in part) or modified, whereupon the self-immolative linker, if present, is removed from the remainder part of the compound of Formula I and an unstable species is formed, which then decomposes through a chemiexcitation process to yield in an excited intermediate, which in turn decays to its ground state through an emission of a photon.

When $R^1$ is an enzyme-labile group, it is preferred that $R^1$ is responsive to only one specific enzyme, such that a microorganism expressing this enzyme may be detected in the presence of other microorganisms not expressing this enzyme. In this way, it is for example possible to specifically detect *Salmonella* (e.g. *Salmonella Typhimurium* and *Salmonella Enteritidis*) in the presence of other bacteria such as *Citrobacter freundii* and *Escherichia coli*.

Exemplary analyte-responsive groups $R^1$ that (among others) may be used in the present invention and the respective target analytes, the target microorganisms and target metabolites are shown in Table 1. Further analyte-responsive groups the respective analytes, target analytes/target microorganisms/target metabolites are discernible from, e.g., Orenga et al, Journal of Microbiological Methods, 79, 2009, 139-155; and Varadi et al., Che. Soc. Rev., 2017, 46, 4818-4832.

TABLE 1

| $R^1$ | Analyte | Target analyte/target microorganism/target metabolite |
|---|---|---|
| acetyl | Esterase | General substrates for most microorganisms; differentiation of *Campylobacter jejuni* and *C. coli* from *C. lari* |
| butyryl | Esterase | *Moraxella catarrhalis*; General substrates for most microorganisms |
| octanoyl | C8 esterase | *Salmonella* |
| nonanoyl | C9 esterase | *Salmonella* |
| myo-inositol phosphoryl | Phosphatidylinositol-specific phospholipase C (PI-PLC) | *Listeria monocytogenes*; *Bacillus*; *Staphylococcus*; *Clostridium*; *Mycobacterium tuberculosis* |
| phosphoryl | Phosphatase | *Staphylococcus aureus*; *Clostridium perfringens*; *S. agalactiae*; *Candida* spp.; MRSA |
| L-alanyl (A-) | L-alanine aminopeptidase | Gram-negative bacteria; Yeast and molds |
| L-leucinyl (L-) | L-leucine aminopeptidase | Yeast and molds |
| β-alanyl | β-alanyl aminopeptidase | *Pseudomonas aeruginosa* |
| L-pyroglutamic acidyl | PYRase | *Enterococci*; *Streptococcus pyogenes*; *Citrobacter* |
| beta-D-galactopyranosidyl | beta-D-galactosidase | Coliform; *E. coli* |
| alpha-D-galactopyranosidyl | alpha-D-galactosidase | *Salmonella* |
| alpha-D-glucopyranosidyl | alpha-D-glucosidase | *Cronobacter sakazakii*; *Staphylococcus aureus*; MRSA; VRE; *Geobacillus stearothermophilus* (sterilization control) |
| beta-D-glucopyranosidyl | beta-D-glucosidase | *Listeria* spp ESBL producing enterobacteria *Vibrio* *Enterococci* VRE *Candida* spp. *Clostridium difficile* |
| beta-D-glucuronyl | beta-D-glucuronidase | *E. coli*; *Streptococcus agalactiae* |

TABLE 1-continued

| $R^1$ | Analyte | Target analyte/target microorganism/target metabolite |
|---|---|---|
| beta-D-glucuronyl sodium salt | beta-D-glucuronidase | *E. coli*; *Streptococcus agalactiae* |
| n-acetyl-beta-D-galactosaminidyl | Galactosamidase | *Candida albicans* |
| N-acetylneuraminidyl | N-acetylneuraminidase | *Prevotella* |
| cellobiosidyl | Cellobiosidase | *Cronobacter sakazakii* |
| ribofuranosidyl | Ribosidase | *Shigella* |
| choline phosphoryl | Phospholipase C | *Bacillus* |
| -B(Z)(Z'), | $H_2O_2$ | 1) $H_2O_2$ released by a variety of microbial oxidases 2) $H_2O_2$ released by an oxidase reacting on a microbial metabolite/substrate (e.g. glucose oxidase reaction on glucose; or histamine oxidized by diaminoxidase) |
| -B(Z")$_3^-$ Kat$^+$ | | |
| -NO$_2$ | Nitroreductase | General microbial activity |
| oxalylester | Inorganic phosphate | Apyrase (e.g. *Shigella*) |
| Boc-Val-Pro-Argininyl | Limulus clotting factor C | Bacterial Endotoxins |
| Boc-Asp(OBzl)-Pro-Argininyl | Limulus clotting factor C | Bacterial Endotoxins |
| SucOMe-Arg-Pro-Tyrosinyl (SucOMe-RPY-) | Aminopeptidase | *Legionella pneumophila* |
| A beta-lactamase-labile group, preferably a beta-lactam antibiotic, more preferably a penicillin, a cephalosporin of generation 1 to 5, a cephamycin, or a carbapenem | Beta-lactamase | Antibiotic resistant microorganisms; For example suitable for distinguishing beta-lactam sensitive bacteria from beta-lactam resistant bacteria |
| Ac-QLQ- Ac-FQLQ- Ac-EFQLQ- Ac-DEFQLQ- | 3C Cysteine Protease | Detection of norovirus |
| Amides of 5-substituted-o-antranilic acid methyl ester | Hippuricase | *Campylobacter jejuni* |
| Acrylic acid ester | Serine acetyltransferase, Cysteine desulfydrase, Cystein dioxygenase | Cysteine, Total microbial count |

Exemplary preferred $R^1$ groups together with their structural representation and the respective preferred X groups, if L is

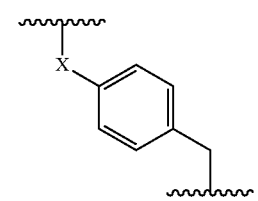

are shown in Table 2. It is however understood that the groups $R^1$ shown in Table 2 may also be used with other linker moieties or may be used without a linker moiety.

TABLE 2

| $R^1$ | Structural representation | Preferred group X, if L is [4-substituted benzyl group] |
|---|---|---|
| acetyl | [structure: acetyl group] | —O— |
| butyryl | [structure: butyryl group] | —O— |
| octanoyl | [structure: octanoyl group] | —O— |
| nonanoyl | [structure: nonanoyl group] | —O— |
| ethylacetyl | [structure: ethylacetyl group] | —NH— |
| myo-inositol phosphoryl | [structure: myo-inositol phosphoryl] | —O— |
| phosphoryl | [structure: phosphoryl group] | —O— |
| amino acidyl | [structure: amino acidyl group] wherein $R^X$ is a side group depending on the respective amino acid. | —NH— |
| di-peptidyl | [structure: di-peptidyl group] wherein $R^X$ and $R^Y$ are side groups depending on the respective amino acids of which the di-peptidyl group is composed. | —NH— |

TABLE 2-continued

| R¹ | Structural representation | Preferred group X, if L is 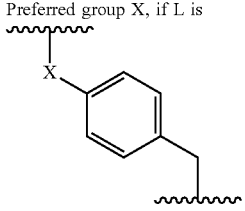 |
|---|---|---|
| tri-peptidyl | 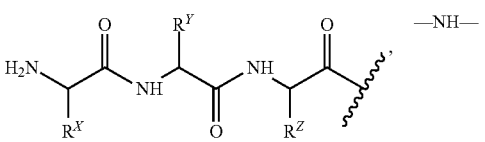 where in $R^X$, $R^Y$ and $R^Z$ are side groups depending on the respective amino acids of which the tri-peptiyl group is composed of. | —NH— |
| L-pyroglutamic acidyl | 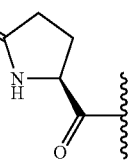 | —NH— |
| beta-D-galactopyranosidyl | 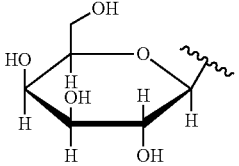 | —O— |
| alpha-D-galactopyranosidyl | 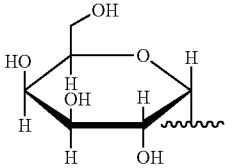 | —O— |
| alpha-D-glucopyranosidyl | 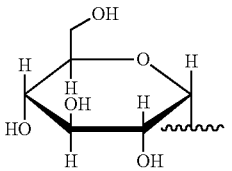 | —O— |
| beta-D-glucopyranosidyl | 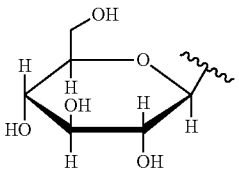 | —O— |
| beta-D-glucuronyl | 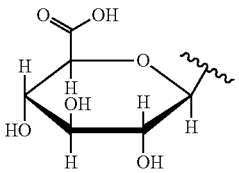 | —O— |

TABLE 2-continued
| | | Preferred group X, if L is 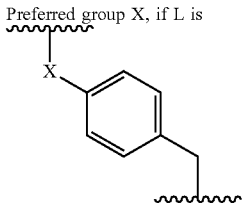 |
|---|---|---|
| R¹ | Structural representation | |
| beta-D-glucuronyl sodium salt | 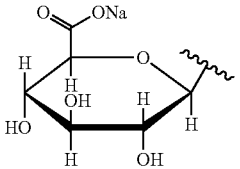 | —O— |
| n-acetyl-beta-D-galactosaminiyl | 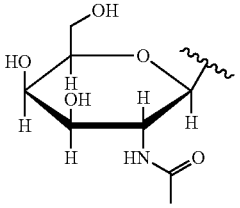 | —O— |
| N-acetylneuraminidyl | 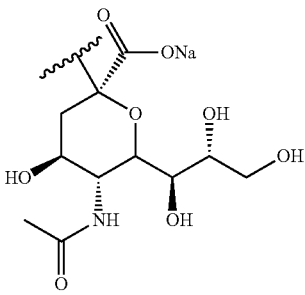 | —O— |
| cellobiosidyl | 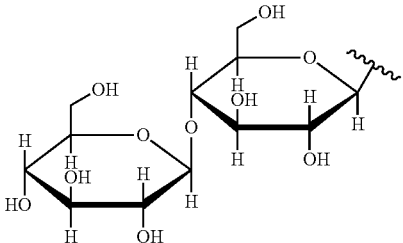 | —O— |
| alpha-D-ribofuranosidyl | 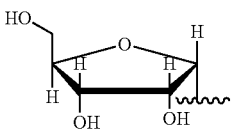 | —O— |
| beta-D-ribofuranosidyl | 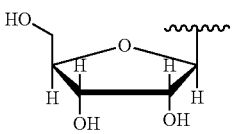 | —O— |
| choline phosphoryl | 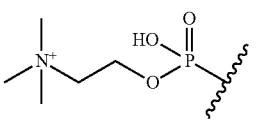 [SMILES: *P(=O)(O)OCC[N+](C)(C)C] | —O— |
| —B(Z)(Z') | —B(Z)(Z') | absent |
| —NO₂ | —NO₂ | absent |

TABLE 2-continued

| R¹ | Structural representation | Preferred group X, if L is 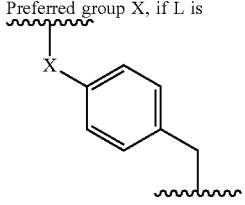 |
|---|---|---|
| oxalylester | 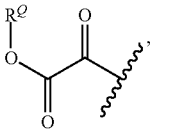<br>wherein R<sup>Q</sup> is an optionally substituted C₁-C₁₂ alkyl group. | —NH— |
| beta-lactamase-labile group | Preferred beta-lactamase labile groups are disclosed above | Depending on the specific beta-lactamase-labile group, linker L may be present or absent |
| Amides of 5-substituted-o-antranilic acid methyl ester | 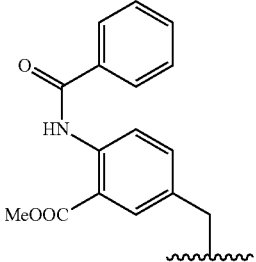 [SMILES: *Cc1ccc(NC(=O)c2ccccc2)c(C(=O)OC)c1] | absent |
| Acrylic acid ester | 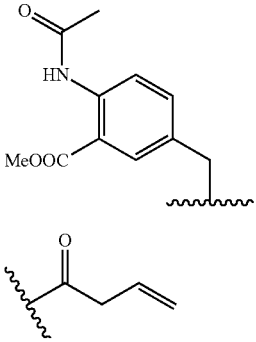 | —O— |

The term "amino acidyl", as used herein, refers to an amino acid moiety that is bound to the remainder part of the dioxetane compound by means of its carboxylic acid group. When an amino acid comprises more than one carboxylic acid group, each of said carboxylic acid groups may bind the amino acid to the remainder part of the dioxetane compound. Preferably, when an amino acid comprises more than one carboxylic acid group, it is bound to the remainder part of the dioxetane compound by means of its alpha-carboxylic acid group.

Consequently, when R¹ is an amino acidyl group or a di- or tri-peptidyl group and X is —NH—, the carboxylic acid group of the amino acidyl group or the di- or tri-peptidyl group (which is involved in bond formation), together with the —NH— group forms an amide group (—CONH—).

Preferred amino acidyl groups are alanyl (A-), preferably L-alanyl, pyroglutamic acidyl, preferably L-pyroglutamic acidyl, argininyl (R—), asparaginyl (N—), aspartic acidyl (D-), cysteinyl (C—), glutaminyl (Q-), glutamic acidyl (E-), glycinyl (G-), histidinyl (H—), isoleucinyl (I—), leucinyl (L-), lysinyl (K—), methioninyl (M-), phenylalanyl (F—), prolinyl (P—), serinyl (S—), threoninyl (T-), tryptophanyl (W—), tyrosinyl (Y—), and valinyl (V—).

Particularly preferred amino acidyl groups are L-alanyl, L-pyroglutamic acidyl, L-leucinyl, or p-alanyl.

Preferred tri-peptidyl groups are Boc-Val-Pro-Argininyl, Boc-Asp(OBzl)-Pro-Argininyl, and SucOMe-Arg-Pro-Tyrosinyl (SucOMe-RPY-).

When R¹ is myo-inositol phosphoryl, the compound of Formula I is particularly suitable for detecting a microorganism expressing Phosphatidylinositol-specific phospholipase C (PI-PLC), e.g. *Listeria*, in particular *Listeria monocytogenes*.

When R¹ is octanoyl, the compound of Formula I is particularly suitable for detecting a microorganism expressing C8 esterase, e.g. *Salmonella*, in particular *Salmonella enterica*.

When R¹ is phosphoryl, the compound of Formula I is particularly suitable for detecting a microorganism expressing a phosphatase, e.g. *S. aureus*, which is a major carrier of antibiotic resistance. Thus, this substrate is ideally suited to detect resistant strains of *S. aureus* (by adding antibiotics to growth medium: Light=Resistance) (See example 8).

According to a preferred embodiment, R¹ is an amino acidyl group, preferably L-alanyl or L-pyroglutamic acidyl, a di-peptidyl group or a tri-peptidyl group (in this case X is preferably —NH—).

According to a preferred embodiment, R¹ is an amino acidyl group.

According to a preferred embodiment, R¹ is myo-inositol phosphoryl, phosphoryl, or octanoyl and R² is

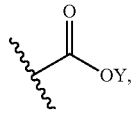

wherein Y is —H or an optionally substituted $C_1$-$C_{12}$ alkyl as defined above, wherein the $C_1$-$C_{12}$ alkyl is preferably methyl. According to a particularly preferred embodiment, R¹ is myo-inositol phosphoryl and R² is

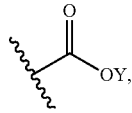

wherein Y is methyl. According to another particularly preferred embodiment, R¹ is octanoyl and R² is

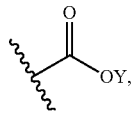

wherein Y is —H. According to another particularly preferred embodiment, R¹ is phosphoryl and R² is

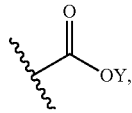

wherein Y is —H.

Particularly preferred compounds are compounds of Formula I, wherein the substituents and variables are defined as follows (the other substituents are defined as set out above) (see Table A; If L is present, L is

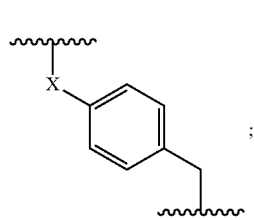

"Carb" stands for

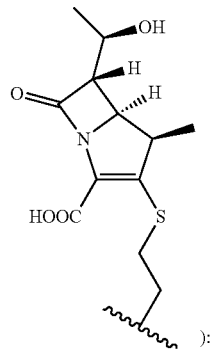 [SMILES: *CCSC1=C(C(=O)O)N2C(=O)[C@H]([C@@H](C)O)[C@H]2[C@H]1C]

):

TABLE A

| n | m | L | X | R¹ | R² | R³ |
|---|---|---|---|---|---|---|
| 1 | 1 | present | —O— | octanoyl | —COOH | H |
| 1 | 1 | present | —O— | octanoyl | —COOH | Cl |
| 1 | 1 | present | —O— | octanoyl | —COOMe | Cl |
| 1 | 1 | present | —O— | octanoyl | —COOMe | H |
| 1 | 1 | present | —O— | octanoyl | —CN | H |
| 1 | 1 | present | —O— | octanoyl | —CN | Cl |
| 0 | 1 | — | — | octanoyl | —COOH | H |
| 0 | 1 | — | — | octanoyl | —COOH | Cl |
| 0 | 1 | — | — | octanoyl | —COOMe | Cl |
| 0 | 1 | — | — | octanoyl | —COOMe | H |
| 0 | 1 | — | — | octanoyl | —CN | H |
| 0 | 1 | — | — | octanoyl | —CN | Cl |
| 1 | 1 | present | —O— | acetyl | —COOH | H |
| 1 | 1 | present | —O— | acetyl | —COOH | Cl |
| 1 | 1 | present | —O— | acetyl | —COOMe | Cl |
| 1 | 1 | present | —O— | acetyl | —COOMe | H |
| 1 | 1 | present | —O— | acetyl | —CN | H |
| 1 | 1 | present | —O— | acetyl | —CN | Cl |
| 0 | 1 | — | — | acetyl | —COOH | H |
| 0 | 1 | — | — | acetyl | —COOH | Cl |
| 0 | 1 | — | — | acetyl | —COOMe | Cl |
| 0 | 1 | — | — | acetyl | —COOMe | H |
| 0 | 1 | — | — | acetyl | —CN | H |
| 0 | 1 | — | — | acetyl | —CN | Cl |
| 1 | 1 | present | —O— | butyryl | —COOH | H |
| 1 | 1 | present | —O— | butyryl | —COOH | Cl |
| 1 | 1 | present | —O— | butyryl | —COOMe | Cl |
| 1 | 1 | present | —O— | butyryl | —COOMe | H |
| 1 | 1 | present | —O— | butyryl | —CN | H |
| 1 | 1 | present | —O— | butyryl | —CN | Cl |
| 0 | 1 | — | — | butyryl | —COOH | H |
| 0 | 1 | — | — | butyryl | —COOH | Cl |
| 0 | 1 | — | — | butyryl | —COOMe | Cl |
| 0 | 1 | — | — | butyryl | —COOMe | H |
| 0 | 1 | — | — | butyryl | —CN | H |
| 0 | 1 | — | — | butyryl | —CN | Cl |
| 1 | 1 | present | —O— | nonanoyl | —COOH | H |
| 1 | 1 | present | —O— | nonanoyl | —COOH | Cl |
| 1 | 1 | present | —O— | nonanoyl | —COOMe | Cl |
| 1 | 1 | present | —O— | nonanoyl | —COOMe | H |
| 1 | 1 | present | —O— | nonanoyl | —CN | H |
| 1 | 1 | present | —O— | nonanoyl | —CN | Cl |
| 0 | 1 | — | — | nonanoyl | —COOH | H |

TABLE A-continued

| n | m | L | X | R¹ | R² | R³ |
|---|---|---|---|---|---|---|
| 0 | 1 | — | — | nonanoyl | —COOH | Cl |
| 0 | 1 | — | — | nonanoyl | —COOMe | Cl |
| 0 | 1 | — | — | nonanoyl | —COOMe | H |
| 0 | 1 | — | — | nonanoyl | —CN | H |
| 0 | 1 | — | — | nonanoyl | —CN | Cl |
| 1 | 1 | present | —NH— | ethyl acetyl | —COOH | H |
| 1 | 1 | present | —NH— | ethyl acetyl | —COOH | Cl |
| 1 | 1 | present | —NH— | ethyl acetyl | —COOMe | Cl |
| 1 | 1 | present | —NH— | ethyl acetyl | —COOMe | H |
| 1 | 1 | present | —NH— | ethyl acetyl | —CN | H |
| 1 | 1 | present | —NH— | ethyl acetyl | —CN | Cl |
| 1 | 1 | present | —O— | myo-inositol phosphoryl | —COOH | H |
| 1 | 1 | present | —O— | myo-inositol phosphoryl | —COOH | Cl |
| 1 | 1 | present | —O— | myo-inositol phosphoryl | —COOMe | Cl |
| 1 | 1 | present | —O— | myo-inositol phosphoryl | —COOMe | H |
| 1 | 1 | present | —O— | myo-inositol phosphoryl | —CN | H |
| 1 | 1 | present | —O— | myo-inositol phosphoryl | —CN | Cl |
| 0 | 1 | — | — | myo-inositol phosphoryl | —COOH | H |
| 0 | 1 | — | — | myo-inositol phosphoryl | —COOH | Cl |
| 0 | 1 | — | — | myo-inositol phosphoryl | —COOMe | Cl |
| 0 | 1 | — | — | myo-inositol phosphoryl | —COOMe | H |
| 0 | 1 | — | — | myo-inositol phosphoryl | —CN | H |
| 0 | 1 | — | — | myo-inositol phosphoryl | —CN | Cl |
| 1 | 1 | present | —O— | phosphoryl | —COOH | H |
| 1 | 1 | present | —O— | phosphoryl | —COOH | Cl |
| 1 | 1 | present | —O— | phosphoryl | —COOMe | Cl |
| 1 | 1 | present | —O— | phosphoryl | —COOMe | H |
| 1 | 1 | present | —O— | phosphoryl | —CN | H |
| 1 | 1 | present | —O— | phosphoryl | —CN | Cl |
| 0 | 1 | — | — | phosphoryl | —COOH | H |
| 0 | 1 | — | — | phosphoryl | —COOH | Cl |
| 0 | 1 | — | — | phosphoryl | —COOMe | Cl |
| 0 | 1 | — | — | phosphoryl | —COOMe | H |
| 0 | 1 | — | — | phosphoryl | —CN | H |
| 0 | 1 | — | — | phosphoryl | —CN | Cl |
| 1 | 1 | present | —NH— | L-alanyl | —COOH | H |
| 1 | 1 | present | —NH— | L-alanyl | —COOH | Cl |
| 1 | 1 | present | —NH— | L-alanyl | —COOMe | Cl |
| 1 | 1 | present | —NH— | L-alanyl | —COOMe | H |
| 1 | 1 | present | —NH— | L-alanyl | —CN | H |
| 1 | 1 | present | —NH— | L-alanyl | —CN | Cl |
| 1 | 1 | present | —NH— | L-leucinyl | —COOH | H |
| 1 | 1 | present | —NH— | L-leucinyl | —COOH | Cl |
| 1 | 1 | present | —NH— | L-leucinyl | —COOMe | Cl |
| 1 | 1 | present | —NH— | L-leucinyl | —COOMe | H |
| 1 | 1 | present | —NH— | L-leucinyl | —CN | H |
| 1 | 1 | present | —NH— | L-leucinyl | —CN | Cl |
| 1 | 1 | present | —NH— | beta-alanyl | —COOH | H |
| 1 | 1 | present | —NH— | beta-alanyl | —COOH | Cl |
| 1 | 1 | present | —NH— | beta-alanyl | —COOMe | Cl |
| 1 | 1 | present | —NH— | beta-alanyl | —COOMe | H |
| 1 | 1 | present | —NH— | beta-alanyl | —CN | H |
| 1 | 1 | present | —NH— | beta-alanyl | —CN | Cl |
| 1 | 1 | present | —NH— | L-pyroglutamic acidyl | —COOH | H |
| 1 | 1 | present | —NH— | L-pyroglutamic acidyl | —COOH | Cl |
| 1 | 1 | present | —NH— | L-pyroglutamic acidyl | —COOMe | Cl |
| 1 | 1 | present | —NH— | L-pyroglutamic acidyl | —COOMe | H |
| 1 | 1 | present | —NH— | L-pyroglutamic acidyl | —CN | H |
| 1 | 1 | present | —NH— | L-pyroglutamic acidyl | —CN | Cl |
| 1 | 1 | present | —O— | beta-D-galactopyranosidyl | —COOH | H |
| 1 | 1 | present | —O— | beta-D-galactopyranosidyl | —COOH | Cl |
| 1 | 1 | present | —O— | beta-D-galactopyranosidyl | —COOMe | Cl |
| 1 | 1 | present | —O— | beta-D-galactopyranosidyl | —COOMe | H |
| 1 | 1 | present | —O— | beta-D-galactopyranosidyl | —CN | H |
| 1 | 1 | present | —O— | beta-D-galactopyranosidyl | —CN | Cl |
| 0 | 1 | — | — | beta-D-galactopyranosidyl | —COOH | H |
| 0 | 1 | — | — | beta-D-galactopyranosidyl | —COOH | Cl |
| 0 | 1 | — | — | beta-D-galactopyranosidyl | —COOMe | Cl |
| 0 | 1 | — | — | beta-D-galactopyranosidyl | —COOMe | H |
| 0 | 1 | — | — | beta-D-galactopyranosidyl | —CN | H |
| 0 | 1 | — | — | beta-D-galactopyranosidyl | —CN | Cl |
| 1 | 1 | present | —O— | alpha-D-galactopyranosidyl | —COOH | H |
| 1 | 1 | present | —O— | alpha-D-galactopyranosidyl | —COOH | Cl |
| 1 | 1 | present | —O— | alpha-D-galactopyranosidyl | —COOMe | Cl |
| 1 | 1 | present | —O— | alpha-D-galactopyranosidyl | —COOMe | H |
| 1 | 1 | present | —O— | alpha-D-galactopyranosidyl | —CN | H |
| 1 | 1 | present | —O— | alpha-D-galactopyranosidyl | —CN | Cl |
| 0 | 1 | — | — | alpha-D-galactopyranosidyl | —COOH | H |
| 0 | 1 | — | — | alpha-D-galactopyranosidyl | —COOH | Cl |
| 0 | 1 | — | — | alpha-D-galactopyranosidyl | —COOMe | Cl |
| 0 | 1 | — | — | alpha-D-galactopyranosidyl | —COOMe | H |
| 0 | 1 | — | — | alpha-D-galactopyranosidyl | —CN | H |
| 0 | 1 | — | — | alpha-D-galactopyranosidyl | —CN | Cl |
| 1 | 1 | present | —O— | alpha-D-glucopyranosidyl | —COOH | H |
| 1 | 1 | present | —O— | alpha-D-glucopyranosidyl | —COOH | Cl |
| 1 | 1 | present | —O— | alpha-D-glucopyranosidyl | —COOMe | Cl |
| 1 | 1 | present | —O— | alpha-D-glucopyranosidyl | —COOMe | H |
| 1 | 1 | present | —O— | alpha-D-glucopyranosidyl | —CN | H |
| 1 | 1 | present | —O— | alpha-D-glucopyranosidyl | —CN | Cl |
| 0 | 1 | — | — | alpha-D-glucopyranosidyl | —COOH | H |
| 0 | 1 | — | — | alpha-D-glucopyranosidyl | —COOH | Cl |
| 0 | 1 | — | — | alpha-D-glucopyranosidyl | —COOMe | Cl |
| 0 | 1 | — | — | alpha-D-glucopyranosidyl | —COOMe | H |
| 0 | 1 | — | — | alpha-D-glucopyranosidyl | —CN | H |
| 0 | 1 | — | — | alpha-D-glucopyranosidyl | —CN | Cl |
| 1 | 1 | present | —O— | beta-D-glucopyranosidyl | —COOH | H |
| 1 | 1 | present | —O— | beta-D-glucopyranosidyl | —COOH | Cl |
| 1 | 1 | present | —O— | beta-D-glucopyranosidyl | —COOMe | Cl |
| 1 | 1 | present | —O— | beta-D-glucopyranosidyl | —COOMe | H |
| 1 | 1 | present | —O— | beta-D-glucopyranosidyl | —CN | H |
| 1 | 1 | present | —O— | beta-D-glucopyranosidyl | —CN | Cl |
| 0 | 1 | — | — | beta-D-glucopyranosidyl | —COOH | H |
| 0 | 1 | — | — | beta-D-glucopyranosidyl | —COOH | Cl |
| 0 | 1 | — | — | beta-D-glucopyranosidyl | —COOMe | Cl |
| 0 | 1 | — | — | beta-D-glucopyranosidyl | —COOMe | H |
| 0 | 1 | — | — | beta-D-glucopyranosidyl | —CN | H |
| 0 | 1 | — | — | beta-D-glucopyranosidyl | —CN | Cl |
| 1 | 1 | present | —O— | beta-D-glucuronyl | —COOH | H |
| 1 | 1 | present | —O— | beta-D-glucuronyl | —COOH | Cl |
| 1 | 1 | present | —O— | beta-D-glucuronyl | —COOMe | Cl |
| 1 | 1 | present | —O— | beta-D-glucuronyl | —COOMe | H |
| 1 | 1 | present | —O— | beta-D-glucuronyl | —CN | H |
| 1 | 1 | present | —O— | beta-D-glucuronyl | —CN | Cl |
| 0 | 1 | — | — | beta-D-glucuronyl | —COOH | H |
| 0 | 1 | — | — | beta-D-glucuronyl | —COOH | Cl |
| 0 | 1 | — | — | beta-D-glucuronyl | —COOMe | Cl |
| 0 | 1 | — | — | beta-D-glucuronyl | —COOMe | H |
| 0 | 1 | — | — | beta-D-glucuronyl | —CN | H |
| 0 | 1 | — | — | beta-D-glucuronyl | —CN | Cl |
| 1 | 1 | present | —O— | beta-D-glucuronyl sodium salt | —COOH | H |
| 1 | 1 | present | —O— | beta-D-glucuronyl sodium salt | —COOH | Cl |
| 1 | 1 | present | —O— | beta-D-glucuronyl sodium salt | —COOMe | Cl |
| 1 | 1 | present | —O— | beta-D-glucuronyl sodium salt | —COOMe | H |
| 1 | 1 | present | —O— | beta-D-glucuronyl sodium salt | —CN | H |
| 1 | 1 | present | —O— | beta-D-glucuronyl sodium salt | —CN | Cl |
| 0 | 1 | — | — | beta-D-glucuronyl sodium salt | —COOH | H |
| 0 | 1 | — | — | beta-D-glucuronyl sodium salt | —COOH | Cl |
| 0 | 1 | — | — | beta-D-glucuronyl sodium salt | —COOMe | Cl |
| 0 | 1 | — | — | beta-D-glucuronyl sodium salt | —COOMe | H |
| 0 | 1 | — | — | beta-D-glucuronyl sodium salt | —CN | H |
| 0 | 1 | — | — | beta-D-glucuronyl sodium salt | —CN | Cl |
| 1 | 1 | present | —O— | N-acetyl-beta-D-galactosaminidyl | —COOH | H |
| 1 | 1 | present | —O— | N-acetyl-beta-D-galactosaminidyl | —COOH | Cl |
| 1 | 1 | present | —O— | N-acetyl-beta-D-galactosaminidyl | —COOMe | Cl |
| 1 | 1 | present | —O— | N-acetyl-beta-D-galactosaminidyl | —COOMe | H |
| 1 | 1 | present | —O— | N-acetyl-beta-D-galactosaminidyl | —CN | H |
| 1 | 1 | present | —O— | N-acetyl-beta-D-galactosaminidyl | —CN | Cl |
| 0 | 1 | — | — | N-acetyl-beta-D-galactosaminidyl | —COOH | H |
| 0 | 1 | — | — | N-acetyl-beta-D-galactosaminidyl | —COOH | Cl |
| 0 | 1 | — | — | N-acetyl-beta-D-galactosaminidyl | —COOMe | Cl |
| 0 | 1 | — | — | N-acetyl-beta-D-galactosaminidyl | —COOMe | H |
| 0 | 1 | — | — | N-acetyl-beta-D-galactosaminidyl | —CN | H |
| 0 | 1 | — | — | N-acetyl-beta-D-galactosaminidyl | —CN | Cl |

TABLE A-continued

| n | m | L | X | R¹ | R² | R³ |
|---|---|---|---|---|---|---|
| 1 | 1 | present | —O— | N-acetylneuraminidyl | —COOH | H |
| 1 | 1 | present | —O— | N-acetylneuraminidyl | —COOH | Cl |
| 1 | 1 | present | —O— | N-acetylneuraminidyl | —COOMe | Cl |
| 1 | 1 | present | —O— | N-acetylneuraminidyl | —COOMe | H |
| 1 | 1 | present | —O— | N-acetylneuraminidyl | —CN | H |
| 1 | 1 | present | —O— | N-acetylneuraminidyl | —CN | Cl |
| 0 | 1 | — | — | N-acetylneuraminidyl | —COOH | H |
| 0 | 1 | — | — | N-acetylneuraminidyl | —COOH | Cl |
| 0 | 1 | — | — | N-acetylneuraminidyl | —COOMe | Cl |
| 0 | 1 | — | — | N-acetylneuraminidyl | —COOMe | H |
| 0 | 1 | — | — | N-acetylneuraminidyl | —CN | H |
| 0 | 1 | — | — | N-acetylneuraminidyl | —CN | Cl |
| 1 | 1 | present | —O— | cellobiosidyl | —COOH | H |
| 1 | 1 | present | —O— | cellobiosidyl | —COOH | Cl |
| 1 | 1 | present | —O— | cellobiosidyl | —COOMe | Cl |
| 1 | 1 | present | —O— | cellobiosidyl | —COOMe | H |
| 1 | 1 | present | —O— | cellobiosidyl | —CN | H |
| 1 | 1 | present | —O— | cellobiosidyl | —CN | Cl |
| 0 | 1 | — | — | cellobiosidyl | —COOH | H |
| 0 | 1 | — | — | cellobiosidyl | —COOH | Cl |
| 0 | 1 | — | — | cellobiosidyl | —COOMe | Cl |
| 0 | 1 | — | — | cellobiosidyl | —COOMe | H |
| 0 | 1 | — | — | cellobiosidyl | —CN | H |
| 0 | 1 | — | — | cellobiosidyl | —CN | Cl |
| 1 | 1 | present | —O— | ribofuranosidyl | —COOH | H |
| 1 | 1 | present | —O— | ribofuranosidyl | —COOH | Cl |
| 1 | 1 | present | —O— | ribofuranosidyl | —COOMe | Cl |
| 1 | 1 | present | —O— | ribofuranosidyl | —COOMe | H |
| 1 | 1 | present | —O— | ribofuranosidyl | —CN | H |
| 1 | 1 | present | —O— | ribofuranosidyl | —CN | Cl |
| 0 | 1 | — | — | ribofuranosidyl | —COOH | H |
| 0 | 1 | — | — | ribofuranosidyl | —COOH | Cl |
| 0 | 1 | — | — | ribofuranosidyl | —COOMe | Cl |
| 0 | 1 | — | — | ribofuranosidyl | —COOMe | H |
| 0 | 1 | — | — | ribofuranosidyl | —CN | H |
| 0 | 1 | — | — | ribofuranosidyl | —CN | Cl |
| 1 | 1 | present | —O— | choline phosphoryl | —COOH | H |
| 1 | 1 | present | —O— | choline phosphoryl | —COOH | Cl |
| 1 | 1 | present | —O— | choline phosphoryl | —COOMe | Cl |
| 1 | 1 | present | —O— | choline phosphoryl | —COOMe | H |
| 1 | 1 | present | —O— | choline phosphoryl | —CN | H |
| 1 | 1 | present | —O— | choline phosphoryl | —CN | Cl |
| 0 | 1 | — | — | choline phosphoryl | —COOH | H |
| 0 | 1 | — | — | choline phosphoryl | —COOH | Cl |
| 0 | 1 | — | — | choline phosphoryl | —COOMe | Cl |
| 0 | 1 | — | — | choline phosphoryl | —COOMe | H |
| 0 | 1 | — | — | choline phosphoryl | —CN | H |
| 0 | 1 | — | — | choline phosphoryl | —CN | Cl |
| 1 | 1 | present | — | (4,4,5,5-tetramethyl-1,3,2-dioxaborolan-2-yl) | —COOH | H |
| 1 | 1 | present | — | (4,4,5,5-tetramethyl-1,3,2-dioxaborolan-2-yl) | —COOH | Cl |
| 1 | 1 | present | — | (4,4,5,5-tetramethyl-1,3,2-dioxaborolan-2-yl) | —COOMe | Cl |
| 1 | 1 | present | — | (4,4,5,5-tetramethyl-1,3,2-dioxaborolan-2-yl) | —COOMe | H |
| 1 | 1 | present | — | (4,4,5,5-tetramethyl-1,3,2-dioxaborolan-2-yl) | —CN | H |
| 1 | 1 | present | — | (4,4,5,5-tetramethyl-1,3,2-dioxaborolan-2-yl) | —CN | Cl |
| 0 | 0 | — | — | (4,4,5,5-tetramethyl-1,3,2-dioxaborolan-2-yl) | —COOH | H |
| 0 | 0 | — | — | (4,4,5,5-tetramethyl-1,3,2-dioxaborolan-2-yl) | —COOH | Cl |
| 0 | 0 | — | — | (4,4,5,5-tetramethyl-1,3,2-dioxaborolan-2-yl) | —COOMe | Cl |
| 0 | 0 | — | — | (4,4,5,5-tetramethyl-1,3,2-dioxaborolan-2-yl) | —COOMe | H |
| 0 | 0 | — | — | (4,4,5,5-tetramethyl-1,3,2-dioxaborolan-2-yl) | —CN | H |
| 0 | 0 | — | — | (4,4,5,5-tetramethyl-1,3,2-dioxaborolan-2-yl) | —CN | Cl |
| 1 | 1 | present | — | —NO₂ | —COOH | H |
| 1 | 1 | present | — | —NO₂ | —COOH | Cl |
| 1 | 1 | present | — | —NO₂ | —COOMe | Cl |
| 1 | 1 | present | — | —NO₂ | —COOMe | H |
| 1 | 1 | present | — | —NO₂ | —CN | H |
| 1 | 1 | present | — | —NO₂ | —CN | Cl |
| 1 | 1 | present | —O— | oxalylester | —COOH | H |

TABLE A-continued

| n | m | L | X | R¹ | R² | R³ |
|---|---|---|---|---|---|---|
| 1 | 1 | present | —O— | oxalylester | —COOH | Cl |
| 1 | 1 | present | —O— | oxalylester | —COOMe | Cl |
| 1 | 1 | present | —O— | oxalylester | —COOMe | H |
| 1 | 1 | present | —O— | oxalylester | —CN | H |
| 1 | 1 | present | —O— | oxalylester | —CN | Cl |
| 0 | 1 | — | — | oxalylester | —COOH | H |
| 0 | 1 | — | — | oxalylester | —COOH | Cl |
| 0 | 1 | — | — | oxalylester | —COOMe | Cl |
| 0 | 1 | — | — | oxalylester | —COOMe | H |
| 0 | 1 | — | — | oxalylester | —CN | H |
| 0 | 1 | — | — | oxalylester | —CN | Cl |
| 1 | 1 | present | —NH— | Boc-Val-Pro-Argininyl | —COOH | H |
| 1 | 1 | present | —NH— | Boc-Val-Pro-Argininyl | —COOH | Cl |
| 1 | 1 | present | —NH— | Boc-Val-Pro-Argininyl | —COOMe | Cl |
| 1 | 1 | present | —NH— | Boc-Val-Pro-Argininyl | —COOMe | H |
| 1 | 1 | present | —NH— | Boc-Val-Pro-Argininyl | —CN | H |
| 1 | 1 | present | —NH— | Boc-Val-Pro-Argininyl | —CN | Cl |
| 1 | 1 | present | —NH— | Boc-Asp(OBzl)-Pro-Argininyl | —COOH | H |
| 1 | 1 | present | —NH— | Boc-Asp(OBzl)-Pro-Argininyl | —COOH | Cl |
| 1 | 1 | present | —NH— | Boc-Asp(OBzl)-Pro-Argininyl | —COOMe | Cl |
| 1 | 1 | present | —NH— | Boc-Asp(OBzl)-Pro-Argininyl | —COOMe | H |
| 1 | 1 | present | —NH— | Boc-Asp(OBzl)-Pro-Argininyl | —CN | H |
| 1 | 1 | present | —NH— | Boc-Asp(OBzl)-Pro-Argininyl | —CN | Cl |
| 1 | 1 | present | —NH— | SucOMe-Arg-Pro-Tyrosinyl | —COOH | H |
| 1 | 1 | present | —NH— | SucOMe-Arg-Pro-Tyrosinyl | —COOH | Cl |
| 1 | 1 | present | —NH— | SucOMe-Arg-Pro-Tyrosinyl | —COOMe | Cl |
| 1 | 1 | present | —NH— | SucOMe-Arg-Pro-Tyrosinyl | —COOMe | H |
| 1 | 1 | present | —NH— | SucOMe-Arg-Pro-Tyrosinyl | —CN | H |
| 1 | 1 | present | —NH— | SucOMe-Arg-Pro-Tyrosinyl | —CN | Cl |
| 1 | 1 | present | — | Carb | —COOH | H |
| 1 | 1 | present | — | Carb | —COOH | Cl |
| 1 | 1 | present | — | Carb | —COOMe | Cl |
| 1 | 1 | present | — | Carb | —COOMe | H |
| 1 | 1 | present | — | Carb | —CN | H |
| 1 | 1 | present | — | Carb | —CN | Cl |

Generally, all uses and methods discussed hereinbelow are to be understood to be in-vitro uses and methods.

In a second aspect, the present invention relates to the use of a compound of Formula I as described in the first aspect for the detection of a target analyte (e.g. hydrogen peroxide)/target microorganism/target metabolite (irrespective of its origin). More preferably, the present invention relates to the use of a compound of Formula I as described in the first aspect for the detection of a target microorganism, more preferably a pathogenic microorganism, even more preferably, a bacterium, virus or fungi.

In particular, the present invention relates to the use of a compound of Formula I as described in the first aspect for the detection of presence or absence, quantification and identification of microorganisms including bacteria, bacterial fragments (e.g., LPS, endotoxin), viruses, fungi as well as other pathogens. More particularly, the present invention relates to the use of a compound of Formula I as described in the first aspect for the detection of presence or absence, quantification and identification of microorganisms including bacteria, bacterial fragments (e.g., LPS, endotoxin), viruses, fungi as well as other pathogens by means of chemiluminescent indication of action of metabolic, reagent or reference enzymes on suitable molecular probes, indication of hydrogen peroxide resulting from enzymatic oxidation of microbial metabolites or nutrients by reagent enzymes or detection of inorganic phosphate playing roles of nutrient, substrate, metabolic product or by-product of action by a reagent enzyme.

Preferably, the microorganism is selected from the group consisting of *Salmonella; Salmonella enterica; Listeria*, preferably, *Listeria monocytogenes; S. aureus; E. coli*; carbapenem-resistant bacteria, preferably *Pseudomonas aeruginosa*, and *Klebsiella pneumonia; Campylobacter jejuni; C. coli; C. lari; Bacillus; Staphylococcus; Clostridium; Mycobacterium tuberculosis; Clostridium perfringens; S. agalactiae; Candida* spp.; Gram negative bacteria, yeast, molds, *Pseudomonas aeruginosa*, Enterococci, *Streptococcus pyogenes; Citrobacter, Coliform; Cronobacter sakazakii*; MRSA, VRE, *Geobacillus stearothermophilus; Listeria* spp., ESBL producing enterobacteria; *Vibrio; Clostridium difficile; Candida albicans; Prevotella; Shigella*, a microorganism containing apyrase, preferably *Shigella; Legionella* pneumophilia; and a virus of the Caliciviridae family, preferably a Lagovirus, a Norovirus, a Sapovirus, a Nebovirus, a Recovirus, more preferably a Norovirus Preferably, the microorganism is selected from the group consisting of *Salmonella, Salmonella enterica, Listeria*, preferably, *Listeria monocytogenes, S. aureus, E. coli*, carbapenem-resistant bacteria, preferably *Pseudomonas aeruginosa* and *Klebsiella pneumonia*.

Which substituents R¹ of the compound of Formula I are suitable for the detection of which target analyte (e.g. hydrogen peroxide)/target microorganism/target metabolite is evident from the first aspect, in particular from Table 1, wherein the other substituents may be chosen as defined in the first aspect (this applies for all aspects and embodiments of the present invention).

As described above, it has surprisingly been found that the compound of Formula I shows a number of advantages when used for the detection of microorganisms. In particular, the compound of Formula I allows for a remarkably easy, straight-forward and reliable detection of microorganisms, because the compound of Formula I can simply be added as it is to a microorganism-containing medium without the need for any further compounds or for an additional preparation of the medium. This is a huge advantage over the commonly applied luciferase-luciferin system, which requires the use of multiple compounds, one of which, i.e. luciferase, is quite costly and limits shelf-life due to notorious instability. Furthermore, it has been shown that the compound of Formula I is stable in aqueous media and has a sensitivity that is significantly higher than that of a luciferase-luciferin system. (see Examples 9 and 10).

When used for the detection of a microorganism, the compound of Formula I can be added to the microorganism (one or more), in particular to a microorganism-containing medium (preferably aqueous), in solid form or in solution. However, using the compound of Formula I in solution, preferably DMSO solution, is preferred for the following reason: Due to the high sensitivity (significantly higher than that of a luciferase-luciferin system), only a very small amount of the compound of Formula I is required. Typically, the compound of Formula I is used in an amount of less than 0.1 µg, preferably less than 0.09 µg, more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg. Thus, using the compound of Formula I in solution, particularly DMSO solution, allows for an easy determination of the correct quantity added to the microorganism-containing medium by means of aliquotation from a stock solution of a known concentration. Furthermore, it has been found that the compound of Formula I is highly stable in DMSO solution (several months at room temperature and years at 4° C.).

According to a preferred embodiment, the compound of Formula I is used for the detection of a target analyte (e.g. hydrogen peroxide)/target microorganism/target metabolite, preferably a microorganism, wherein the group R¹ is responsive to an analyte, in particular an enzyme expressed by said microorganism. Whether group R¹ is responsive to a specific analyte, e.g. an enzyme, may simply be determined by adding a compound of Formula I comprising said group R¹ to the respective analyte (or vice versa) and detecting the emitted photons (i.e. light), if any.

According to a preferred embodiment, the microorganism is *Salmonella*, preferably *Salmonella enterica*, *Listeria*, preferably *Listeria monocytogenes*, *S. aureus* or *E. coli*.

According to a preferred embodiment, the microorganism is *Salmonella*, preferably *Salmonella enterica*, and the compound is a compound of Formula II:

(Formula II)

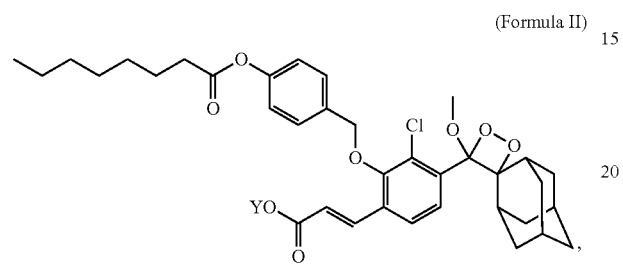

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl. Preferably, a compound of Formula IIa is used.

According to a particularly preferred embodiment, the microorganism is *Salmonella*, preferably *Salmonella enterica*, and the compound is a compound of Formula IIa.

According to another preferred embodiment, the microorganism is *Listeria, preferably Listeria monocytogenes*, and the compound is a compound of Formula III:

(Formula III)

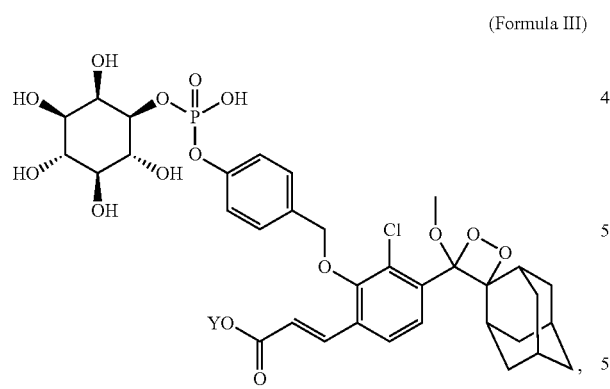

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl. Preferably, a compound of Formula IIIa or IIIb, more preferably IIIb, is used.

According to a particularly preferred embodiment, the microorganism is *Listeria*, preferably *Listeria monocytogenes*, and the compound is a compound of Formula IIIb.

According to another preferred embodiment, the microorganism is *S. aureus* and the compound is a compound of Formula IV:

(Formula IV)

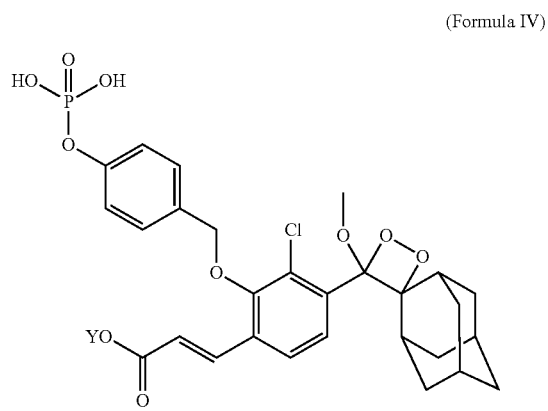

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl. Preferably, a compound of Formula IVa is used.

According to a particularly preferred embodiment, the microorganism is *S. aureus* and the compound is a compound of Formula IVa.

According to another preferred embodiment, the microorganism is *E. coli* and the compound is a compound of Formula V:

(Formula V)

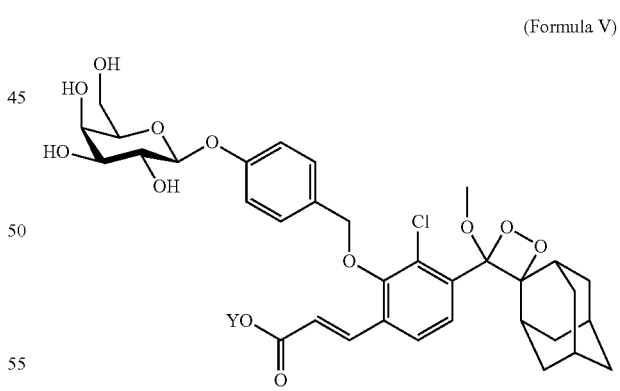

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-C12 alkyl, wherein the optionally substituted $C_1$-$C_{12}$ alkyl is preferably methyl, ethyl, propyl, isopropyl, butyl, isobutyl, or tert-butyl. More preferably, Y is —H or methyl. Preferably, a compound of Formula Va or Vb, more preferably Vb, is used.

According to a particularly preferred embodiment, the microorganism is *E. coli* and the compound is a compound of Formula Vb.

According to a preferred embodiment, the target analyte/target microorganism/target metabolite is hydrogen peroxide and the compound of Formula I is a compound of Formula VI, Via, Vb, or Vc. In particular, growth substrates and metabolites such as glucose can be detected directly in supernatants of microbial cultures by chemiluminescence when using a compound of Formula I, wherein $R^1$ is —B(Z)(Z') as defined in the first aspect and the other substituents are as defined in the first aspect (preferably a compound of Formula VI, VIa, VIb, or Vc), in combination with suitable hydrogen peroxide-releasing enzymes (e.g. oxidases). Preferably, a compound of Formula VI, in particular a compound of Formula Via, Vb, or Vic, most preferably Vic, or related compounds are used.

According to another preferred embodiment, the microorganism are carbapenem-resistant bacteria, e.g., *Pseudomonas aeruginosa* or *Klebsiella pneumonia*, and the compound is a compound of Formula VII or VIII (Formula VII)

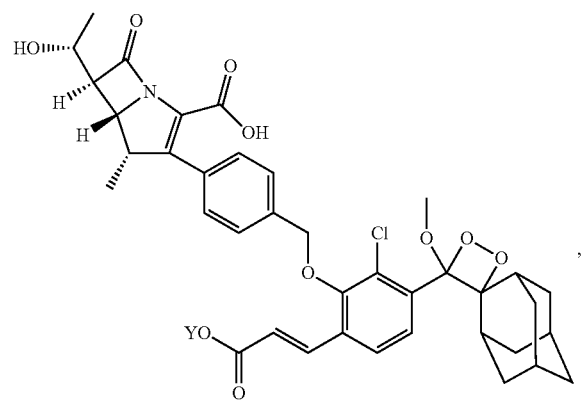

(Formula VIII)

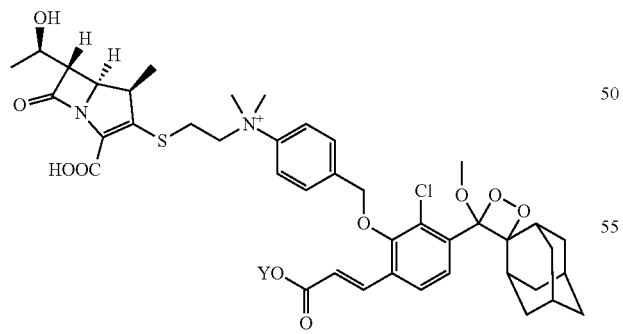

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl. Preferably, a compound of Formula Vila, VIIb, or VIIIa, more preferably VIIb or VIIIa, even more preferably VIIIa, is used.

According to a particularly preferred embodiment, the microorganisms are carbapenem-resistant *Pseudomonas aeruginosa* and *Klebsiella pneumonia* and the compound is a compound of Formula VIIb or VIIIa.

Further target analytes/target microorganisms/target metabolites as well as specific compounds of Formula I, in particular groups R, suitable for their detection are discernible from the first aspect of the invention.

Further, the present invention relates to a method for the detection of a target analyte (e.g. hydrogen peroxide)/target microorganism/target metabolite.

Preferably, the present invention relates to a method for the detection of a target microorganism. In particular, the present invention relates to a method for the detection of presence or absence, quantification and identification of microorganisms including bacteria, bacterial fragments (e.g., LPS, endotoxin), viruses, fungi as well as other pathogens. More particularly, the present invention relates to a method for the detection of presence or absence, quantification and identification of microorganisms including bacteria, bacterial fragments (e.g., LPS, endotoxin), viruses, fungi as well as other pathogens by means of chemiluminescent indication of action of metabolic, reagent or reference enzymes on suitable molecular probes, indication of hydrogen peroxide resulting from enzymatic oxidation of microbial metabolites or nutrients by reagent enzymes or detection of inorganic phosphate playing roles of nutrient, substrate, metabolic product or by-product of action by a reagent enzyme.

The method comprises the steps of a) providing a medium comprising one or more target analytes (e.g. hydrogen peroxide)/target microorganisms/target metabolites, b) adding a compound of Formula I as described in the first embodiment to the medium so that the compound of Formula I emits light, and c) detecting the emitted light.

If the compound of Formula I comprises group $R^1$ that is

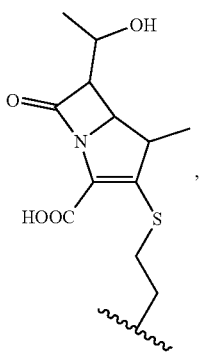 [SMILES: *CCSC1=C(C(=O)O)N2C(=O)C(C(C)O)C2C1C]

preferably

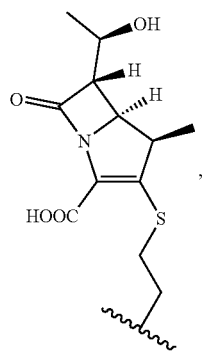 [SMILES: *CCSC1=C(C(=O)O)N2C(=O)[C@H]([C@@H](C)O)[C@H]2[C@H]1C]

which is connected to a linker by means of a —N⁺(CH₃)₂- moiety (see above) then also an oxidizing agent (preferably hydrogen peroxide) is preferably added in step b). This is because opening of the beta-lactam ring by means of a carbapenemase, does not directly lead to the generation of an emissive species. Rather, oxidation of the sulfide moiety is required to initiate a Hofmann elimination reaction which finally leads to self-immolation of the linker and, thus, to the generation of an emissive species.

According to a preferred embodiment, the method comprises an additional step of lysis, which may be carried out between steps a) and b) or in step b) together with or after adding a compound of Formula I to the medium. In one example, an unspecific lysis reagent such as ethanol or another suitable solvent mixture (preferably in an amount of 15%) may be added to the medium. In this way, intracellular enzymes are released into the medium and can be detected by means of a compound of Formula I. In another example, a selective lysis reagent such as phages, peptides, proteins (in particular endolysins and derivatives thereof) may be added to the medium. Said selective lysis reagents lead to the release of intracellular enzymes of only specific cells (i.e., cells that are responsive to a respective selective lysis reagent). Thus, said selective lysis reagents represent, in addition to the detected enzyme, a further selection criterion, which prevents false-positive results and increases specificity. This applies, in principle, also to all further aspects disclosed herein.

A further example of increasing specificity is the use of antibody-based capturing methods. For example, antibody-functionalized magnetic beads may be added after steps a) and b). Thus, specific cells may be collected/separated from other cells, which increases specificity. In this way, the high specificity of antibodies can be combined with the capability of the compound of Formula I for detecting metabolically active bacteria with high sensitivity. This applies, in principle, also to all further aspects disclosed herein.

Preferably, the medium is an aqueous medium.

Preferably, the target analyte/target microorganism/target metabolite is a microorganism.

Preferably, the microorganism is a microorganism disclosed in Table 1.

Preferably, the microorganism is selected from the group consisting of *Salmonella; Salmonella enterica; Listeria*, preferably, *Listeria monocytogenes; S. aureus; E. coli*; carbapenem-resistant bacteria, preferably *Pseudomonas aeruginosa*, and *Klebsiella pneumonia; Campylobacter jejuni; C. coli; C. lari; Bacillus; Staphylococcus; Clostridium; Mycobacterium tuberculosis; Clostridium perfringens; S. agalactiae, Candida* spp.; Gram negative bacteria, yeast, molds, *Pseudomonas aeruginosa*, Enterococci, *Streptococcus pyogenes; Citrobacter, Coliform; Cronobacter sakazakii;* MRSA, VRE, *Geobacillus stearothermophilus; Listeria* spp., ESBL producing enterobacteria; *Vibrio; Clostridium difficile; Candida albicans; Prevotella; Shigella*, a microorganism containing apyrase, preferably *Shigella; Legionella* pneumophilia; and a virus of the Caliciviridae family, preferably a Lagovirus, a Norovirus, a Sapovirus, a Nebovirus, a Recovirus, more preferably a Norovirus.

Preferably, the microorganism is selected from the group consisting of *Salmonella, Salmonella enterica, Listeria*, preferably, *Listeria monocytogenes, S. aureus, E. coli*, and carbapenem-resistant bacteria, preferably *Pseudomonas aeruginosa* and *Klebsiella pneumonia*.

Preferably, less than 0.1 µg of the compound of Formula I are added in step b), more preferably, less than 0.09 µg, even more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Preferably, the compound added to the medium in step b) is present in DMSO solution. In this case, the total amount of the compound of Formula I added in step b) can simply be determined by means of aliquotation from a stock solution of a known concentration.

Preferably, the final concentration of the compound in the medium after step b) is 2-50 µM, preferably 2-40 µM, more preferably 2-30 µM, more preferably 5-20 µM, more preferably 8-15 µM, even more preferably 9-11 µM, most preferably about µM.

Preferably, the microorganism is a pathogenic microorganism, more preferably a bacterium, even more preferably *Salmonella, Listeria* or *S. aureus*.

According to a preferred embodiment, the microorganism is *Salmonella*, preferably *Salmonella enterica*, and the compound is a compound of Formula II:

(Formula II)

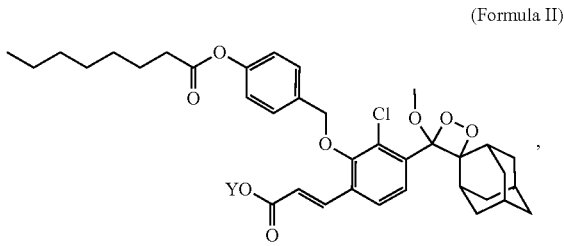

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl.

According to a particularly preferred embodiment, the microorganism is *Salmonella*, preferably *Salmonella enterica*, and the compound is a compound of Formula IIa.

According to another preferred embodiment, the microorganism is *Listeria*, preferably *Listeria monocytogenes*, and the compound is a compound of Formula III:

(Formula III)

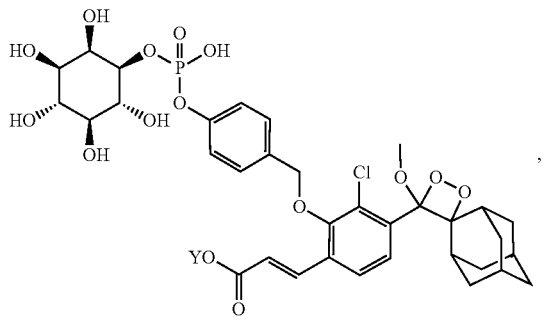

(Formula V)

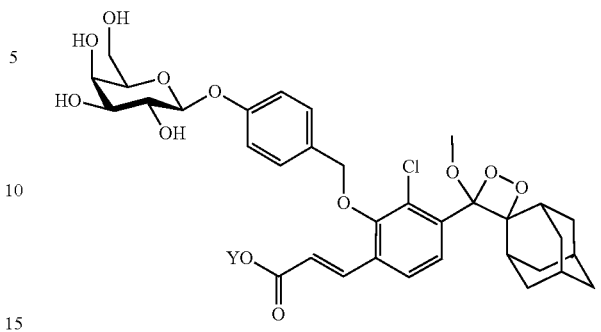

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl.

According to a particularly preferred embodiment, the microorganism is *Listeria*, preferably *Listeria monocytogenes*, and the compound is a compound of Formula IIIa or IIIb, preferably IIIb.

According to another preferred embodiment, the microorganism is *S. aureus* and the compound is a compound of Formula IV:

(Formula IV)

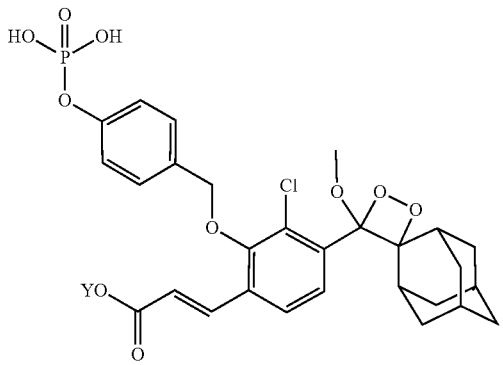

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl.

According to a particularly preferred embodiment, the microorganism is *S. aureus* and the compound is a compound of Formula IVa.

According to another preferred embodiment, the microorganism is *E. coli* and the compound is a compound of Formula V:

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl.

According to a particularly preferred embodiment, the microorganism is *E. coli* and the compound is a compound of Formula Va or Vb, preferably Vb.

According to another preferred embodiment, the microorganism are carbapenem-resistant bacteria, preferably *Pseudomonas aeruginosa* and *Klebsiella pneumonia*, and the compound is a compound of Formula VII or VIII (Compound VII)

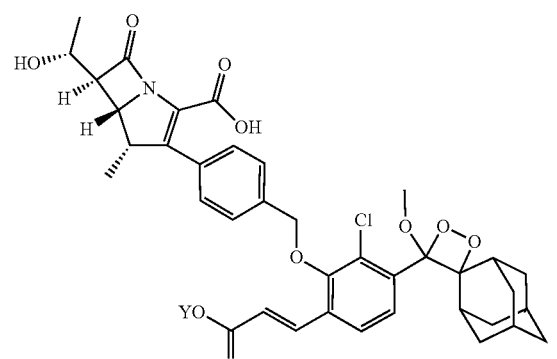

(Compound VIII)

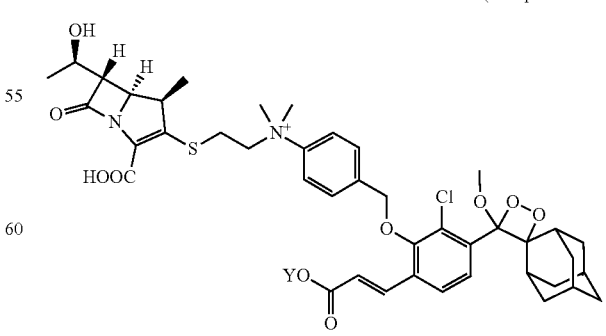

wherein Y is —H, an optionally substituted $C_1$-$C_{12}$ alkyl or an alkali metal ion, wherein the alkali metal ion is preferably sodium or potassium and the optionally substituted $C_1$-$C_{12}$ alkyl is preferably methyl, ethyl, propyl, isopropyl, butyl, isobutyl, or tert-butyl. Preferably, Y is —H, or an optionally substituted $C_1$-$C_{12}$ alkyl, wherein the optionally substituted $C_1$-$C_{12}$ alkyl is preferably methyl, ethyl, propyl, isopropyl, butyl, isobutyl, or tert-butyl. More preferably, Y is —H or methyl.

According to a particularly preferred embodiment, the microorganisms are carbapenem-resistant *Pseudomonas aeruginosa* and *Klebsiella pneumonia* and the compound is a compound of Formula VIIa, VIIb or VIIIa, preferably VIIIa.

Further target analytes/target microorganisms/target metabolites as well as specific compounds of Formula I, in particular groups $R^1$, suitable for their detection are discernible from the first aspect of the invention Moreover, it is preferred that the medium comprises more than one microorganism and one of said microorganisms leads to an at least 10-fold, preferably at least 20-fold, higher light emission than one or more other ones of said microorganisms present in the medium.

In a third aspect, which may be considered a sub-aspect of the second aspect, the present invention relates to the use of a compound of Formula I as described in the first aspect for the detection of growth substrates, nutrients, and/or metabolites by enzymatic oxidation of said growth substrates, nutrients, and metabolites.

The detection of growth substrates, nutrient and metabolites allows for the indirect detection of pathogens.

In this aspect, the growth substrates, nutrients, and/or metabolites are detected by contacting them with an enzyme that oxidizes the growth substrates, nutrients, and/or metabolites and thereby produces hydrogen peroxide. Thus, the growth substrates, nutrients, or metabolites are indirectly detected by detecting the hydrogen peroxide produced by an enzyme acting on the growth substrates, nutrients, or metabolites.

In one embodiment, the nutrient is a carbohydrate or an amino acid and the enzyme is a corresponding oxidase. For example, the nutrient is glucose and the enzyme is glucose oxidase; or the nutrient is a D-amino acid and the enzyme is D-amino acid oxide (DAO); or the nutrient is D-aspartic acid and the enzyme is D-aspartate oxidase.

In a preferred embodiment, the metabolite is histamine and the enzyme is diaminooxidase.

In this aspect, $R^1$ is preferably —B(Z)(Z') or —$BF_3^-Kat^+$ as defined in the first aspect and the other substituents are also as defined in the first aspect.

In one embodiment, n is 0. In another embodiment, n is 1.

Particularly preferred compounds are those disclosed in Table A, wherein $R^1$ is

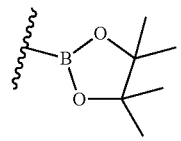

The compound of Formula I can be used solid form or in solution. However, using the compound of Formula I in solution, preferably DMSO solution, is preferred for the reasons set out above. Preferably, the compound of Formula I is used in an amount of less than 0.1 µg, preferably less than 0.09 µg, more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

According to a preferred embodiment, the compound is used in a final concentration of 1 to 100 µM, preferably 5 to 80 µM, more preferably 10 to 70 µM, more preferably 20 to 60 µM, more preferably 30 to 50 µM, even more preferably 35 to 45 µM.

According to another preferred embodiment the compound is used in a final concentration of 10 to 500 µM, preferably 10 to 250 µM, more preferably 10 to 50 µM.

Preferably, the medium is a prokaryotic cell-comprising medium, a prokaryotic culture supernatant, an eukaryotic cell-comprising medium, an eukaryotic culture supernatant, blood serum or whole blood.

Further, the present invention relates to a method for the detection of growth substrates, nutrients, and/or metabolites by enzymatic oxidation of said growth substrates, nutrients, and metabolites.

The method comprises the steps of a) providing a medium comprising a growth substrate, nutrient, and/or metabolite capable of being oxidized by an enzyme, b) (b1) adding an enzyme capable of oxidizing the growth substrate, nutrient, and/or metabolite and thereby producing hydrogen peroxide, (b2) adding a compound of Formula I, wherein $R^1$ is —B(Z)(Z') and the other substituents are described in the first aspect, to the medium so that the compound of Formula I emits light upon contact with hydrogen peroxide, wherein steps (b1) and (b2) may be performed simultaneously or subsequently, and c) detecting the emitted light.

Preferably, the medium is an aqueous medium.

More preferably, the medium is a prokaryotic cell-comprising medium, a prokaryotic culture supernatant, an eukaryotic cell-comprising medium, an eukaryotic culture supernatant, blood serum or whole blood.

In one embodiment, the nutrient is a carbohydrate or an amino acid and the enzyme is a corresponding oxidase. For example, the nutrient is glucose and the enzyme is glucose oxidase; or the nutrient is a D-amino acid and the enzyme is D-amino acid oxide (DAO); or the nutrient is D-aspartic acid and the enzyme is D-aspartate oxidase.

In a preferred embodiment, the metabolite is histamine and the enzyme is diaminooxidase.

Ethanol or another suitable solvent or solvent mixture, preferably in an amount of 15%, may be added in any of steps a) and b) (including substeps b1 and b2) or between or after steps a) and b). As described above, other lysis reagents may alternatively be used.

The compound of Formula I can be used in solid form or in solution. However, using the compound of Formula I in solution, preferably DMSO solution, is preferred for the reasons set out above.

Preferably, the compound of Formula I is added in an amount of less than 0.1 µg, preferably less than 0.09 µg, more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Preferably, the compound of Formula I is added such that the final concentration of the compound in the medium is 2-50 µM, preferably 2-40 µM, more preferably 2-30 µM, more preferably 5-20 µM, more preferably 8-15 µM, even more preferably 9-11 µM, most preferably about 10 µM.

Alternatively, and also preferably, the compound of Formula I is added such that the final concentration of the compound in the medium is 1 to 100 µM, preferably to 80

μM, more preferably 10 to 70 μM, more preferably 20 to 60 μM, more preferably 30 to 50 μM, even more preferably 35 to 45 μM.

In a fourth aspect, which may be considered a sub-aspect of the second aspect, the present invention relates to the use of a compound of Formula I as defined in the first aspect for the detection of bacterial endotoxins via detection of limulus Factor C.

In this aspect, group $R^1$ is responsive/labile towards limulus Factor C. Preferably, $R^1$ is Boc-Val-Pro-Argininyl or Boc-Asp(OBzl)-Pro-Argininyl and the other substituents are as defined in the first aspect.

The compound of Formula may be used in solid form or in solution, preferably DMSO solution. Preferably, the compound of Formula I is used in solution, preferably in DMSO solution.

Preferably, the compound of Formula I is used in an amount of less than 0.1 μg, preferably less than 0.09 μg, more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Further, the present invention relates to a method for the detection of bacterial endotoxins via detection of limulus factor C, wherein a compound of Formula I and limulus factor C are added to an endotoxin-comprising medium.

Preferably, $R^1$ is Boc-Val-Pro-Argininyl or Boc-Asp (OBzl)-Pro-Argininyl and the other substituents are as defined in the first aspect. Particularly preferably, the compound is a compound of Formula I as disclosed in Table A, wherein $R^1$ is Boc-Val-Pro-Argininyl or Boc-Asp(OBzl)-Pro-Argininyl.

In the presence of a respective endotoxin, the peptidase activity of limulus factor C is activated and this peptidase activity cleaves $R^1$ from the remainder part of the compound of Formula I resulting in chemiluminescence. In the absence of the respective endotoxin, there is no peptidase activity.

Preferably, the medium used in the method is an aqueous medium.

Ethanol or another suitable solvent or solvent mixture, preferably in an amount of 15%, may be added to the medium. As described above, other lysis reagents may alternatively be used.

The compound of Formula I can be used solid form or in solution. However, using the compound of Formula I in solution, preferably DMSO solution, is preferred for the reasons set out above.

Preferably, the compound of Formula I is used in an amount of less than 0.1 μg, preferably less than 0.09 μg, more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Preferably, the final concentration of the compound of Formula I in the medium is 2-50 μM, preferably 2-40 μM, more preferably 2-30 μM, more preferably 5-20 μM, more preferably 8-15 μM, even more preferably 9-11 μM, most preferably about 10 μM.

In a fifth aspect, which may be considered a sub-aspect of the second aspect, the present invention relates to the use of a compound of Formula I as described in the first aspect for testing of pasteurization of dairy products, e.g. milk.

Preferably, the used compound is a compound of Formula I, wherein $R^1$ is phosphoryl and the other substituents are as described in the first aspect.

Preferably, the compound of Formula I is used in an amount of less than 0.1 μg, preferably less than 0.09 μg, more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Preferably, the compound is used in a final concentration of 1 to 100 μM, preferably 5 to 80 μM, more preferably 10 to 70 μM, more preferably 20 to 60 μM, more preferably 30 to 50 μM, even more preferably 35 to 45 μM.

In another embodiment, the compound of Formula I is used in a final concentration of 1 to 50 μM, preferably 5 to 40 μM, more preferably 10 to 30 μM, more preferably 15 to 25 μM, more preferably 18 to 22 μM, more preferably 19 to 21 μM.

Further, the present invention relates to a method of testing pasteurization of dairy products, preferably milk.

The method comprises the steps of a) providing a dairy product medium, preferably milk, b) pasteurization, c) adding a compound of Formula I as described in the first embodiment, wherein $R^1$ is phosphoryl, to the medium, optionally in combination with a buffer, so that the compound of Formula I emits light, and d) detecting the emitted light.

Phosphatase, which is naturally present in a dairy product, degrades during sterilization. Thus, if sterilization is successful, no light emission is detected as no active phosphatase is present in the dairy product.

Preferably, the compound added to the medium in step b) is present in DMSO solution.

Preferably, the compound of Formula I is added to the medium such that it is present in a final concentration of 2-50 μM, preferably 2-40 μM, more preferably 2-30 μM, more preferably 5-20 μM, more preferably 8-15 μM, even more preferably 9-11 μM, most preferably about 10 μM.

In another embodiment, the compound of Formula I is added to the medium such that it is present in a final concentration of 1 to 50 μM, preferably 5 to 40 μM, more preferably 10 to 30 μM, more preferably 15 to 25 μM, more preferably 18 to 22 μM, more preferably 19 to 21 μM.

Preferably, less than 0.1 μg of the compound of Formula I are added to the medium, more preferably, less than 0.09 μg, even more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Preferably, the compound added to the medium in step b) is present in DMSO solution. In this case, the total amount of the compound of Formula I added in step b) can simply be determined by means of aliquotation from a stock solution of a known concentration.

In a sixth aspect, which may be considered a sub-aspect of the second aspect, the present invention relates to the use of a compound of Formula I for testing antibiotic resistance in microorganisms.

Preferably, $R^1$ is a beta-lactamase-labile group as defined in the first aspect, preferably a beta-lactam antibiotic, more preferably a penicillin, a cephalosporin of generation 1 to 5, a cephamycin, or a carbapenem, and the other substituents are as defined in the first aspect.

Preferably, the compound of Formula I is as defined in Table A, wherein $R^1$ is the preferred depicted carbapenem moiety.

Preferably, the microorganism is selected from the group consisting of *Salmonella; Salmonella enterica; Listeria*, preferably, *Listeria monocytogenes; S. aureus; E. coli*; carbapenem-resistant bacteria, preferably *Pseudomonas aeruginosa*, and *Klebsiella pneumonia; Campylobacter jejuni; C. coli; C. lari; Bacillus; Staphylococcus;*

*Clostridium; Mycobacterium tuberculosis; Clostridium perfringens; S. agalactiae, Candida* spp.; Gram negative bacteria, yeast, molds, *Pseudomonas aeruginosa*, Enterococci, *Streptococcus pyogenes; Citrobacter, Coliform; Cronobacter sakazakii*; MRSA, VRE, *Geobacillus stearothermophilus; Listeria* spp., ESBL producing enterobacteria; *Vibrio; Clostridium difficile; Candida albicans; Prevotella; Shigella, Legionella* pneumophilia; and a virus of the Caliciviridae family, preferably a Lagovirus, a Norovirus, a Sapovirus, a Nebovirus, a Recovirus, more preferably a Norovirus.

More preferably, the microorganism is selected from the group consisting of *Salmonella; Salmonella enterica; Listeria*, preferably, *Listeria monocytogenes; S. aureus; E. coli*; carbapenem-resistant bacteria, preferably *Pseudomonas aeruginosa*, and *Klebsiella pneumonia; Campylobacter jejuni; C. coli; C. lari; Bacillus; Staphylococcus; Clostridium; Mycobacterium tuberculosis; Clostridium perfringens; S. agalactiae, Candida* spp.; Gram negative bacteria, yeast, molds, *Pseudomonas aeruginosa*, Enterococci, *Streptococcus pyogenes; Citrobacter, Coliform; Cronobacter sakazakii*; MRSA, VRE, *Geobacillus stearothermophilus; Listeria* spp., ESBL producing enterobacteria; *Vibrio; Clostridium difficile; Candida albicans; Prevotella; Shigella*, and *Legionella pneumophilia;*

Even more preferably, the microorganisms are selected from *Pseudomonas aeruginosa* and *Klebsiella pneumoniae*.

The compound may be used in solid form or in solution. However, using the compound of Formula I in solution, preferably DMSO solution, is preferred.

Preferably, the compound of Formula I is used in an amount of less than 0.1 μg, preferably less than 0.09 μg, more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Preferably, the compound is used in a final concentration of 1 to 100 μM, preferably 5 to 80 μM, more preferably 10 to 70 μM, more preferably 20 to 60 μM, more preferably 30 to 50 μM, even more preferably 35 to 45 μM.

In another embodiment, the compound is used in a final concentration of about 1 to 50 μM, preferably 2 to 40 μM, more preferably 3 to 30 μM, more preferably 4 to 20 μM, more preferably 5 to 15 μM, more preferably 7 to 13 μM, more preferably 9 to 11 μM.

Further, the present invention relates to a method for testing of antibiotic, in particular beta-lactam antibiotic such as a penicillin, a cephalosporin, a cephamycin, or a carbapenem, resistance in microorganisms.

The method comprises the steps of a) providing a medium comprising one or more microorganisms b) adding a compound of Formula I, wherein $R^1$ is a beta-lactamase-labile group, preferably a beta-lactam antibiotic such as a penicillin, a cephalosporin of generation 1 to 5, a cephamycin, or a carbapenem and the other substituents are as defined in the first aspect, to the medium so that the compound of Formula I emits light when antibiotic, preferably a beta-lactam antibiotic such as a penicillin, a cephalosporin, a cephamycin or a carbapenem, resistant microorganisms are present in the medium, and c) detecting the emitted light.

Preferably, the compound of Formula I is as defined in Table A, wherein $R^1$ is carbapenemyl.

Preferably, the medium is an aqueous medium.

Ethanol or another suitable solvent or solvent mixture, preferably in an amount of 15%, may be added in any of steps a) and b) or between or after steps a) and b). As described above, other lysis reagents may alternatively be used.

Preferably, the compound of Formula I is added to the medium such that it is present in a final concentration of 2-50 μM, preferably 2-40 μM, more preferably 2-30 μM, more preferably 5-20 μM, more preferably 8-15 μM, even more preferably 9-11 μM, most preferably about 10 μM.

In another embodiment, the compound of Formula I is added to the medium such that it is present in a final concentration of 1 to 50 μM, preferably 2 to 40 μM, more preferably 3 to 30 μM, more preferably 4 to 20 μM, more preferably 5 to 15 μM, more preferably 7 to 13 μM, more preferably 9 to 11 μM.

Preferably, less than 0.1 μg of the compound of Formula I are added to the medium, more preferably, less than 0.09 μg, even more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

Preferably, the compound added to the medium in step b) is present in DMSO solution. In this case, the total amount of the compound of Formula I added in step b) can simply be determined by means of aliquotation from a stock solution of a known concentration.

In particular, the method is suitable for distinguishing antibiotic resistant microorganisms from antibiotic sensitive microorganisms as light emission will only occur for antibiotic resistant microorganisms.

In a seventh aspect, which may be considered a sub-aspect of the second aspect, the present invention relates to the use of a compound of Formula I for the detection of inorganic phosphate, preferably inorganic phosphate produced by enzymatic reactions.

Preferably, $R^1$ is oxalylester and the other substituents are as defined in the first aspect.

Preferably, the inorganic phosphate is produced by apyrase, preferably *Shigella* apyrase. In this case, the compound is suitable for detecting *Shigella*, one of the leading bacterial causes of diarrhea worldwide.

Preferably, the compound of Formula I is used in an amount of less than 0.1 μg, preferably less than 0.09 μg, more preferably less than 0.08 μg, even more preferably less than 0.07 μg, even more preferably less than 0.065 μg, even more preferably 0.04 to 0.06 μg, even more preferably 0.045 to 0.055 μg, most preferably about 0.05 μg.

The compound may be used in in solid form or in solution. However, using the compound of Formula I in solution, preferably DMSO solution, is preferred.

Preferably, the compound is used in a final concentration of 1 to 100 μM, preferably 5 to 80 μM, more preferably 10 to 70 μM, more preferably 20 to 60 μM, more preferably 30 to 50 μM, even more preferably 35 to 45 μM.

Further, the present invention relates to a method for detecting inorganic phosphate, preferably inorganic phosphate produced by enzymatic reactions.

The method comprises the steps of a) providing a medium comprising inorganic phosphate b) adding a compound of Formula I, wherein $R^1$ is oxalylester and the other substituents are as defined in the first aspect, to the medium so that the compound of Formula I emits light, and c) detecting the emitted light.

Preferably, the compound of Formula I is as defined in Table A, wherein $R^1$ is oxalylester.

Preferably, the inorganic phosphate comprised in the medium is produced by apyrase, preferably *Shigella* apyrase. Thus, it is preferred that the medium in step a)

comprises apyrase, preferably *Shigella* apyrase. It is particularly preferred that the medium in step a) comprises *Shigella*.

Preferably, the medium is an aqueous medium.

Ethanol or another suitable solvent or solvent mixture, preferably in an amount of 15%, may be added in any of steps a) and b) or between or after steps a) and b). As described above, other lysis reagents may alternatively be used.

Preferably, less than 0.1 µg of the compound of Formula I are, more preferably, less than 0.09 µg, even more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Preferably, the compound added to the medium in step b) is present in DMSO solution.

Preferably, the final concentration of the compound in the medium is 2-50 µM, preferably 2-40 µM, more preferably 2-30 µM, more preferably 5-20 µM, more preferably 8-15 µM, even more preferably 9-11 µM, most preferably about 10 µM.

In an eigths aspect, which may be considered a sub-aspect of the second aspect, the present invention relates to the use of a compound of Formula I for monitoring of a sterilization process, preferably through detection of alpha-D-glucosidase activity of the indicator microorganism *Geobacillus stearothermophilus*. *Geobacillus stearothermophilus* produces alpha-glucosidase, which, however, is inactivated upon sterilization.

Preferably, $R^1$ is alpha-D-glucopyranosidyl and the other substituents are as defined in the first aspect. Thus, if the *Geobacillus stearothermophilus* and alpha-glucosidase are inactivated due to sterilization, it is not able to cleave off the alpha-D-glucopyranosidyl moiety and, consequently, no light is emitted.

Preferably, the compound of Formula I is used in an amount of less than 0.1 µg, preferably less than 0.09 µg, more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Also in this aspect, the compound of Formula I may be used in solid form or in solution. However, using the compound of Formula I in solution, preferably DMSO solution, is preferred.

Preferably, the compound is used in a final concentration of 1 to 100 µM, preferably 5 to 80 µM, more preferably 10 to 70 µM, more preferably 20 to 60 µM, more preferably 30 to 50 µM, even more preferably 35 to 45 µM.

Further, the present invention relates a method for monitoring of a sterilization process, preferably through detection of alpha-D-glucosidase activity of the indicator microorganism *Geobacillus stearothermophilus*.

The method comprises the steps of a1) providing a medium comprising a microorganism that, under normal conditions, produces alpha-glucosidase, preferably *Geobacillus stearothermophilus*, a2) sterilizing the medium, b) adding a compound of Formula I, wherein $R^1$ is alpha-D-glucopyranosidyl and the other substituents are as defined in the first aspect, to the medium and c) detecting the emitted light, if any.

Preferably, the compound of Formula I is as defined in Table A, wherein $R^1$ is alpha-D-glucopyranosidyl and the other substituents are as defined in the first aspect.

Preferably, the medium is an aqueous medium.

Ethanol or another suitable solvent or solvent mixture, preferably in an amount of 15%, may be added in or after step b). As described above, other lysis reagents may alternatively be used.

Preferably, less than 0.1 µg of the compound of Formula I are, more preferably, less than 0.09 µg, even more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Preferably, the compound added to the medium is present in DMSO solution.

Preferably, the final concentration of the compound in the medium is 2-50 µM, preferably 2-40 µM, more preferably 2-30 µM, more preferably 5-20 µM, more preferably 8-15 µM, even more preferably 9-11 µM, most preferably about 10 µM.

In a ninth aspect, which may be considered a sub-aspect of the second aspect, the present invention relates to the use of a compound of Formula I as described in the first aspect for endpoint and online detection of antibiotic resistance of bacteria and for antibiotic susceptibility testing.

In this aspect, the compound may be added to a bacteria- and antibiotic-containing medium at the beginning of cultivation or at the time of measurement. Antibiotic resistant bacteria will multiply even in the presence of the antibiotic, which will lead to light emission of the compound of Formula I by means of interaction of group $R^1$ with the respective bacteria (in particular an enzyme or the like thereof) (cf., Example 8).

Which group $R^1$ may be used for said endpoint and online detection of antibiotic resistance of bacteria and for antibiotic susceptibility testing, is discernible from Table 1. For example, a compound of Formula I, wherein $R^1$ is phosphoryl, may be used for endpoint and online detection of antibiotic resistance of *Staphylococcus aureus*, in particular MRSA, *Clostridium perfringens, S. agalactiae,* or *Candida* and for antibiotic susceptibility testing thereof. In another example, a compound of Formula I, wherein $R^1$ is L-pyroglutamic acidyl, may be used for endpoint and online detection of antibiotic resistance of Enterococci, *Streptococcus pyogenes,* or *Citrobacter* and for antibiotic susceptibility testing thereof. In a further example, a compound of Formula I, wherein $R^1$ is beta-D-galactopyranosidyl, may be used for endpoint and online detection of antibiotic resistance of *Coliform,* or *E. coli* and for antibiotic susceptibility testing thereof.

Preferably, the compound of Formula I is used in an amount of less than 0.1 µg, preferably less than 0.09 µg, more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Also in this aspect, the compound of Formula I may be used in solid form or in solution. However, using the compound of Formula I in solution, preferably DMSO solution, is preferred.

Preferably, the compound is used in a final concentration of 1 to 100 µM, preferably 5 to 80 µM, more preferably 10 to 70 µM, more preferably 20 to 60 µM, more preferably 30 to 50 µM, even more preferably 35 to 45 µM.

Further, the present invention relates a method for endpoint and online detection of antibiotic resistance of bacteria and for antibiotic susceptibility testing.

The method comprises the steps of a) providing a medium comprising a microorganism, preferably bacteria, b) adding an antibiotic, c) adding a compound of Formula I, wherein R[1] is responsive towards said microorganism, in particular an enzyme produced thereby, wherein step c) may be performed before, together with or after step b), d) detecting the emitted light, if any.

Which group R[1] may be used for said endpoint and online detection of antibiotic resistance of bacteria and for antibiotic susceptibility testing, is discernible from Table 1.

Preferably, less than 0.1 µg of the compound of Formula I are, more preferably, less than 0.09 µg, even more preferably less than 0.08 µg, even more preferably less than 0.07 µg, even more preferably less than 0.065 µg, even more preferably 0.04 to 0.06 µg, even more preferably 0.045 to 0.055 µg, most preferably about 0.05 µg.

Preferably, the compound added to the medium is present in DMSO solution.

Preferably, the final concentration of the compound in the medium is 2-50 µM, preferably 2-40 µM, more preferably 2-30 µM, more preferably 5-20 µM, more preferably 8-15 µM, even more preferably 9-11 µM, most preferably about 10 µM.

Preferably, the medium is an aqueous medium.

Ethanol or another suitable solvent or solvent mixture, preferably in an amount of 15%, may be added in or after step b). As described above, other lysis reagents may alternatively be used.

The present invention will now be further illustrated by the following, non-limiting example.

EXAMPLES

General Methods:

All reactions were carried out at room temperature unless stated otherwise. Chemicals and solvents were either A.R. grade or purified by standard techniques. Thin layer chromatography (TLC): silica gel plates Merck 60 F254: compounds were visualized by irradiation with UV light. Column chromatography (FC): silica gel Merck 60 (particle size 0.040-0.063 mm), eluent given in parentheses. Reverse-phase high pressure liquid chromatography (RP-HPLC): C18 5u, 250×4.6 mm, eluent given in parentheses. Preparative RP-HPLC: C18 5u, 250×21 mm, eluent given in parentheses. Fluorescence and chemiluminescence were recorded on Molecular Devices Spectramax i3x.

If not stated otherwise, all chemicals were purchased from Merck and Biosynth AG and used as received.

Abbreviations. AcOH—Acetic acid, MeCN—Acetonitrile, DCM—Dichloromethane, DMF—N,N'-Dimethylformamide, EtOAc—Ethylacetate, Hex—Hexanes, MeOH—Methanol, TFA—Trifluoroacetic acid, THF—Tetrahydrofuran. TIPSCI—Triisopropylsilyl chloride.

Synthesis Example 1: Synthesis of Compound IIa

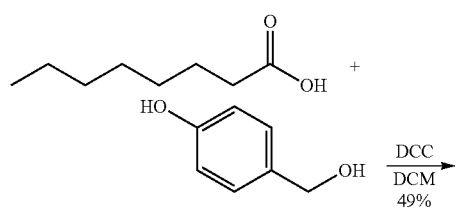

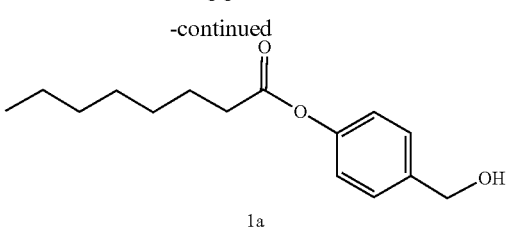

DCC (457 mg, 2.21 mmol, 1.1 eq) was added to a mixture of octanoic acid (350 µl, 2.21 mmol, 1.1 eq) and 4-hydroxybenzyl alcohol (250 mg, 2.01 mmol, 1 eq) in DCM (2 ml). Reaction mixture was stirred at room temperature and monitored via TLC (40:60 EtOAc:Hex). Upon completion, the DCC was filtered off and the crude product was purified by column chromatography on silica gel (30:70 EtOAc:Hex) to afford the compound 1a (246 mg, 49% yield) as a yellowish solid. $^1$H NMR (400 MHz, CDCl$_3$) δ 7.35 (d, J=8.5 Hz, 2H), 7.05 (d, J=8.5 Hz, 2H), 4.63 (s, 2H), 2.55 (t, J=7.5 Hz, 2H), 1.76 (dt, J=15.1, 7.5 Hz, 2H), 1.50-1.18 (m, 8H), 0.97-0.82 (m, 3H). $^{13}$C NMR (101 MHz, CDCl$_3$) δ 173.75, 150.68, 133.71, 129.49, 121.78, 65.50, 34.48, 31.72, 29.16, 29.14, 29.11, 28.98, 25.01, 22.67, 14.13.

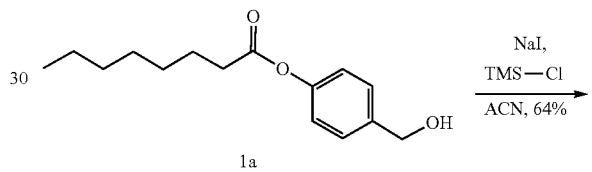

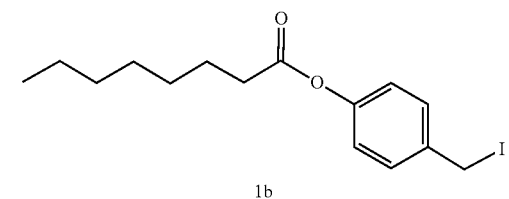

Compound 1a (200 mg, 0.8 mmol, 1 eq) was dissolved in 4 ml of ACN and cooled to 0° C. Sodium Iodide (360 mg, 2.4 mmol, 3 eq) was added followed by the rapid addition of TMS-Cl (306 µl, 2.4 mmol, 3 eq). The reaction was allowed to warm up to room temperature and monitored by TLC (30:70 EtOAc:Hex). Upon completion, the reaction mixture was diluted with EtOAc, and washed with saturated Na$_2$S$_2$O$_3$ followed by brine. The organic layer was separated, dried over Na$_2$SO$_4$, filtered and the solvent was evaporated under reduced pressure, to afford compound 1b (185 mg, 64% yield) as an off-white solid. The compound was reacted without further purification. $^1$H NMR (400 MHz, CDCl$_3$) 7.38 (d, J=8.0 Hz, 2H), 7.00 (d, J=8.0 Hz, 2H), 4.45 (s, 2H), 2.54 (t, J=5.6 Hz, 2H), 1.74 (dt, J=15.1, 7.5 Hz, 2H), 1.44-1.24 (m, 8H), 0.90 (t, J=6.9 Hz, 3H). $^{13}$C NMR (101 MHz, CDCl$_3$) δ 172.35, 150.33, 133.73, 129.82, 129.40, 121.93, 121.68, 43.20, 34.36, 34.28, 31.62, 30.71, 29.03, 28.88, 24.90, 22.57, 14.04.

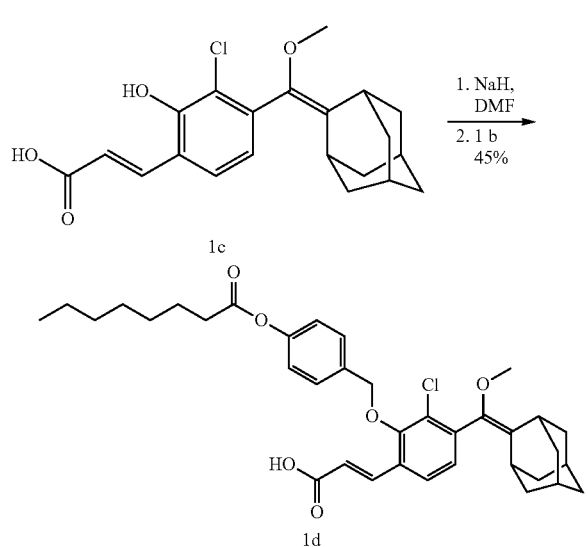

Compound 1c (prepared in accordance with Green, O., Eilon, T., Hananya, N., Gutkin, S., Bauer, C R., Shabat, D., *ACS Central* Sci., 2017, 4, 349-58) (30 mg, 0.08 mmol, 1.1 eq) was dissolved in dry DMF, under argon atmosphere and cooled to 0° C. Sodium hydride (6.4 mg, 0.16 mmol, 2.2 eq) was added, and the reaction was allowed to warm to room temperature. After stirring for 15 minutes, compound 1b (26 mg, 0.07 mmol, 1 eq) was added and the reaction was monitored by RP-HPLC (90-100% ACN in water, 20 min). Upon completion, the reaction mixture was concentrated by evaporation under reduced pressure and the crude product was purified by preparative RP-HPLC (95-100% ACN in water, 20 min) to afford compound 1d (18 mg, 45% yield) as a white solid. $^1$H NMR (400 MHz, DMSO) δ 7.78 (d, J=2.3 Hz, 1H), 7.75 (d, J=10.5 Hz, 1H), 7.48 (d, J=8.5 Hz, 1H), 7.17-7.05 (m, 3H), 6.58 (d, J=16.1 Hz, 1H), 4.96 (d, J=12.9 Hz, 2H), 3.21 (s, 3H), 3.17 (s, 2H), 2.56 (t, J=7.4 Hz, 2H), 1.92 (dd, J=34.0, 9.0 Hz, 4H), 1.82-1.55 (m, 10H), 1.37-1.14 (m, 8H), 0.89-0.80 (m, 3H). $^{13}$C NMR (101 MHz, DMSO) δ 172.09, 159.35, 153.04, 150.78, 139.79, 137.52, 133.86, 130.71, 130.06, 129.93, 129.00, 128.20, 126.30, 122.28, 75.34, 56.92, 36.88, 33.89, 32.83, 31.53, 29.46, 28.78, 28.12, 27.98, 24.75, 22.51, 14.31.

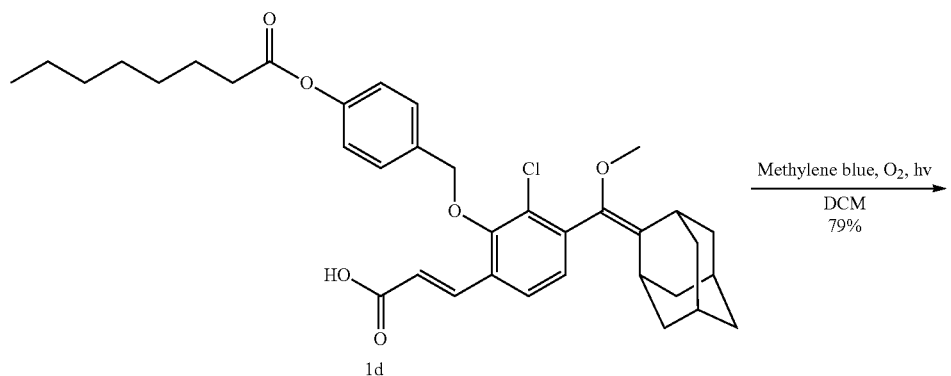

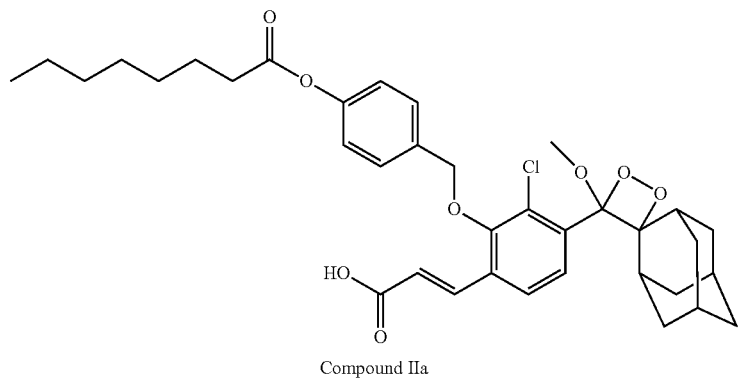

Compound IIa

Compound 1d (18 mg, 0.03 mmol) and few milligrams of methylene blue were dissolved in 5 ml of DCM and a few drops of DMF (to enhance solubility). Oxygen was bubbled through the solution while irradiating with yellow light. The reaction was monitored by RP-HPLC (90-100% ACN in water, 20 min). Upon completion, the reaction mixture was concentrated by evaporation under reduced pressure. The crude product was purified by preparative RP-HPLC (90-100% ACN in water, 20 min) to afford Compound IIa (15 mg, 79% yield) as an off-white solid. $^1$H NMR (400 MHz, DMSO) δ 7.94 (d, J=8.4 Hz, 1H), 7.79 (d, J=8.4 Hz, 1H), 7.73 (d, J=16.1 Hz, 1H), 7.49 (d, J=8.5 Hz, 2H), 7.13 (d, J=8.5 Hz, 2H), 6.63 (d, J=16.1 Hz, 1H), 4.92 (q, J=10.9 Hz, 2H), 3.11 (s, 3H), 2.88 (s, 1H), 2.56 (t, J=7.4 Hz, 2H), 2.22 (d, J=11.5 Hz, 1H), 1.89 (d, J=3.8 Hz, 1H), 1.77-1.50 (m, 19H), 1.46 (d, J=11.8 Hz, 1H), 1.40-1.16 (m, 8H), 0.90-0.80 (m, 3H). $^{13}$C NMR (126 MHz, DMSO) δ 172.35, 167.74, 154.08, 151.18, 136.97, 134.67, 133.84, 132.01, 130.34, 129.10, 127.38, 126.70, 123.90, 122.50, 111.79, 96.02, 75.65, 50.03, 36.48, 34.07, 33.89, 33.68, 32.44, 32.26, 31.71, 31.48, 30.43, 29.60, 26.10, 25.77, 22.64, 14.54.

Synthesis Example 2: Synthesis of Compound IIIa

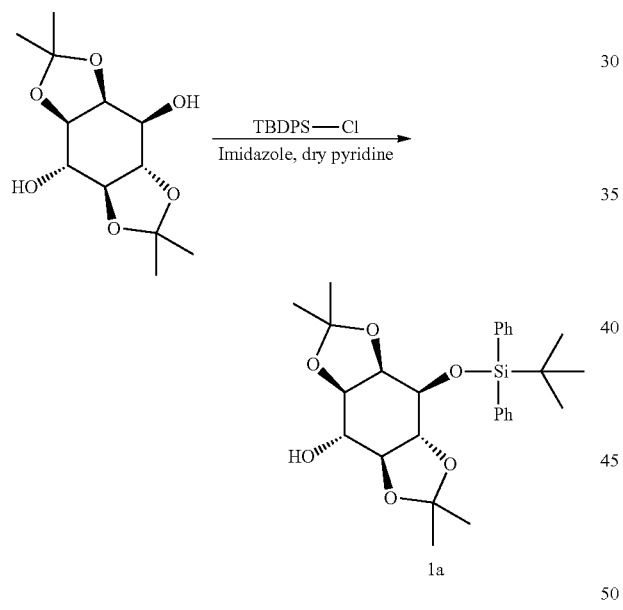

1,2:4,5-Di-O-isopropylidene-myo-inositol (250 mg, 0.96 mmol, 1 eq) and Imidazole (98 mg, 1.44 mmol, 1.5 eq) were dissolved in dry pyridine (3 ml) and cooled to −10° C. t-Butyldiphenylsilyl chloride (275 μl, 1.06 mmol, 1.1 eq) was added slowly via syringe. The reaction was allowed to warm up to room temperature and monitored via TLC (50:50 EtOAc:Hex). Upon completion, the reaction mixture was diluted with EtOAc, and washed with saturated NH$_4$Cl. The organic layer was separated, dried over Na$_2$SO$_4$, filtered and the solvent was evaporated under reduced pressure. The crude product was purified by column chromatography on silica gel (50:50 EtOAc:Hex) to afford the compound 1a (350 mg, 73% yield) as a white foam. MS (ES+): m/z calc. for C$_{28}$H$_{38}$O$_6$Si: 498.24; found: 499.4 [M+H]$^+$.

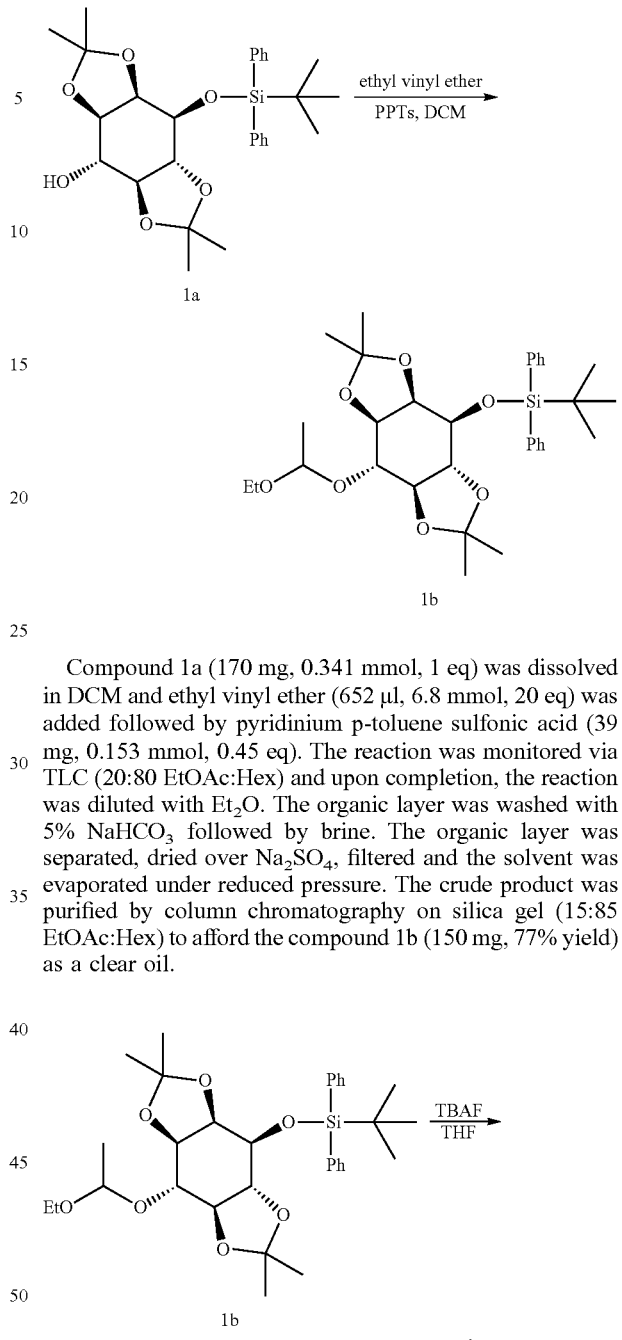

Compound 1a (170 mg, 0.341 mmol, 1 eq) was dissolved in DCM and ethyl vinyl ether (652 μl, 6.8 mmol, 20 eq) was added followed by pyridinium p-toluene sulfonic acid (39 mg, 0.153 mmol, 0.45 eq). The reaction was monitored via TLC (20:80 EtOAc:Hex) and upon completion, the reaction was diluted with Et$_2$O. The organic layer was washed with 5% NaHCO$_3$ followed by brine. The organic layer was separated, dried over Na$_2$SO$_4$, filtered and the solvent was evaporated under reduced pressure. The crude product was purified by column chromatography on silica gel (15:85 EtOAc:Hex) to afford the compound 1b (150 mg, 77% yield) as a clear oil.

Compound 1b (90 mg, 0.16 mmol, 1 eq) was dissolved in THF (1 ml) and tetrabutyl ammonium fluoride was added (1M in THF, 240 μl, 0.24 mmol, 1.5 eq). The reaction was stirred at room temperature overnight. Upon completion, the solvent was removed under reduced pressure. The crude was dissolved in Et$_2$O and washed with water. The aqueous phase was washed two more times with Et$_2$O. The organic layers were combined, washed with brine, dried over Na$_2$SO$_4$, filtered and the solvent was evaporated under reduced pressure. The crude product was purified by column chromatography on silica gel (EtOAc) to afford the compound 1c (42 mg, 80% yield) as a white powder.

overnight. Afterwards the solvents were removed under reduced pressure. The crude was redissolved in DCM followed by the addition of 4-hydroxybenzaldehyde (20 mg, 0.164 mmol, 1.4 eq) and Tetrazole (0.45M in ACN, 780 µl, 0.351 mmol, 3 eq). The reaction was monitored by TLC (20:80 EtOAc:Hex). After 2 hours, tert-Butyl hydroperoxide (5.5M in decane, 43 µl, 0.234 mmol, 2 eq) was added drop-wise slowly at 0° C. The reaction was monitored via TLC (30:70 EtOAc:Hex). Upon completion, the reaction mixture was diluted with DCM, and washed with 5% NaHCO$_3$ followed by brine. The organic layer was separated, dried over Na$_2$SO$_4$, filtered and the solvent was evaporated under reduced pressure. The crude product was purified by column chromatography on silica gel (70:30 EtOAc:Hex) to afford the compound 1d (37 mg, 60% yield) as a white solid. MS (ES+): m/z calc. for C$_{24}$H$_{35}$ClO$_{11}$P: 530.19; found: 553.5 [M+Na]$^+$.

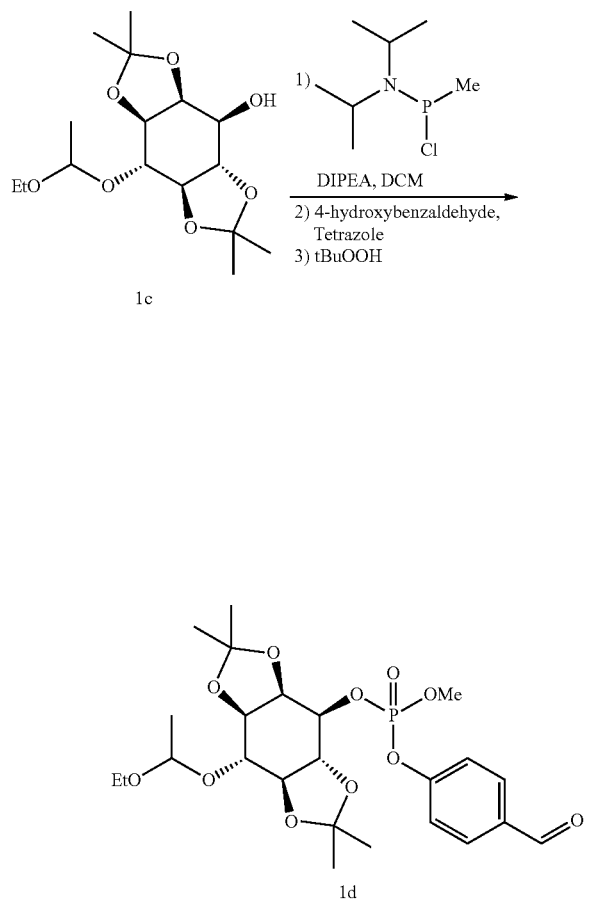

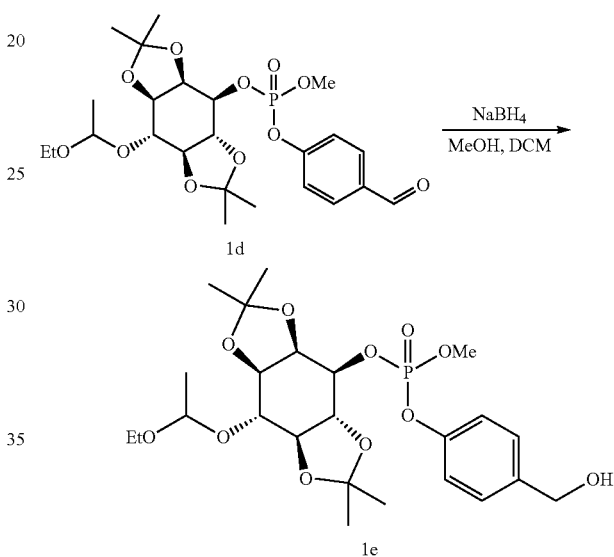

Compound 1e (95 mg, 0.18 mmol, 1 eq) was dissolved in MeOH with a few drops of DCM. NaBH$_4$ (14 mg, 0.36 mmol, 2 eq) was added slowly. The reaction was monitored via TLC (60:40 EtOAc:Hex). Upon completion, the reaction mixture was diluted with DCM, and washed with brine. The aqueous phase was washed two more times with DCM. The organic layers were combined, dried over Na$_2$SO$_4$, filtered and the solvent was evaporated under reduced pressure to afford the compound 1e (75 mg, 80% yield) as an off-white powder. MS (ES+): m/z calc. for C$_{24}$H$_{37}$ClO$_{11}$P: 532.21; found: 555.3 [M+Na]$^+$.

Compound 1c (39 mg, 0.117 mmol, 1 eq) was dissolved in dry DCM. Diisopropylethyl amine (63 µl, 0.351 mmol, 3 eq) was added followed by the drop-wise addition of N,N-Diisopropylmethylphosphonamidic chloride (45 µl, 0.234 mmol, 2 eq). The reaction was left at room temperature

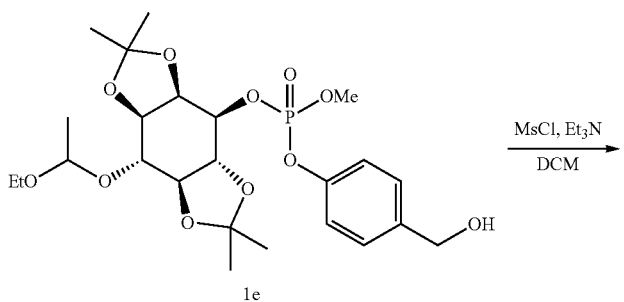

-continued

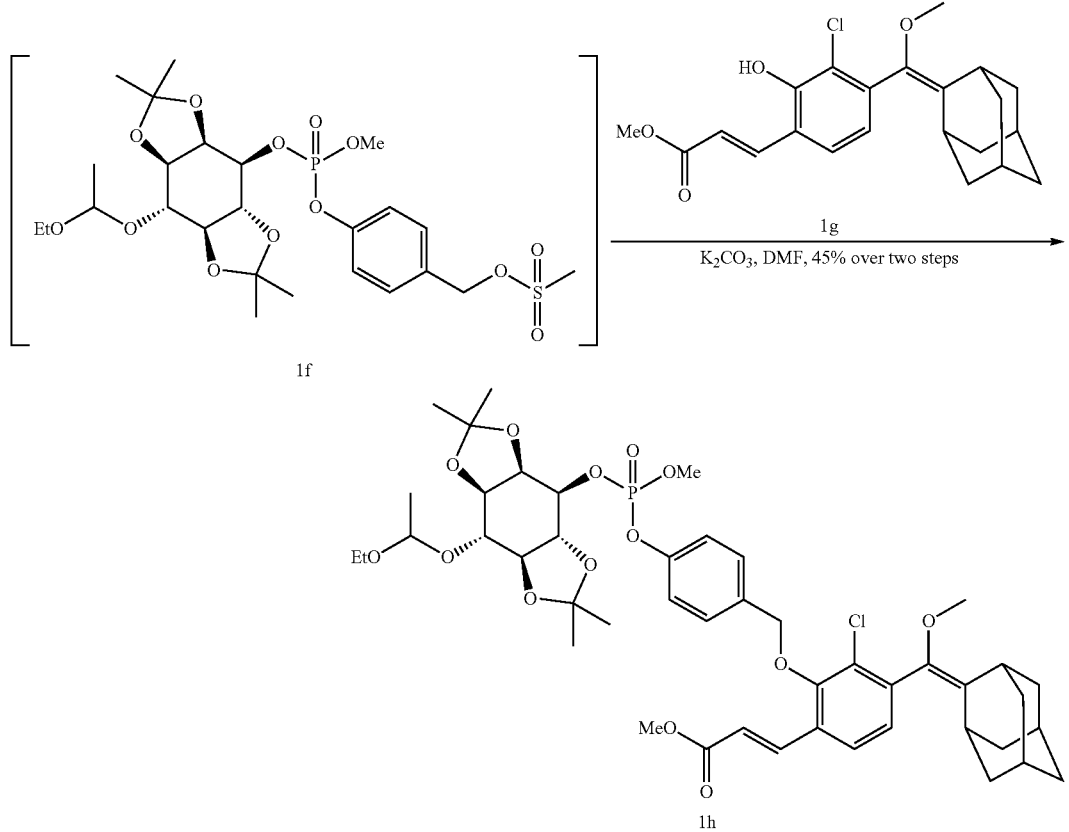

Compound 1e (305 mg, 0.57 mmol, 1 eq) was dissolved in DCM. Methanesulfonyl chloride (54 µl, 0.68 mmol, 1.2 eq) and trimethylamine (97 µl, 0.68 mmol, 1.2 eq) were added dropwise. The reaction was monitored via TLC (30:70 EtOAc:Hex). Upon completion, the reaction mixture was diluted with DCM, and washed with saturated NaHCO$_3$. The organic layer was separated, dried over Na$_2$SO$_4$, filtered and the solvent was evaporated under reduced pressure, to yield compound 1f which was used without further purification. MS (ES+): m/z calc. for C$_{25}$H$_{39}$ClO$_{13}$PS: 610.18; found: 633.26 [M+Na]$^+$. Compound 1f and compound 1g (prepared in accordance with Green, O., Eilon, T., Hananya, N., Gutkin, S., Bauer, C R., Shabat, D., *ACS Central* Sci., 2017, 4, 349-58) (288 mg, 0.74 mmol, 1.3 eq) were dissolved in dry DMF and K$_2$CO$_3$ was added (197 mg, 1.43 mmol, 2.5 eq). The reaction was monitored by TLC (30:70 EtOAc:Hex) and RP-HPLC (70-100% ACN in water, 20 min). Upon completion, the solvent was removed under reduced pressure. The crude product was purified by column chromatography on silica gel (75:25 EtOAc:Hex) to afford the compound 1h (231 mg, 45% yield over two steps) as a white foam. MS (ES+): m/z calc. for C$_{46}$H$_{60}$ClO$_{14}$P: 902.34; found: 925.60 [M+Na]$^+$.

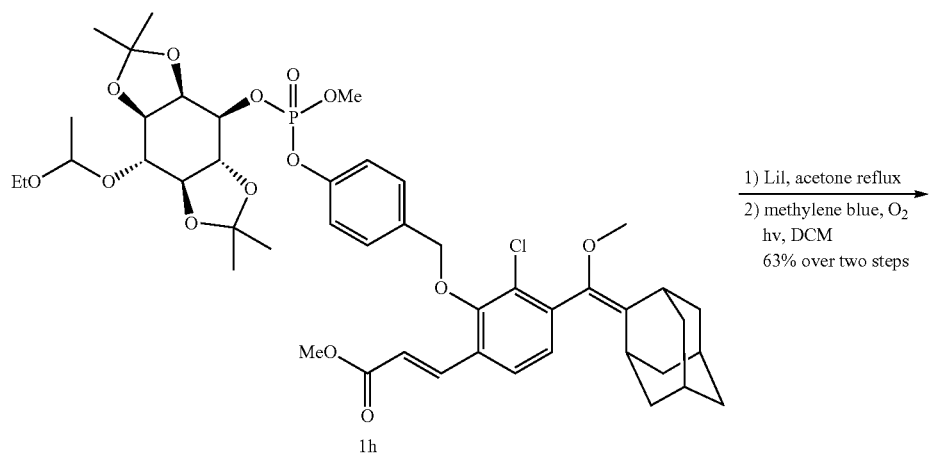

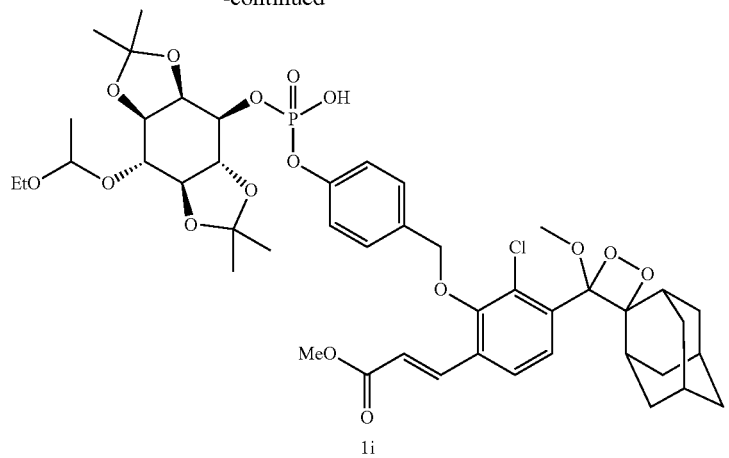

1i

Compound 1h (20 mg, 0.022 mmol, 1 eq) was dissolved in acetone and lithium iodide was added (6 mg, 0.044 mmol, 2 eq). The reaction was heated to reflux and monitored by RP-HPLC RP-HPLC (10-60% ACN, ammonium carbonate 15 mM Buffer, 20 min). The solvent was removed and the crude was dissolved in DCM. A few milligrams of methylene blue were added and oxygen was bubbled through the solution while irradiating with yellow light. The reaction was monitored by RP-HPLC (15-70% ACN, ammonium carbonate 15 mM Buffer, 20 min). Upon completion, the reaction mixture was concentrated by evaporation under reduced pressure. The crude product was purified by preparative RP-HPLC (15-70% ACN, ammonium carbonate 15 mM Buffer, 20 min) to afford compound 1i (13 mg, 63% yield over two steps) as an off-white solid. MS (ES−): m/z calc. for $C_{45}H_{58}ClO_{16}P$: 920.32; found: 919.67 [M−H]⁺.

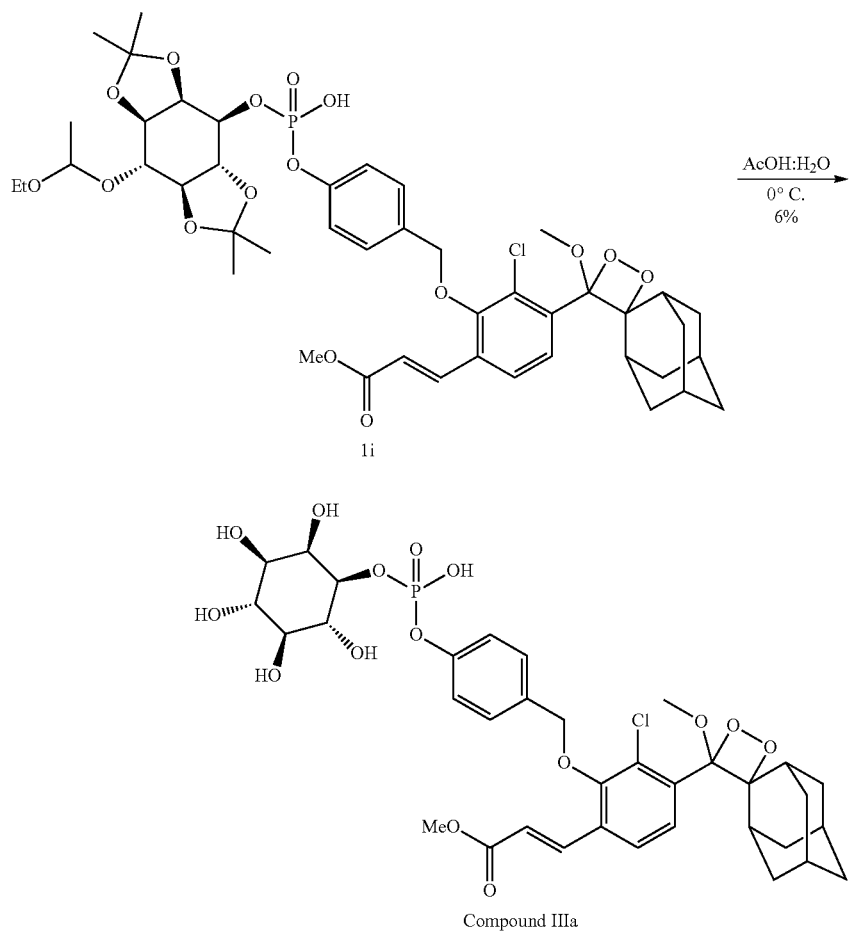

Compound IIIa

Compound 1i (13 mg, 0.041 mmol) was added to cooled (0° C.) AcOH:H₂O 1:4 and the resulting suspension was stirred at 0° C. After 24 hours the solvent was removed by evaporating with ethanol. The crude product was purified by preparative RP-HPLC (15-70% ACN, ammonium carbonate 15 mM Buffer, 20 min) to afford Compound IIIa (0.7 mg, 6% yield) as an off-white solid. MS (ES−): m/z calc. for $C_{35}H_{42}ClO_{15}P$: 768.19; found: 767.5 [M−H]⁻.

Synthesis Example 3: Synthesis of Compound IVa

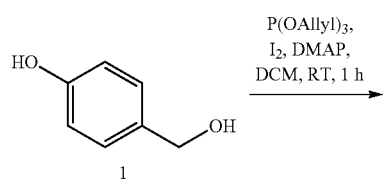

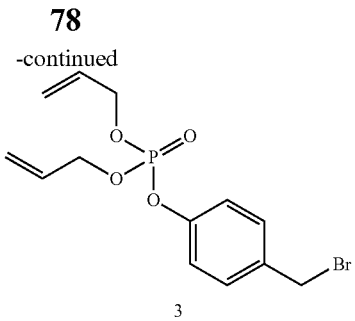

A solution of alcohol 2 (2.00 g, 0.00700 mol) in DCM (100 mL) was cooled to 0° C. NBS (2 eq., 0.014 mol, 2.5 g) and Ph₃P (2 eq., 0.014 mol, 3.67 g) were added (pale-yellow solution). After 0.5 h the mixture (pale-yellow solution) was concentrated in vacuo yielding pale-yellow oil. This residue was purified by column chromatography (silicagel, eluent hexane:Et₂O 1:1 to 1:2) affording bromide 3 as a pale-yellow oil, 1.2 g, 49%.

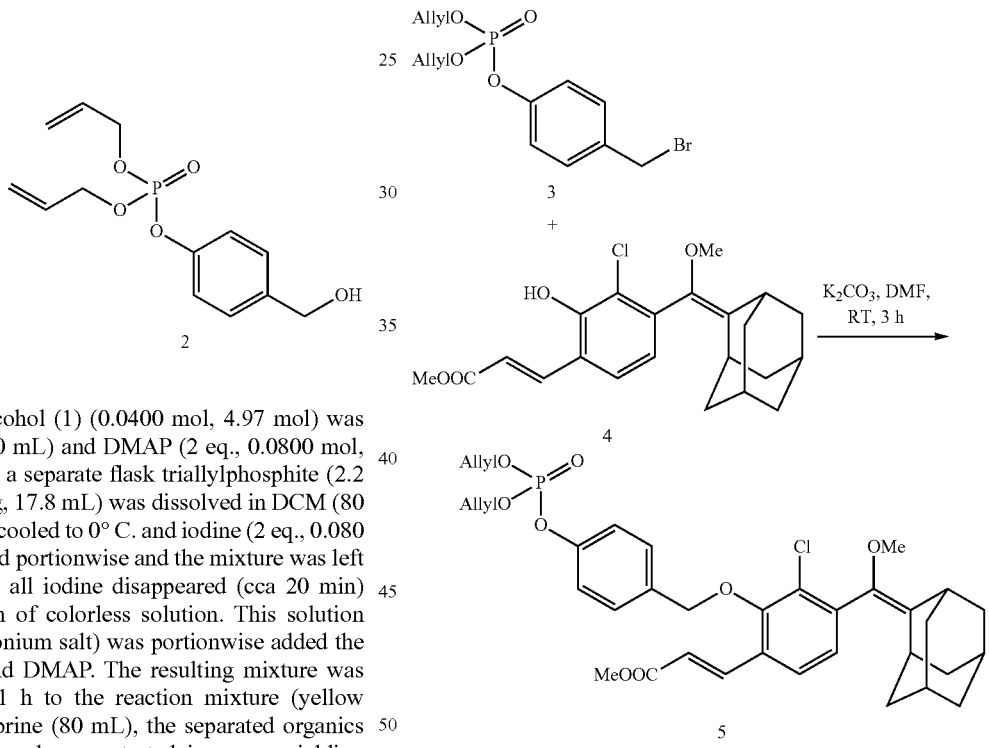

4-Hydroxybenzylacohol (1) (0.0400 mol, 4.97 mol) was dissolved in DCM (80 mL) and DMAP (2 eq., 0.0800 mol, 9.77 g) was added. In a separate flask triallylphosphite (2.2 eq. 0.0880 mol, 17.8 g, 17.8 mL) was dissolved in DCM (80 mL), the mixture was cooled to 0° C. and iodine (2 eq., 0.080 mol, 20.3 g) was added portionwise and the mixture was left stirring at 0° C. until all iodine disappeared (cca 20 min) resulting in formation of colorless solution. This solution (containing a phosphonium salt) was portionwise added the solution of ester 1 and DMAP. The resulting mixture was stirred at RT. After 1 h to the reaction mixture (yellow solution) was added brine (80 mL), the separated organics were dried (MgSO₄) and concentrated in vacuo yielding pale-yellow oil. This residue was purified by column chromatography (silicagel, eluent hexane:EtOAc 2:1 to 1:1 to 2:1) yielding alcohol 2 as a colorless oil, 2.0 g, 18%.

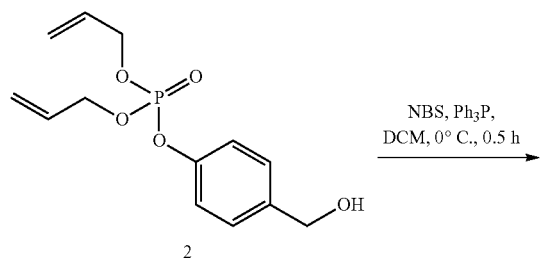

A solution of ester 4 (1.34 g, 0.00345 mol) in DMF (9 mL) (colorless solution), was cooled to 0° C. (yellow suspension), K₂CO₃ (1.2 eq., 0.00413 mol, 0.57 g) was added and the mixture was stirred at 0° C. After 10 min a solution of bromide 3 (1 eq., 0.00345 mol, 1.20 g) in DMF (8 mL) was added and the resulting mixture (yellow-orange suspension) was stirred at RT. After 3 h to the mixture was added NH₄Cl (50 mL) and the resulting mixture was extracted with EtOAc (3 times 20 mL), the combined organics were dried (MgSO₄) and concentrated in vacuo yielding a pale-yellow oil, 3.8 g. This residue was purified by column chromatography (silicagel, eluent Et₂O:hexane 1:1 to Et₂O) affording ester 5 as a pale-yellow oil, 1.9 g, 84%; ¹H NMR (300 MHz, CDCl₃) δ ppm 1.60-2.03 (m, 12H) 2.12 (br s, 1H) 3.33 (br s, 1H) 3.37 (s, 3H) 3.86 (s, 3H) 4.70 (ddq, J=8.5, 5.7, 1.3, Hz, 4H) 5.02 (m, 2H) 5.28-5.47 (m, 4H) 5.93-6.06 (m, 2H) 6.51 (d, J=16.2 Hz, 1H) 7.13 (dd, J=8.1, 0.5 Hz, 1H) 7.27-7.31 (m, 2H) 7.49 (d, J=8.1 Hz, 1H) 7.53 (d, J=8.3 Hz, 2H) 7.98 (d, J=16.2 Hz, 1H).

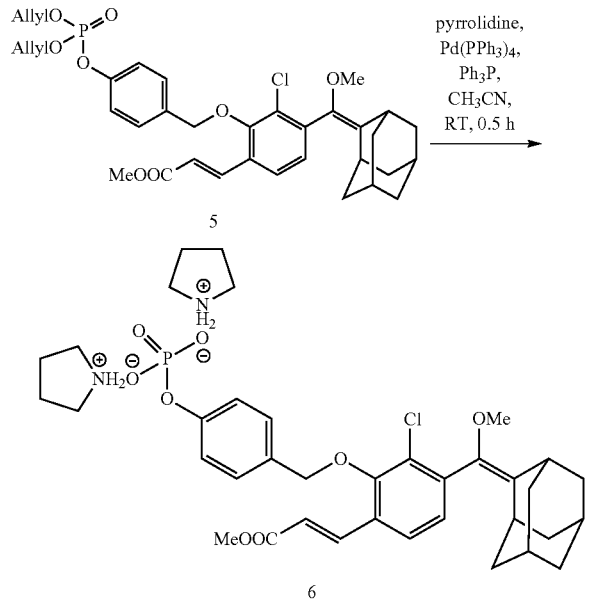

To a solution of ester 5 (1.9 g, 0.0029 mol) in CH$_3$CN (29 mL) was added pyrrolidine (6.2 eq., 0.0018 mol, 1.28 g, 1.5 mL), Ph$_3$P (0.20 eq., 0.00059 mol, 0.15 g) and Pd(PPh$_3$)$_4$ (0.05 eq., 0.000145 mol, 0.168 g) and the resulting mixture was stirred at RT. After 0.5 h the reaction mixture was concentrated in vacuo yielding pale-yellow oil. The crude mixture containing ester 6 was taken for the next step (Me-ester hydrolysis) without further purification.

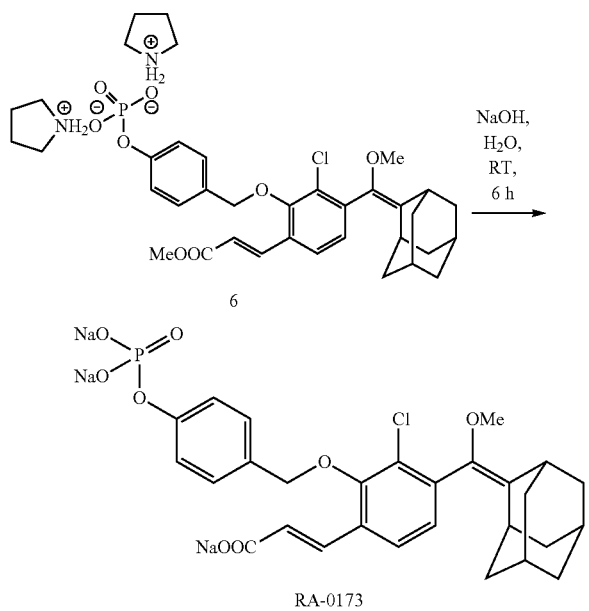

Water (28 mL) and NaOH (3 eq., 0.0087, 0.35 g) were added to ester 6 (0.0029 mol, theoretical number of moles from the previous step), the mixture was extracted with Et$_2$O (2 times 30 mL), the combined organics were discarded and the aqueous layer (cloudy yellow solution) was stirred at RT. After 6 h the reaction mixture (yellow solution) was extracted with Et$_2$O (5 mL) and the separated aqueous layer was concentrated in vacuo yielding yellow-green oil. This residue was purified by column chromatography (silicagel, eluent EtOAc:MeOH 50:50 to 40:60) yielding RA-0173 an off-white solid, 0.81 g, 46%.

$^1$H NMR (300 MHz, D$_2$O) δ ppm 1.53-1.95 (m, 13H) 3.05 (br s, 1H) 3.25 (br s, 3H) 4.98 (br s, 2H) 6.44 (br d, J=16.0 Hz, 1H) 7.10 (br d, J=7.8 Hz, 3H) 7.37 (br d, J=8.0 Hz, 2H) 7.45-7.63 (m, 2H).

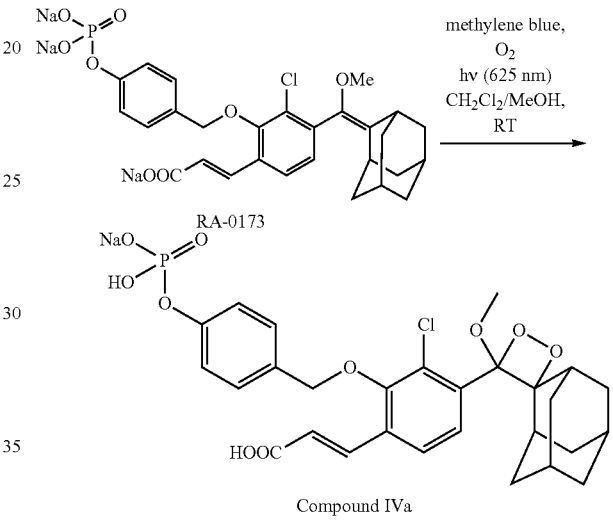

Compound IVa

To a solution of RA-0173 (0.1 g, 0.00016 mol) in DCM (30 mL) and MeOH (30 mL) was added methylene blue trihydrate (0.04 eq., 0.0065 mmol, 2.4 mg) and the resulting mixture was filtered through a syringe filter (25 mm, 0.45 μm). The solution was irradiated in homogeneous flow (0.9-1.1 mL min$^{-1}$) with an LED lamp (Peschl Ultraviolet, 100 W, 625 nm) and the oxygen pressure set to 1.0 bar. The reaction mixture was collected in a 250 mL flask and continuously degassed by bubbling nitrogen through the solution. After 60 minutes the flow was stopped and the reaction mixture diluted with EtOAc (20 mL), filtered through a plug of silica and washed with MeOH/EtOAc 9:1 (120 mL). The first filtrate was discarded while the MeOH/EtOAc filtrate was concentrated under reduced pressure without heating. Compound IVa was obtained as an off-white solid, 91 mg, 93%.

The sodium atom(s) may be exchanged with hydrogen to yield "OH" groups by means known to the skilled person, e.g. ion exchange.

$^1$H NMR (400 MHz, CD$_3$OD) δ ppm 1.40 (br. s., 2H) 1.52 (d, J=10.8 Hz, 1H) 1.62-1.89 (m, 7H) 2.00 (br. s., 2H) 2.40 (d, J=12.5 Hz, 1H) 2.96 (br. s., 1H) 3.18 (s, 3H) 6.58 (d, J=16.1 Hz, 1H) 7.24 (d, J=7.8 Hz, 2H) 7.40 (d, J=8.4 Hz, 2H) 7.72 (d, J=8.3 Hz, 1H) 7.78 (d, J=15.9 Hz, 1H) 7.84 (d, J=8.4 Hz, 1H). [Comment: the benzylic 2H peak is hidden under the H$_2$O peak in CD$_3$OD]

Synthesis Example 4: Synthesis of Compound Va

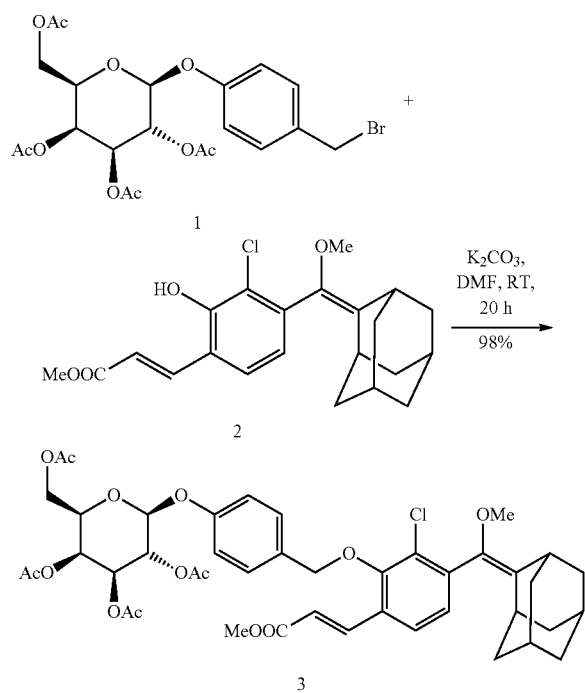

Ester 2 (0.00644 mol, 2.51 g) was dissolved in DMF (50 mL) and the resulting mixture was cooled to 0° C. K$_2$CO$_3$ (1.2 eq., 0.00773 mol, 1.07 g) was added at 0° C. and the mixture was stirred at 0°. After 10 min a solution of bromide 1 (1.2 eq., 0.00773 mol, 4.00 g) in DMF (14 mL) was added and the resulting mixture was stirred at RT. After 20 h to the mixture was added saturated solution of NH$_4$C (200 mL) and the resulting mixture was extracted with Et$_2$O (3 times 60 mL), the combined organics were washed with brine (60 mL), dried (MgSO$_4$) and concentrated in vacuo yielding a pale-yellow oil. This residue was purified by column chromatography yielding ester 3 (5.2 g, 98%) as a white solid.

Ester 3 (0.00300 mol, 2.48 g) was dissolved in a mixture of THF (60 mL) and H$_2$O (15 mL) and LiOH (3.9 eq., 0.0117 mol, 0.280 g) was added. The resulting mixture was stirred at RT. After 24 h to the mixture was added saturated NH$_4$Cl (80 mL) and the mixture was extracted with EtOAc (3-times 60 mL), the combined organics were washed with brine (60 mL), dried (MgSO$_4$) and concentrated in vacuo yielding a pale-yellow oil. This residue was purified by column chromatography (eluent EtOAc to EtOAc-MeOH 8:1) affording ester 4 (1.33 g, 70%) as an off-white solid.

4 (50 mg, 0.076 mmol) and Methylene Blue (1.2 mg, 3.2 mmol) were dissolved in a DCM/MeOH mixture (30 mL, 5:1), and the solution was passed through a syringe filter (0.45 mm). The clear solution was pumped with an MPLC pump (Labomatic MD 80/100) into a gas-liquid mixing cell (Peschl Ultraviolet) and mixed with oxygen (1.0 bar). The oxygen saturated solution was then irradiated in a continuous flow at room temperature with a LED lamp (625 nm, novaLIGHT FLED 100-625, Peschl Ultraviolet). The mixture was collected in a 250 mL round-bottomed flask and the solution continuously purged with nitrogen. The obtained reaction mixture was diluted with 20 mL EtOAc, filtered through a short pad of silica and washed with EtOAc/MeOH (120 mL, 9:1). The filtrate was concentrated at room temperature under exclusion of light, and the obtained solid residue was triturated with Et$_2$O. The product compound Va was isolated as an off-white solid (32 mg, 0.046 mmol, 61%).

$^1$H NMR (400 MHz, CDCl$_3$) δ ppm 1.29-1.39 (m, 3H), 1.46 (d, J=13.1 Hz, 1H), 1.57-2.1 (m, 12H), 2.32 (d, J=13.1 Hz, 1H), 3.02 (br. s, 1H), 3.21 (s, 3H), 3.68 (br. s, 1H), 3.72-3.80 (m, 4H), 3.83-4.07 (m, 3H), 4.13 (br. s, 1H), 4.80-4.91 (m, 2H), 4.93 (d, J=7.5 Hz, 1H), 6.36 (dd, J=16.2, 5.2 Hz, 1H), 7.02 (d, J=8.7, 2 H), 7.32 (d, J=6.4 Hz, 2H), 7.52 (dd, J=7.9, 3.4 Hz, 1H), 7.74 (dd, J=16.1, 5.4 Hz, 1H), 7.89 (d, J=8.5 Hz, 1H).

Synthesis Example 5: Synthesis of Compound VIa

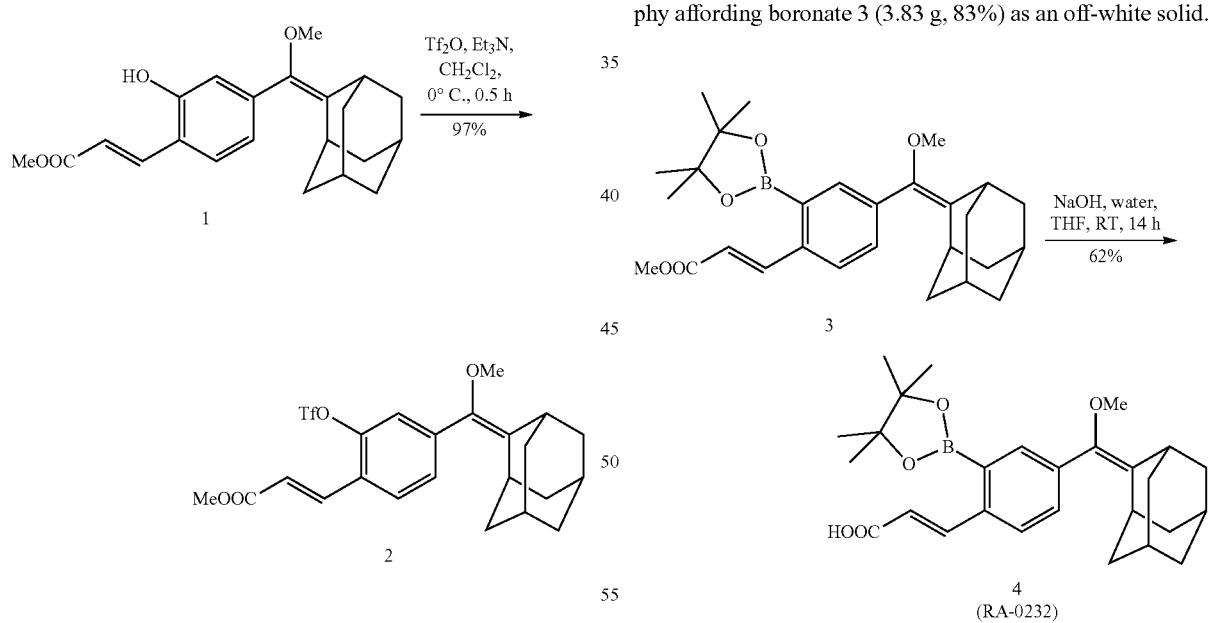

A solution of phenol 1 (0.00100 mol, 3.54 g) in DCM (40 mL) was cooled to 0° C. and Tf$_2$O (1.2 eq., 0.0012 mol, 3.4 g, 2.0 mL) was added under argon, followed by a dropwise addition of Et$_3$N (2.5 eq., 0.0025 mol, 2.5 g, 3.5 mL). The resulting mixture was stirred at 0° C. After 30 min to the reaction mixture was added brine (50 mL), the separated aqueous layer was extracted with DCM (60 mL), combined organics dried (MgSO$_4$) and concentrated in vacuo yielding a brown oil. The mixture was purified by column chromatography (hexane to hexane:EtOAc 9:1) affording triflate 2 (5.05 g, 97%) as a colorless oil.

Triflate 2 (0.00925 mol, 4.50 g), B$_2$Pin$_2$ (2 eq., 0.0185 mol, 4.96 g), KOAc (3 eq., 0.0278 mol, 2.72 g) and Pd(dppf)$_2$C2 (0.2 eq., 0.00185 mol, 1.35 g) were placed in a round-bottom flask, the content was placed under argon (2 vacuum-argon cycles) and dry dioxane (40 mL) was added. The resulting mixture was degassed (2 vacuum-argon cycles) and stirred at reflux under argon. After 45 min the reaction mixture (dark brown mixture) was concentrated in vacuo. This mixture was purified by column chromatography affording boronate 3 (3.83 g, 83%) as an off-white solid.

To a mixture of boronate 3 (0.00500 mol, 2.30 g) and THF (20 mL) was added water (5 mL) and NaOH (3 eq., 0.0150 mol, 0.600 g) and the resulting mixture was stirred at 40° C. After 14 h to the mixture was added 0.5 M HCl (200 ml) and the mixture was extracted with EtOAc (3 times 50 ml). The combined organics were washed with brine (50 mL), dried (MgSO$_4$) and concentrated in vacuo yielding pale-yellow oil. This residue was purified by column chromatography afforded acid 4 (RA-0232) as a white solid, 1.4 g, 62%.

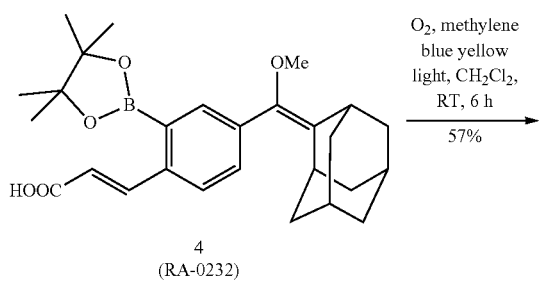

4
(RA-0232)

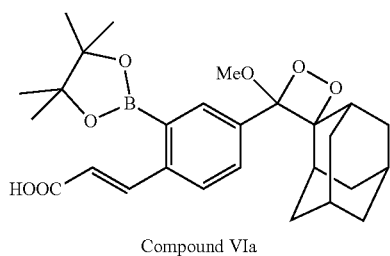

Compound VIa

To a solution of acid 4 (0.00019 mol, 0.085 g) in DCM (18 mL) was added methylene blue (9 mg), the reaction flask was sealed with a rubber septum and a balloon filled with oxygen was attached (deep blue solution). The resulting mixture was irradiated with yellow light (589 nm). After 6 h the reaction mixture was concentrated in vacuo yielding a blue oil. This residue was purified by column chromatography yielding Compound Via as a pale-yellow solid, 0.052 g, 57%.

Synthesis Example 6: Synthesis of Compound VIIa

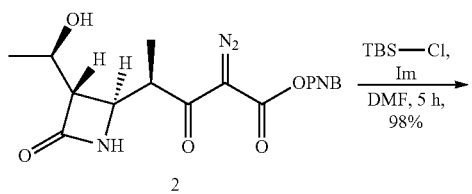

2

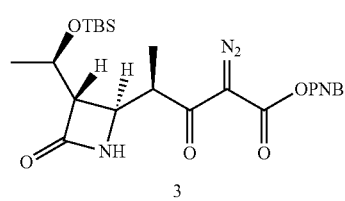

3

(R)-4-Nitrobenzyl4-((2R,3S)-3-((R)-1-((tert-butyldimethylsilyl)oxy)ethyl)-4-oxoazetidin-2-yl)-2-diazo-3-oxopentanoate (3)

To a solution of commercially available Meropenem intermediate 2 (2.6 g, 6.8 mmol) in anhydrous DMF (15 mL) under argon atmosphere were added TBDMSCl (4.0 g, 27.1 mmol) and imidazole (2.8 g, 40.8 mmol). The resulting mixture was stirred at rt for 5 h. After dilution with Ethyl-acetate (50 mL), the solution was washed with water (20 mL×3) and brine (20 mL×1), subsequently. The organic layer was dried over $Na_2SO_4$ and concentrated. The residue was purified by chromatography on silica gel column to afford the titled compound 3 as white solid (3.3 g, 98%). MS (ES+) m/z calculated for $C_{23}H_{32}N_4NaO_7Si$ [M+Na]$^+$527.2, found 527.4.

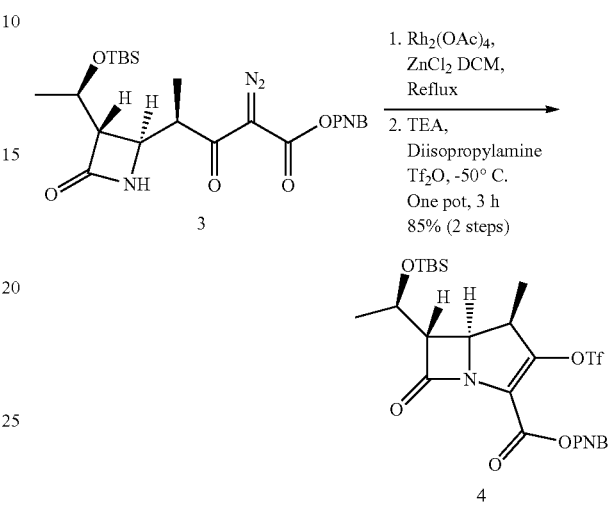

(4R, 5R, 6S)-4-Nitrobenzyl-6-((R)-1-((tert-butyldimethylsilyl)oxy)ethyl)-4-methyl-7-oxo-3-(((trifluoromethyl)sulfonyl)oxy)-1-azabicyclo[3.2.0]hept-2-ene-2-carboxylate (4)

To a round bottom flask under argon were added $ZnCl_2$ (anhydrous, 20 mg, 0.15 mmol), compound 3 (2.4 g, 4.8 mmol), $Rh_2(OAc)_4$ (21.5 mg, 0.05 mmol) and $CH_2Cl_2$ (anhydrous, 15 mL) and then heated to reflux for 90 min until disappearance of compound 3 (monitored by TLC). The resulting mixture were cooled to −50° C. and a mixture of triethylamine (235 µL, 1.7 mmol) and diisopropylamine (680 µL, 4.8 mmol) were added dropwise, followed by the slow addition of $Tf_2O$ (850 µL, 5.0 mmol). The suspension were stirred at −50° C. for 60 min and purified by chromatography on a short silica gel column with dichloromethane as eluent to afford desired compound 4 as white solid (2.5 g, 85%). MS (ES+) m/z calculated for $C_{24}H_{32}F_3N_2O_9SSi$ [M+Na]$^+$609.1, found 609.4.

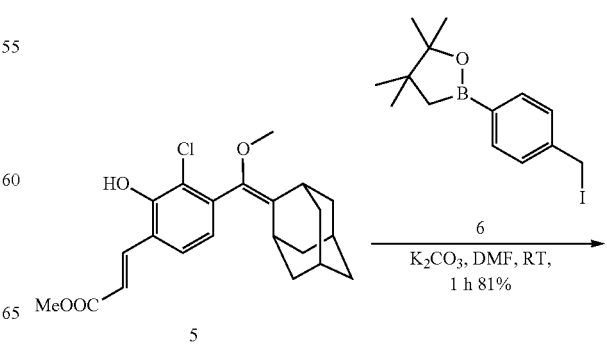

5

-continued

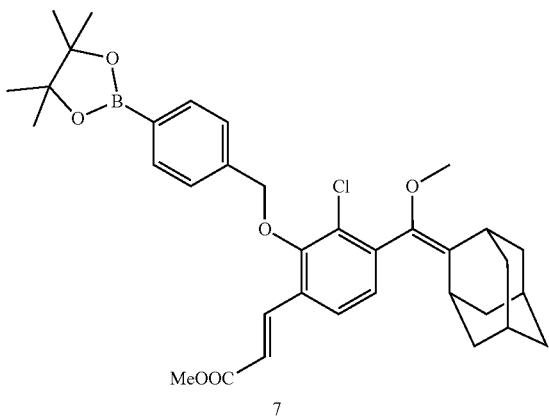

Methyl (E)-3-(4-(((1r,3r,5R,7S)-adamantan-2-ylidene)(methoxy)methyl)-3-chloro-2-((4-(4,4,5,5-tetramethyl-1,3,2-dioxaborolan-2-yl)benzyl)oxy)phenyl)acrylate (7)

Enol ether 5 (prepared in accordance with Green, O., Eilon, T., Hananya, N., Gutkin, S., Bauer, C R., Shabat, D., *ACS Central Sci.*, 2017, 4, 349-58) (500 mg, 1.3 mmol) was dissolved in 3 mL dry DMF and cooled to 0° C. $K_2CO_3$ (195 mg, 1.4 mmol) was added and the solution stirred at 0° C. for 10 minutes, before compound 6 (cf., Karton-Lifshin N., Albertazzi L., Bendikov M., Baran P S., Shabat D., *J Am Chem Soc.*, 2012, 134(50), 20412-20) (536.6 mg, 1.6 mmol) was added. The reaction mixture stirred for 30 minutes at room temperature and monitored by TLC. After completion, the reaction mixture diluted with EtOAc (30 ml) and was washed with saturated $NH_4Cl$ (10 ml). The organic layer was separated, washed with brine, dried over $Na_2SO_4$ and evaporated under reduced pressure. The crude product was purified by column chromatography on silica gel to afford the titled compound 7 as white solid (661 mg, 81%). MS (ES+) m/z calculated for $C_{35}H_{42}BClNaO_6$ [M+Na]$^+$627.2, found 627.5.

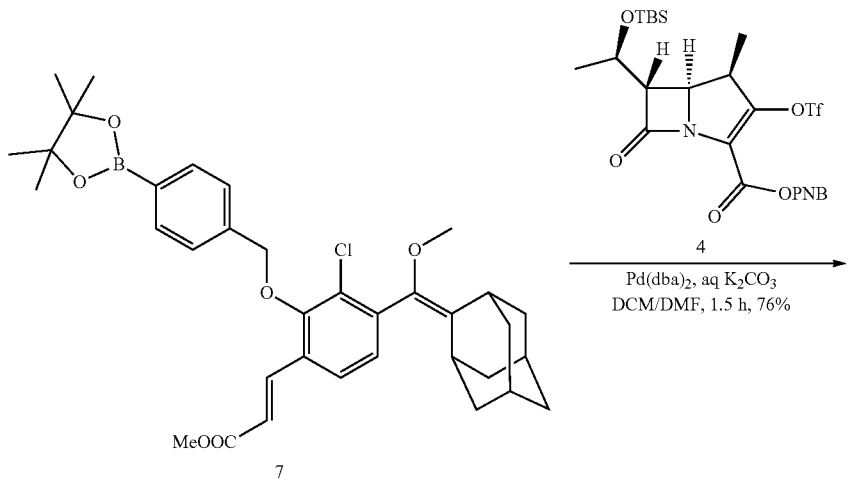

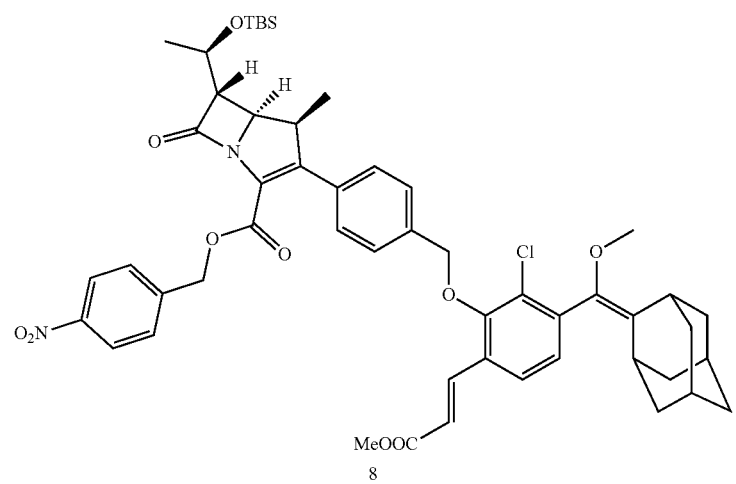

4-Nitrobenzyl (4S,5R,6S)-3-(4-((3-(((1 r,3r,5R,7S)-adamantan-2-ylidene)(methoxy)methyl)-2-chloro-6-((E)-3-methoxy-3-oxoprop-1-en-1-yl)phenoxy)methyl)phenyl)-6-((R)-1-((tert-butyldimethylsilyl)oxy)ethyl)-4-methyl-7-oxo-1-azabicyclo[3.2.0]hept-2-ene-2-carboxylate (8)

To a solution of pinacolboronate 7 (304 mg, 0.50 mmol) and vinyl triflate 4 (304 mg, 0.50 mmol) in a mixture of CH₂Cl₂ (2 mL) and DMF (1.1 mL) was added Pd(dba)₂ (14 mg, 0.02 mmol) and 3 M aqueous K₂CO₃ (0.5 mL, 1.5 mmol). The mixture was stirred at 37° C. for 2.5 h and monitored by TLC. After completion, the reaction mixture diluted with EtOAc (20 ml) and was washed with saturated NH₄Cl (10 ml). The organic layer was separated, washed with brine, dried over Na₂SO₄ and evaporated under reduced pressure. The crude product was purified by column chromatography on silica gel to afford the titled compound 8 (358 mg, 76%). MS (ES+) m/z calculated for C$_{52}$H$_{62}$ClN$_2$O$_{10}$Si [M+Na]$^+$ 937.4, found 937.8.

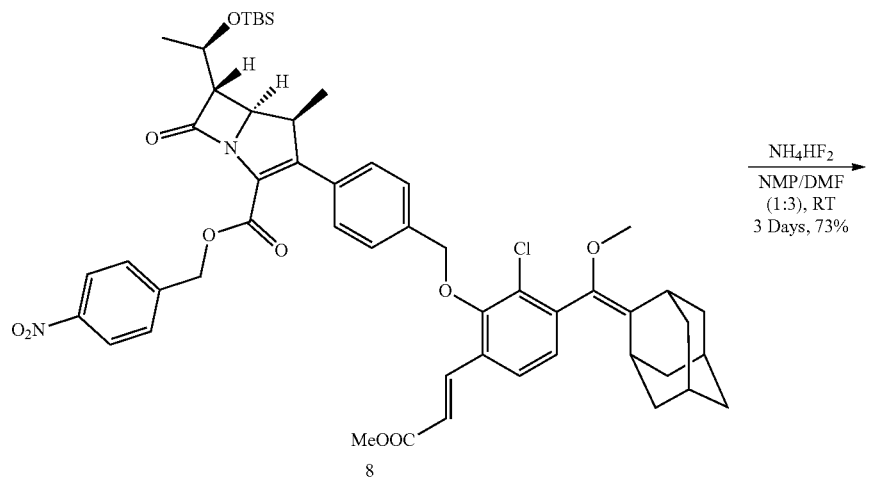

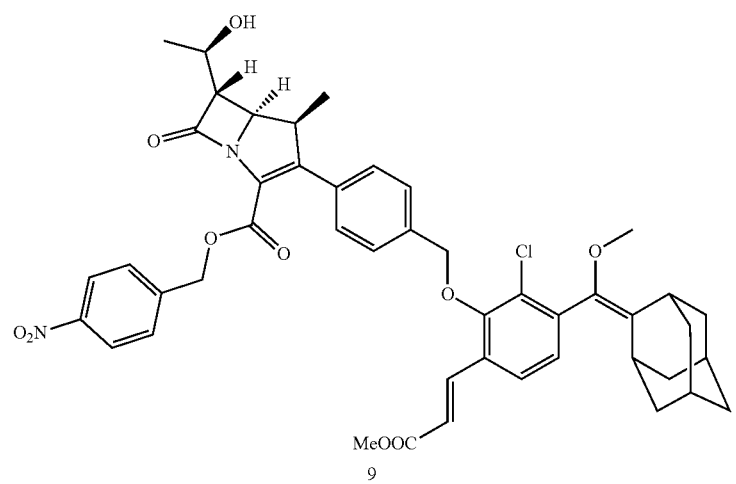

4-nitrobenzyl (4S,5R,6S)-3-(4-((3-(((1r,3r,5R,7S)-adamantan-2ylidene) (methoxy)methyl)-2-chloro-6-((E)-3-methoxy-3-oxoprop-1-en-1-yl)phenoxy) methyl)phenyl)-6-((R)-1-hydroxyethyl)-4-methyl-7-oxo-1-azabicyclo[3.2.0]hept-2-ene-2-carboxylate(9)

To a solution of 8 (350 mg, 0.4 mmol) in N-methylpyrrolidinone/DMF (1:3, 0.7 mL) at room temperature was added ammonium hydrogen difluoride (150 mg, 2.8 mmol) and the resulting reaction mixture were stirred at room temperature for 72 h (monitored by TLC). The reaction was then diluted with ethyl acetate (40 mL) and washed with water and brine. After dried over $Na_2SO_4$ and concentration under reduced pressure, the residue was purified by chromatography on silica gel column to afford the title compound 9 (290.6 mg, 73%). MS (ES+) m/z calculated for $C_{46}H_{48}ClN_2O_{10}$ [M+Na]$^+$823.4, found 823.6.

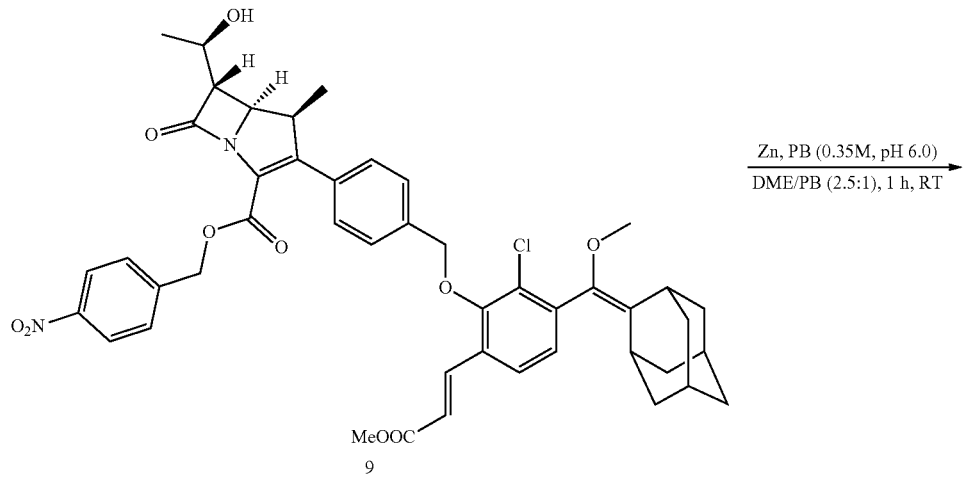

(4S,5R,6S)-3-(4-((3-(((1r,3r,5R,7S)-adamantan-2-ylidene)(methoxy)methyl)-2-chloro-6-((E)-3-methoxy-3-oxoprop-1-en-1-yl)phenoxy)methyl)phenyl)-6-((R)-1-hydroxyethyl)-4-methyl-7-oxo-1-azabicyclo[3.2.0]hept-2-ene-2-carboxylic acid (10)

To a solution of compound 7 (20 mg, 0.02 mmol) in 0.5 mL DME at 20° C. were added 0.2 mL phosphate buffer (0.35 M, pH 6.0) and activated zinc powder. The reaction mixture were then stirred at the same temperature for 1 h. The precipitates was removed with a 0.22 μM PTFE syringe filter and the filtrate was purified using preparative RP-HPLC with $CH_3CN-H_2O$ (30 mmol $NH_4HCO_3$ buffered water, $CH_3CN$ contains 30% buffered water) as mobile phase. MS (ES+) m/z calculated for $C_{39}H_{42}ClNNaO_8$ [M+Na]$^+$710.2, found 710.5.

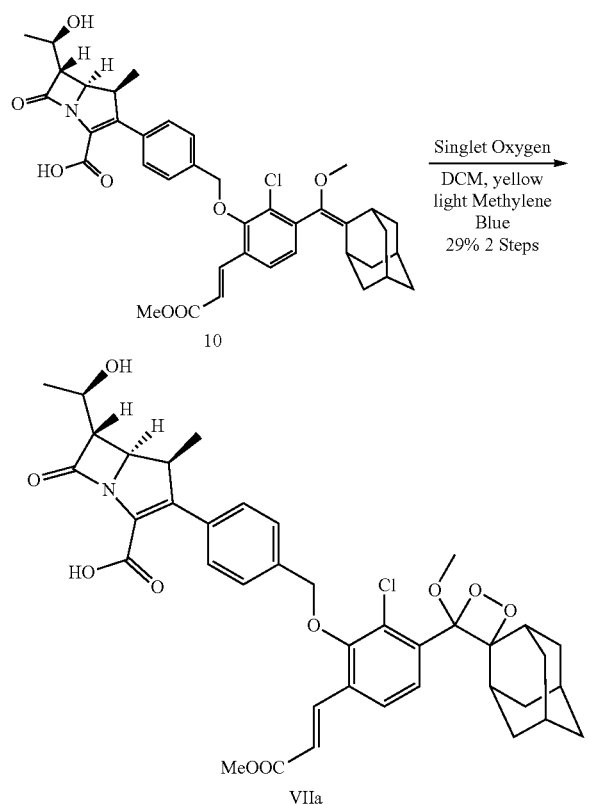

(4S,5R,6S)-3-(4-((2-Chloro-6-((E)-3-methoxy-3-oxoprop-1-en-1-yl)-3-((1r,3r,5S,7S)-4'-methoxyspiro[adamantane-2,3'-[1,2]dioxetan]-4'-yl)phenoxy)methyl)phenyl)-6-((R)-1-hydroxyethyl)-4-methyl-7-oxo-1-azabicyclo[3.2.0]hept-2-ene-2-carboxylicacid (1)

Enol ether 10 and few milligrams of methylene blue were dissolved in 15 ml of DCM. Oxygen was bubbled through the solution while irradiating with yellow light for 20 minutes. The reaction was monitored by RP-HPLC. After completion, the reaction mixture was concentrated by evaporation under reduced pressure. The crude product was purified by preparative RP-HPLC with $CH_3CN-H_2O$ (30 mmol $NH_4HCO_3$ buffered water, $CH_3CN$ contains 30% buffered water) as mobile phase to afford compound VIa as white solid (3 mg, 30%). MS (ES+) m/z calculated for $C_{39}H_{42}ClNNaO_{10}$ [M+Na]$^+$742.2, found 742.5.

Synthesis Example 7: Synthesis of a D-Luciferin-Spacer-Caprylate

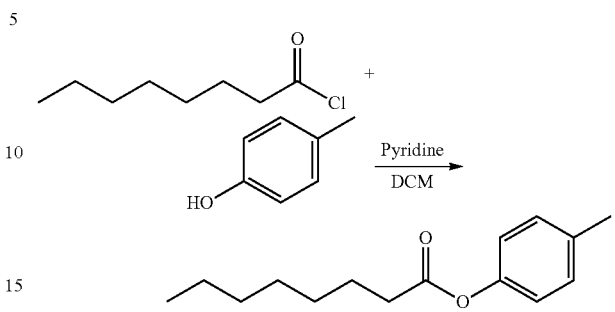

500 ml 3-necked flask was charged with 10 g of p-cresol (92.5 mmol/1 eq.) followed by dry DCM (200 mL). Mixture was cooled in ice-water cooling bath. To this solution Pyridine (10.24 g/12.9 mmol/1.4 eq.) was added. Capryloyl chloride (18 g/110.7 mmol/1.2 eq.) (dissolved in 50 ml of dry DCM) was added dropwise from dropping funnel keeping temperature of reaction mixture below 12° C. After 15 minutes cooling bath was removed and mixture was stirred at ambient temperature. Reaction was completed after 50 minutes (control by TLC (petrolether/AcOEt=2/1)). Reaction mixture was washed by 200 mL of water, followed by 2×200 mL of 0.2M NaOH solution. Organic phase was dried over $Na_2SO_4$, filtered and concentrated on rotavap. Residue (approx 23 g) was purified on short plug of silica gel (h=45 mm, d=100 mm) eluting with DCM. Product in from of colourless fruity smell oil (20.9 g/96% yield) was used in next synthetic step without further purification.

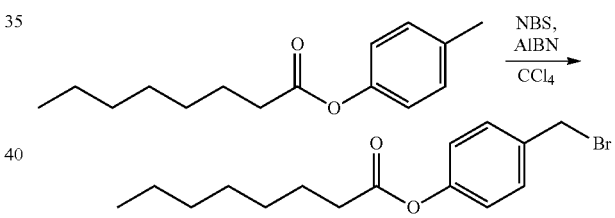

To 250 mL reaction flask charged with CCl4 (140 mL) was added p-cresol-caprylate (20.9 g/92.5 mmol/1 eq.) followed by NBS (19.84 g/111.5 mmol/1.25 eq.). Suspension was stirred in oil bath (100° C.) for 15 min. Oil bath was removed and AIBN (915 mg/5.6 mmol/5 mol %) was added in one portion. Reaction started with intensive reflux, after approx 2 minutes, when reflux was much more gentle mixture was immersed in hot heating bath again. TLC after 20 min (Petrolether/AcOEt=10/1) showed full conversion. Reaction mixture was cooled in cold water to 15° C. At this temperature mixture was filtered through S3 fritt, washed with 10 mL of DCM and filtrate was concentrated on vacuo. Raw product (27.7 g/99% yield) was used in next synthetic step without purification.

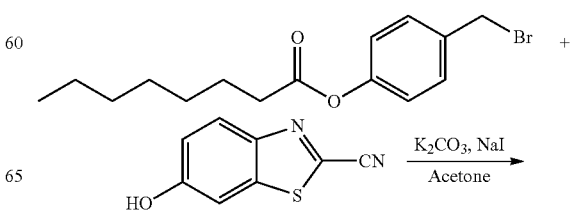

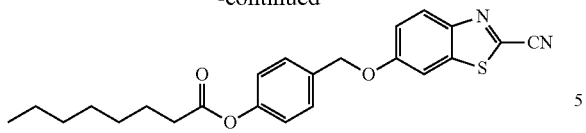

4-bromomethyl-phenyl-caprylate (27.7 g/88 mmol/1.2 eq.) and 2-cyano-6-hydroxy-benzothiazole (13.07 g/7 mmol/1 eq) were dissolved in dry acetone (120 mL) and stirred in heating oil bath (80° C.). K2CO₃ (25.6 g/185.2 mmol/2.5 eq) and Sodium Iodide (220 mg/1.5 mmol/2 mol %) were added in one portion. Reaction mixture turned yellow-orange immediately. After 100 min of stirring at reflux temperature TLC control (Petrolether/AcOEt=2/1) showed full conversion. Reaction mixture was let cool down slowly, filtered through S3 fritt, washed with 30 ml of Acetone and concentrated on vacuo. Residue was dissolved in 200 mL and washed with 100 mL H2O and brine. Organic layer was dried over Na₂SO₄, filtered through S3 fritt and concentrated on vacuo. Residue was crystallized from MTBE, then from EtOH. Product was isolated as white powder (13.3 g/37% yield).

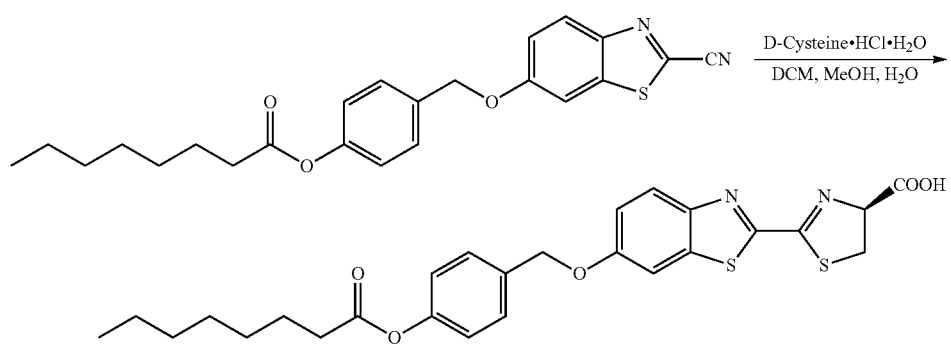

1.3 g of Starting material (1.3 g/3.18 mmol/1 eq) was dissolved in mixture of DCM (30 mL) and MeOH (30 mL). After dissolving of solid, 10 mL of water were added. Obtained solution was bubbled with Argon for 15 minutes. Cysteine hydrochloride monohydrate (592 mg/3.37 mmol/1.06 eq) was added and dissolved during approx 3 min. K2CO₃ (474 mg/3.43 mmol/1.06 eq) was dissolved in 5 mL of demi water and bubbled with Argon for 15 minutes. Solution of K2CO₃ was added in one portion to solution of benzothiazole derivative. Resulting yellowish solution got turbid. Mixture was stirred at room temperature under Argon. TLC (Petrolether/AcOEt=2/1) control after 90 minutes showed full conversion of starting material. Reaction mixture was partly evaporated on rotavap until some yellowish solid were formed. 1M HCl was used to set pH of resulting mixture to 1-2. To residue water (200 mL) was added and resulting solution was extracted with DCM (3×150 mL). Organic layer was dried over Na₂SO₄, filtered through S3 fritt and concentrated on vacuo. Resulting yellow amorphous solid was crystallised from EtOH. Crystallised product was isolated in form of yellowish powder (1.16 g/71% yield).

Other compounds discloses herein were synthesized according to procedures as set out above by a respective selection of the starting materials.

Synthesis Example 8: Synthesis of Compounds a and C Used in Example 13

General Synthetic Scheme

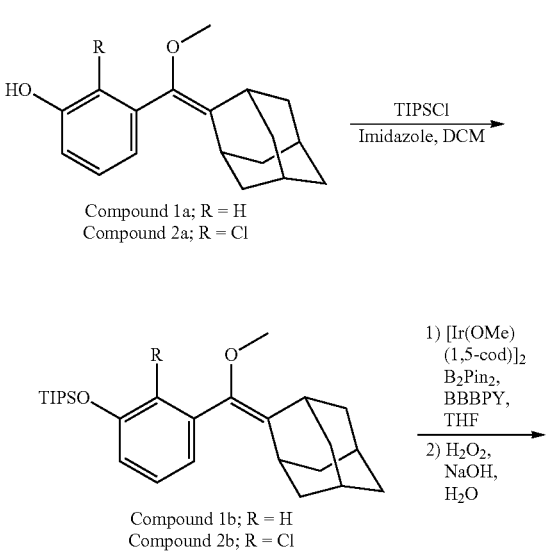

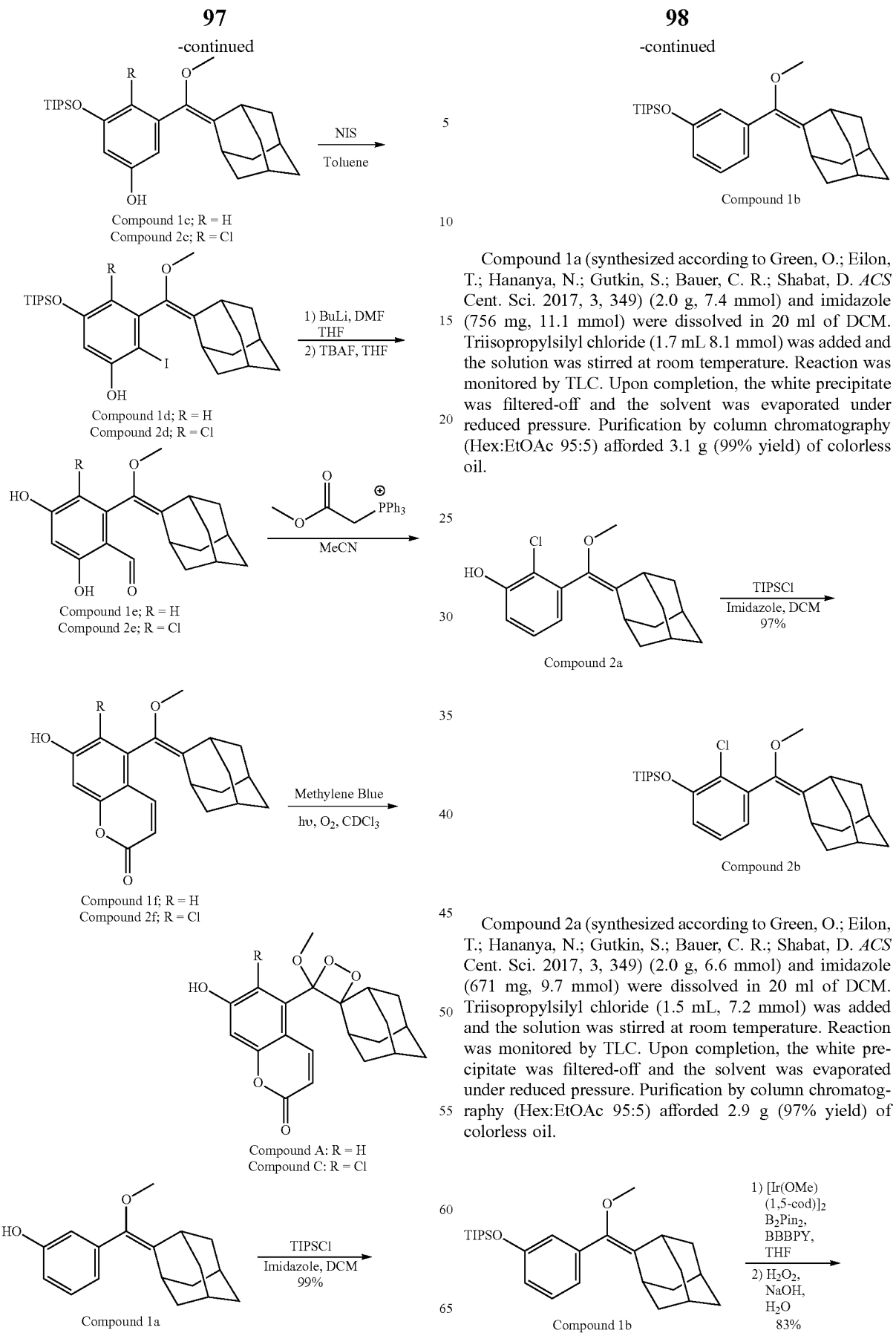

Compound 1a (synthesized according to Green, O.; Eilon, T.; Hananya, N.; Gutkin, S.; Bauer, C. R.; Shabat, D. *ACS Cent. Sci.* 2017, 3, 349) (2.0 g, 7.4 mmol) and imidazole (756 mg, 11.1 mmol) were dissolved in 20 ml of DCM. Triisopropylsilyl chloride (1.7 mL 8.1 mmol) was added and the solution was stirred at room temperature. Reaction was monitored by TLC. Upon completion, the white precipitate was filtered-off and the solvent was evaporated under reduced pressure. Purification by column chromatography (Hex:EtOAc 95:5) afforded 3.1 g (99% yield) of colorless oil.

Compound 2a (synthesized according to Green, O.; Eilon, T.; Hananya, N.; Gutkin, S.; Bauer, C. R.; Shabat, D. *ACS Cent. Sci.* 2017, 3, 349) (2.0 g, 6.6 mmol) and imidazole (671 mg, 9.7 mmol) were dissolved in 20 ml of DCM. Triisopropylsilyl chloride (1.5 mL, 7.2 mmol) was added and the solution was stirred at room temperature. Reaction was monitored by TLC. Upon completion, the white precipitate was filtered-off and the solvent was evaporated under reduced pressure. Purification by column chromatography (Hex:EtOAc 95:5) afforded 2.9 g (97% yield) of colorless oil.

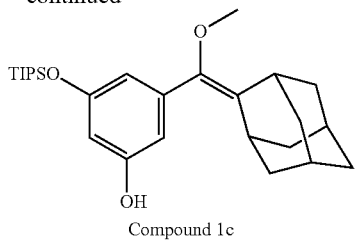

Compound 1c

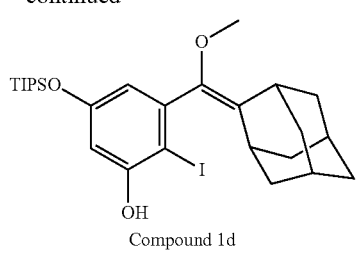

Compound 1d

Compound 1b (2.00 g, 4.7 mmol), bis(pinacolato)diboron (2.14 g, 8.44 mmol), (1,5-cyclooctadiene)(methoxy)iridium (I) dimer (63 mg, 0.93 mmol) and 4,4'-Di-tert-butyl-2,2'-dipyridyl (51 mg, 0.189 mmol) were dissolved in 20 ml of anhydrous THF in a sealed tube. Reaction mixture was stirred at 80° C. for 2 hours, and was monitored Upon completion, the solvent was evaporated under reduced pressure. The crude product was passed through silica gel column (Hex:EtOAc 65:35) to afford 1.73 g (83% yield) of white solid that was taken to the next step without further purification.

Compound 1c (1.5 g, 3.40 mmol) was dissolved in 150 ml of Toluene and cooled to 0° C. N-Iodosuccinimide (635 mg, 2.81 mmol) was added in portions. Reaction was monitored by TLC. Upon completion, the solvent was evaporated under reduced pressure. Purification by column chromatography (Hex:EtOAc 90:10) afforded 900 mg (47% yield) of white solid.

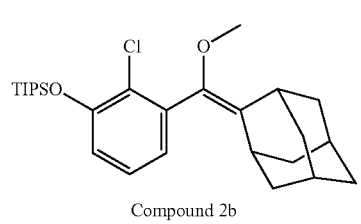

Compound 2b

1) [Ir(OMe)(1,5-cod)]$_2$
B$_2$Pin$_2$,
BBBPY,
THF
2) H$_2$O$_2$, NaOH, H$_2$O
89%

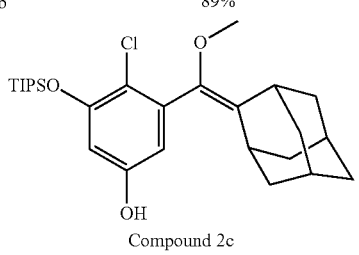

Compound 2c

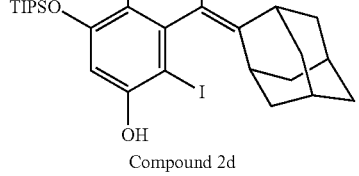

Compound 2c

NIS
Toluene
51%

Compound 2b (2.00 g, 4.3 mmol), bis(pinacolato)diboron (1.97 g, 7.76 mmol), (1,5-cyclooctadiene)(methoxy)iridium (I) dimer (58 mg, 0.856 mmol) and 4,4'-Di-tert-butyl-2,2'-dipyridyl (47 mg, 0.173 mmol) were dissolved in 20 ml of anhydrous THF in a sealed tube. Reaction mixture was stirred at 80° C. for 2 hours, and was monitored Upon completion, the solvent was evaporated under reduced pressure. The crude product was passed through silica gel column (Hex:EtOAc 70:30) to afford 1.84 g (89% yield) of white solid that was taken to the next step without further purification.

Compound 2c (1.5 g, 3.16 mmol) was dissolved in 150 ml of Toluene and cooled to 0° C. N-Iodosuccinimide (592 mg, 2.63 mmol) was added in portions. Reaction was monitored by TLC. Upon completion, the solvent was evaporated under reduced pressure. Purification by column chromatography (Hex:EtOAc 90:10) afforded 967 mg (51% yield) of white solid.

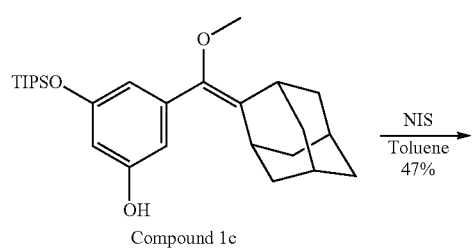

Compound 1c

NIS
Toluene
47%

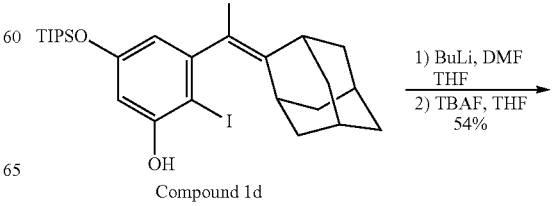

Compound 1d

1) BuLi, DMF
THF
2) TBAF, THF
54%

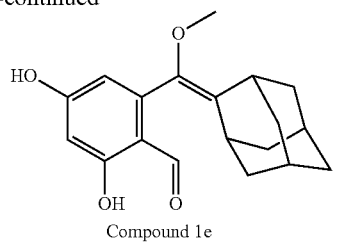

Compound 1e

Compound 1d (900 mg, 1.58 mmol) was dissolved in THF (5 mL) under N₂ atmosphere. The solution was cooled to −78° C. and n-BuLi (2.54 mL, 2.5 M in Hex) was added. After 15 min of stirring, DMF (440 μL) was added. The reaction mixture was heated to room temperature with stirring for 30 min and monitored by TLC. After completion, saturated solution of ammonium chloride (5 mL) was added. The mixture was extracted with EtOAc (3×30 mL). The combined organic layer was washed with brine (50 mL), dried over Na₂SO₄ and evaporated under reduced pressure. Then, the crude reside was dissolved in THF (10 mL) and TBAF (3.2 mL, 2.5M in THF) was added. Upon full conversion, saturated solution of ammonium chloride (5 mL) was added. The mixture was extracted with EtOAc (3×30 mL). The combined organic layer was washed with brine (25 mL), dried over Na₂SO₄ and evaporated under reduced pressure. The product was purified by column chromatography to give 269 mg (54% yield) of yellow solid.

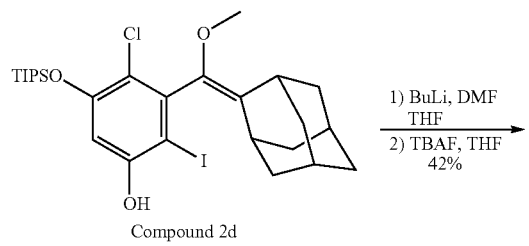

Compound 2d (900 mg, 1.50 mmol) was dissolved in THF (5 mL) under N₂ atmosphere. The solution was cooled to −78° C. and n-BuLi (2.41 mL, 2.5 M in Hex) was added. After 15 min of stirring, DMF (418 μL) was added. The reaction mixture was heated to room temperature with stirring for 30 min and monitored by TLC. After completion, saturated solution of ammonium chloride (5 mL) was added. The mixture was extracted with EtOAc (3×30 mL). The combined organic layer was washed with brine (50 mL), dried over Na₂SO₄ and evaporated under reduced pressure. Then, the crude reside was dissolved in THF (10 mL) and TBAF (3.0 mL, 2.5M in THF) was added. Upon full conversion, saturated solution of ammonium chloride (5 mL) was added. The mixture was extracted with EtOAc (3×30 mL). The combined organic layer was washed with brine (25 mL), dried over Na₂SO₄ and evaporated under reduced pressure. The product was purified by column chromatography to give 218 mg (42% yield) of yellow solid.

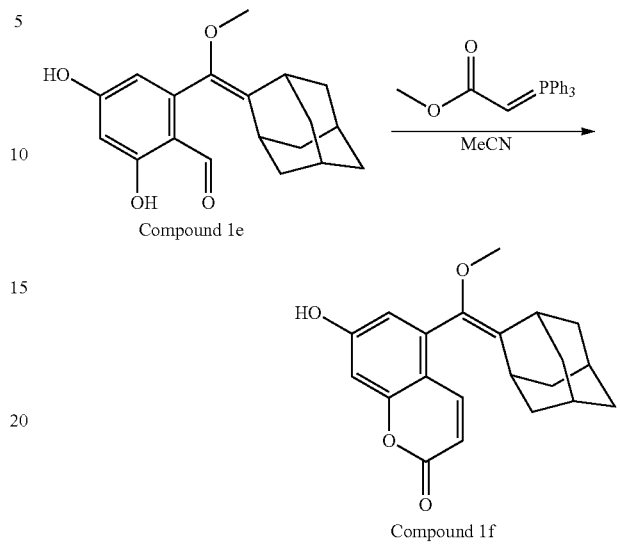

Compound 1e (150 mg, 0.48 mmol) and methyl (triphenylphosphoranylidene)acetate (191 mg, 0.57 mmol) were dissolved in MeCN (3 mL) and the mixture was heated to reflux while monitored by RP-HPLC (gradient of ACN in water, 0.1% TFA). Upon full consumption of the starting material the reaction mixture was cooled, diluted with EtOAc (100 mL), washed with brine (50 ml). The organic layer was dried over Na₂SO₄ and evaporated under reduced pressure. The product was purified by column chromatography to give 111 mg (69% yield) of yellow solid.

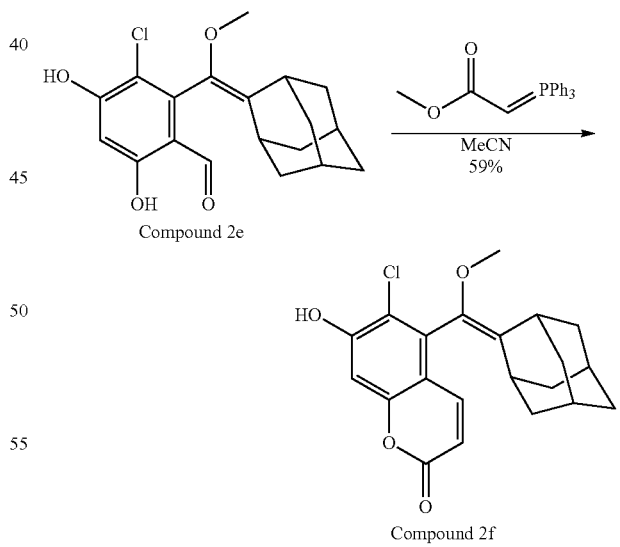

Compound 2e (150 mg, 0.43 mmol) and methyl (triphenylphosphoranylidene)acetate (172 mg, 0.51 mmol) were dissolved in MeCN (3 mL) and the mixture was heated to reflux while monitored by RP-HPLC (gradient of ACN in water, 0.1% TFA). Upon full consumption of the starting material the reaction mixture was cooled, diluted with EtOAc (100 mL), washed with brine (50 ml). The organic layer was dried over Na$_2$SO$_4$ and evaporated under reduced pressure. The product was purified by column chromatography to give 94 mg (59% yield) of yellow solid.

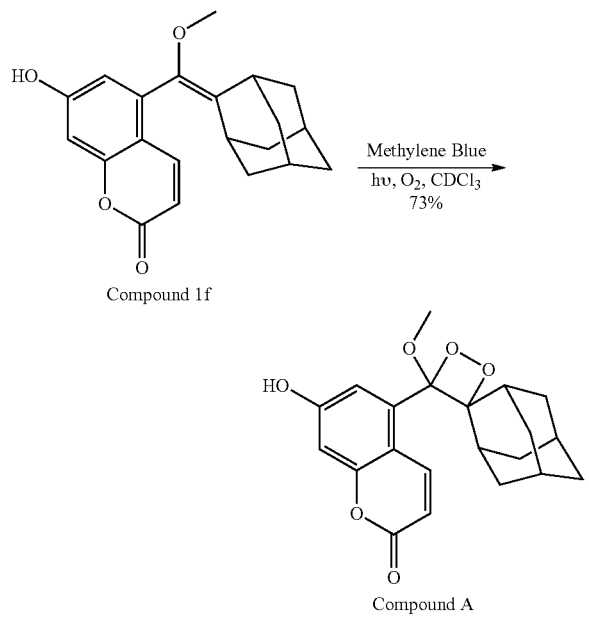

Compound 1f (50 mg, 0.15 mmol) and a catalytic amount of methylene blue were dissolved in 20 mL of DCM. Then, oxygen was bubbled through the solution while irradiating with yellow light. The reaction was monitored by RP-HPLC. Upon completion (10 min), the solvent was concentrated under reduced pressure and the product was purified by preparative RP-HPLC (gradient of ACN in water, 0.1% TFA). The product was obtained as a white solid (40 mg, 73%).

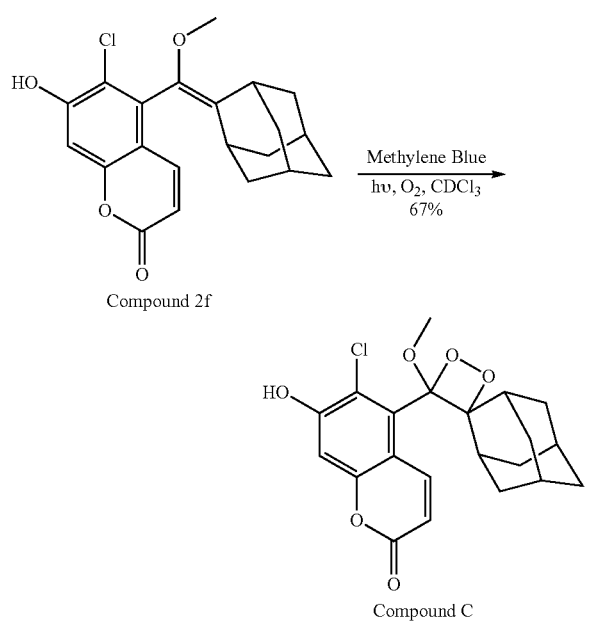

Compound 2f (50 mg, 0.13 mmol) and a catalytic amount of methylene blue were dissolved in 20 mL of DCM. Then, oxygen was bubbled through the solution while irradiating with yellow light. The reaction was monitored by RP-HPLC. Upon completion (10 min), the solvent was concentrated under reduced pressure and the product was purified by preparative RP-HPLC (gradient of ACN in water, 0.1% TFA). The product was obtained as a white solid (36 mg, 67%).

Example 1

Enzymatic Assay of Pig Liver Esterase Activity with Compound IIa

Compound IIa was added to a final concentration of 62.5 µM to phosphate-buffered saline (pH 7.4) containing 10% v/v dimethyl sulfoxide. The assay mix was pre-incubated for 20 min at room temperature, then 1:5 v/v of pig liver esterase solutions containing varying enzyme concentrations were added and luminescence was recorded for 20 min at room temperature with a SpectraMax M5 reader in luminescence mode. Assays were performed in a black microtiter plate with a total liquid volume of 0.25 mL. Concentration of pig liver esterase and maximal RLU (relative light unit) values within the 20 min measurement period exhibited a positive linear correlation over two orders of magnitude. FIG. 1 shows the results of this Example.

Example 2

Detection of *Salmonella enterica* with Compound IIa

*Citrobacter freundii* ATCC 8090 (C.f., C8E negative), *Escherichia coli* ATCC 25922 (E.c., C8E negative), *Salmonella Typhimurium* (D) ATCC 14028 (S.T., *Salmonella enterica* ssp. I ser. *Typhimurium*, C8E positive), *Salmonella Enteritidis* (D) ATCC 13076 (S.E. 1, *Salmonella enterica* ssp. *enterica* ser. *Enteritidis*, C8E positive) and *Salmonella Enteritidis* RKI 05/07992 (S.E. 2, *Salmonella enterica* ssp. *enterica* ser. *Enteritidis*, C8E positive) were cultivated in Nutrient Broth (5 g/l peptone, 5 g/l NaCl, 2 g/L yeast extract, 1 g/l beef extract, pH 7.4) for 17 h and then serially diluted in sterile saline (0.9% NaCl). Similar cell concentrations of all strains were inoculated in triplicate test tubes with Nutrient Broth. In addition, further dilutions of S.E. 2 cells in sterile saline were inoculated in triplicate test tubes. Sterile saline was added to negative control tubes. After 6 h of cultivation at 37° C. and 150 rpm, samples were withdrawn from cultures (0.205 mL) and mixed with 45 µL of a Compound IIa solution in dimethyl sulfoxide in a white microtiter plate. Final concentration Compound IIa was 10 µM, final concentration of dimethyl sulfoxide was 15% v/v. Light emission was recorded with a plate reader equipped with a luminescence detection system. Mean RLU (relative light unit) values of the time period 27-30 min after addition of chemiluminescent substrate were compared (Table 3). At a similar inoculation density of 105 CFU/mL, the tested *Salmonella* strains showed 35 to 60-fold higher light emission than *Citrobacter freundii* and 65 to 111-fold higher light emission than *Escherichia coli*. It was possible to detect 10 CFU/mL of *Salmonella Enteritidis* after 6 h of incubation as indicated by a signal-to-noise ratio of 2 relative to sterile controls.

TABLE 3

Luminescence of *Salmonella enterica* culture samples 5 after addition of Compound IIa compared to other bacterial species

| Inoculation density (CFU/mL) | Organism | Mean RLU (n = 3) | Standard error (%, n = 3) | Signal to noise ratio (to sterile) |
|---|---|---|---|---|
| $10^5$ | C.f. | 6480 | 7 | 12 |
| $10^5$ | E.c. | 3504 | 11 | 6 |
| $10^5$ | S.T. | 228202 | 13 | 283 |
| $10^5$ | S.E. 1 | 158262 | 6 | 408 |
| $10^5$ | S.E. 2 | 387911 | 19 | 693 |
| $10^4$ | S.E. 2 | 154011 | 8 | 275 |
| $10^3$ | S.E. 2 | 40236 | 9 | 72 |
| $10^2$ | S.E. 2 | 5100 | 5 | 9 |
| $10^1$ | S.E. 2 | 1041 | 3 | 2 |
| 0 | sterile | 560 | 13 | 1 |

Example 3

Enzymatic Assay of PI-PLC Activity with Compound IIIa

Compound IIa was added to a final concentration of 10 µM to phosphate-buffered saline (pH 7.4) containing 1% v/v dimethyl sulfoxide. Varying concentrations of phosphatidylinositol-specific phospholipase C (PI-PLC) were added and luminescence was recorded at room temperature (Table 4). Assays were performed in a white microtiter plate with 0.25 mL total liquid volume. Concentration of PI-PLC and maximal RLU (relative light unit) values within a 20 min measurement period exhibited a positive correlation over two orders of magnitude.

TABLE 4

Measurement of PI-PLC activity with Compound IIIa

| PI-PLC added (U/mL) | RLU | Signal to noise ratio |
|---|---|---|
| $5 \cdot 10^{-1}$ | 60265 | 862 |
| $5 \cdot 10^{-2}$ | 35822 | 512 |
| $5 \cdot 10^{-3}$ | 10369 | 148 |
| $5 \cdot 10^{-4}$ | 1191 | 17 |
| w/o enzyme | 70 | 1 |

Example 4

Detection of *Listeria monocytogenes* with Compound IIIa

*Listeria monocytogenes* ATCC 7644 (L.m. 1, PI-PLC positive), *Listeria monocytogenes* (4b) ATCC 19115 (L.m. 2, PI-PLC positive), *Listeria innocua* (6a) ATCC 33090 (L.i., PI-PLC negative) and *Escherichia coli* ATCC 25922 (E.c., PI-PLC negative) were cultivated in M52 broth (1.35 g/L potassium dihydrogen phosphate, 9.6 g/L disodium hydrogen phosphate, 1.11 g/L sodium pyruvate, 6 g/L yeast extract, 17 g/L tryptone, 3 g/L phytone, 5 g/L sodium chloride, 2.5 g/L glucose, pH 7.3) for 19 h and then serially diluted in sterile saline (0.9% NaCl). Similar cell concentrations of all strains were inoculated in triplicate test tubes with M52 broth. In addition, further dilutions of L.m. 2 cells in sterile saline were inoculated in triplicate test tubes. Sterile saline was added to negative control tubes. After 6 h of cultivation at 37° C. and 150 rpm, samples were withdrawn from cultures (0.99 mL) and mixed with 1 µL Compound IIIa solution in dimethyl sulfoxide in a white microtiter plate. Final concentration of Compound IIIa was 10 µM, final concentration of dimethyl sulfoxide was 1% v/v. Light emission was recorded with a plate reader equipped with a luminescence detection system. Mean RLU (relative light unit) values of the time period 16-20 min after addition of chemiluminescent substrate were compared (Table 5). At a similar inoculation density of 105 CFU/mL, the tested *Listeria monocytogenes* strains showed 311 to 361-fold higher light emission than *Listeria innocua* and 1465 to 1702-fold higher light emission than *Escherichia coli*. It was possible to detect 103 CFU/mL of *Listeria monocytogenes* after 6 h of incubation as indicated by a signal-to-noise ratio of 2 relative to sterile controls.

TABLE 5

Detection of *Listeria monocytogenes* with Compound IIIa

| Inoculation density (CFU/mL) | Organism | Mean RLU (n = 3) | Standard error (%, n = 3) | Signal to noise ratio (to sterile) |
|---|---|---|---|---|
| $10^5$ | L.i. | 33 | 8.3 | 2.3 |
| $10^5$ | E.c. | 7 | 5.7 | 0.5 |
| $10^5$ | L.m. 1 | 11913 | 1.7 | 832 |
| $10^5$ | L.m. 2 | 10258 | 9.0 | 716 |
| $10^4$ | L.m. 2 | 242 | 9.0 | 17 |
| $10^3$ | L.m. 2 | 31 | 2.7 | 2.2 |
| $10^2$ | L.m. 2 | 12 | 2.9 | 0.9 |
| 0 | sterile | 14 | 6.9 | 1 |

Example 5

Comparison of Detection of *Salmonella enterica* with Compound IIIa and 4-Methylumbelliferyl Caprylate

*Salmonella Enteritidis* RKI 05/07992 was cultivated in Nutrient Broth (5 g/l peptone, 5 g/l NaCl, 2 g/L yeast extract, 1 g/l beef extract, pH 7.4) for 20 h (37° C., 150 rpm) and then serially diluted in phosphate buffered saline. Cell suspensions were mixed 1:1 v/v with phosphate buffered saline containing dimethyl sulfoxide (final concentration in assay 15%) and either Compound IIa (final concentration 10 µM) or 4-Methylumbelliferyl caprylate (MUCAP, final concentration 0.1 mM). Assays were performed in microplates, total liquid volume was 0.2 mL. Light emission and fluorescence (excitation 360 nm, emission 455 nm) were recorded with a SpectraMax M5 (Molecular Devices, Sunnyvale, Calif., USA) plate reader. Cell concentration of undiluted culture was estimated from optical density (600 nm). Conclusion: The limit of detection for *Salmonella enterica* was 625-fold lower when using Compound IIa instead of MUCAP.

Figure 2:
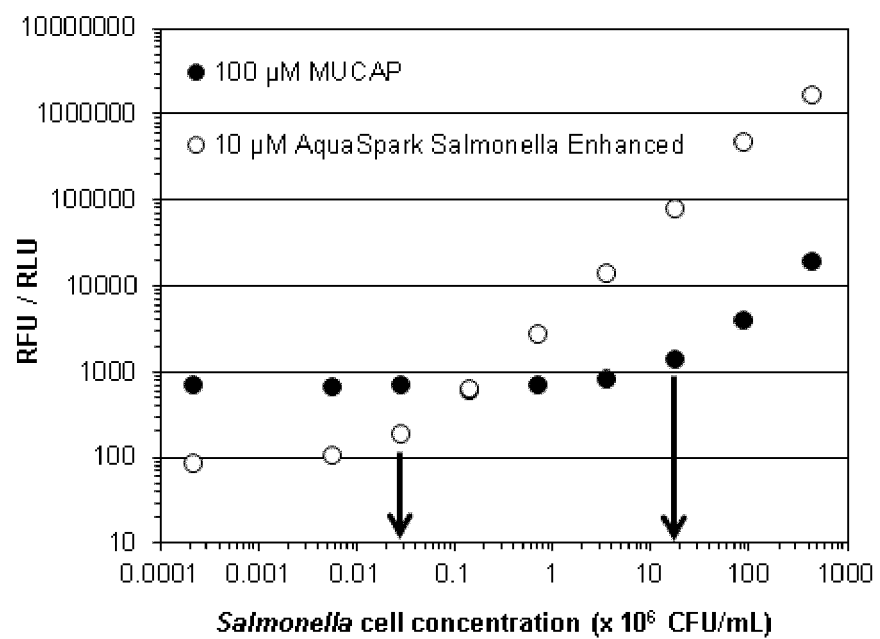
FIG. 2 shows the limits of detection of *Salmonella enterica* using either luminogenic Compound IIa (open symbols) or fluorogenic substrate 4-Methylumbelliferyl caprylate (MUCAP) (closed symbols).

FIG. 2 shows the limits of detection of *Salmonella enterica* using either luminogenic Compound IIa (open symbols) or fluorogenic substrate MUCAP (closed symbols).

Example 6

Detection of *Staphylococcus aureus* with Compound IVa

*Staphylococcus aureus* ATCC 29213 (S.a., phosphatase positive) and *Staphylococcus haemolyticus* RKI 06-01354 (S.h., weak phosphatase activity) were cultivated in Nutrient Broth (5 g/l peptone, 5 g/l NaCl, 2 g/L yeast extract, 1 g/l beef extract, pH 7.4) for 17 h and then serially diluted in sterile saline (0.9% NaCl). Similar cell concentrations of S.a. and S.h. were inoculated in triplicate test tubes with Nutrient Broth. In addition, four further serial dilutions of S.a. cells in sterile saline were inoculated in triplicate test tubes. Sterile saline was added to negative control tubes. After 6 h of cultivation at 37° C. and 150 rpm, samples were withdrawn from cultures (0.196 mL) and mixed with 4 µL Compound IVa solution in dimethyl sulfoxide in a white microtiter plate. Final concentration of Compound IVa was 10 µM, final concentration of dimethyl sulfoxide was 2% v/v. Light emission was recorded with a plate reader equipped with a luminescence detection system. Mean RLU (relative light unit) values of the time period 15-20 min after addition of chemiluminescent substrate were compared (Table 6). Conclusion: *Staphlyococcus aureus* can be detected with high sensitivity using Compound IVa.

TABLE 6

Luminescence of *Staphylococcus* culture samples after addition of Compound IVa

| Inoculation density (CFU/mL) | Organism | Mean RLU, 6 h (n = 3) | Standard error (%, n = 3) | Signal to noise ratio (to sterile) |
| --- | --- | --- | --- | --- |
| $10^5$ | S.h. | 9550 | 10 | 20 |
| $10^5$ | S.a. | 53190 | 18 | 112 |
| $10^4$ | S.a. | 407697 | 4 | 859 |
| $10^3$ | S.a. | 95498 | 4 | 201 |
| $10^2$ | S.a. | 7563 | 2 | 16 |
| $10^1$ | S.a. | 1439 | 15 | 3 |
| 0 | sterile | 474 | 4 | 1 |

Example 7

Monitoring of Pasteurization of Milk with Compound IVa

Figure 3:
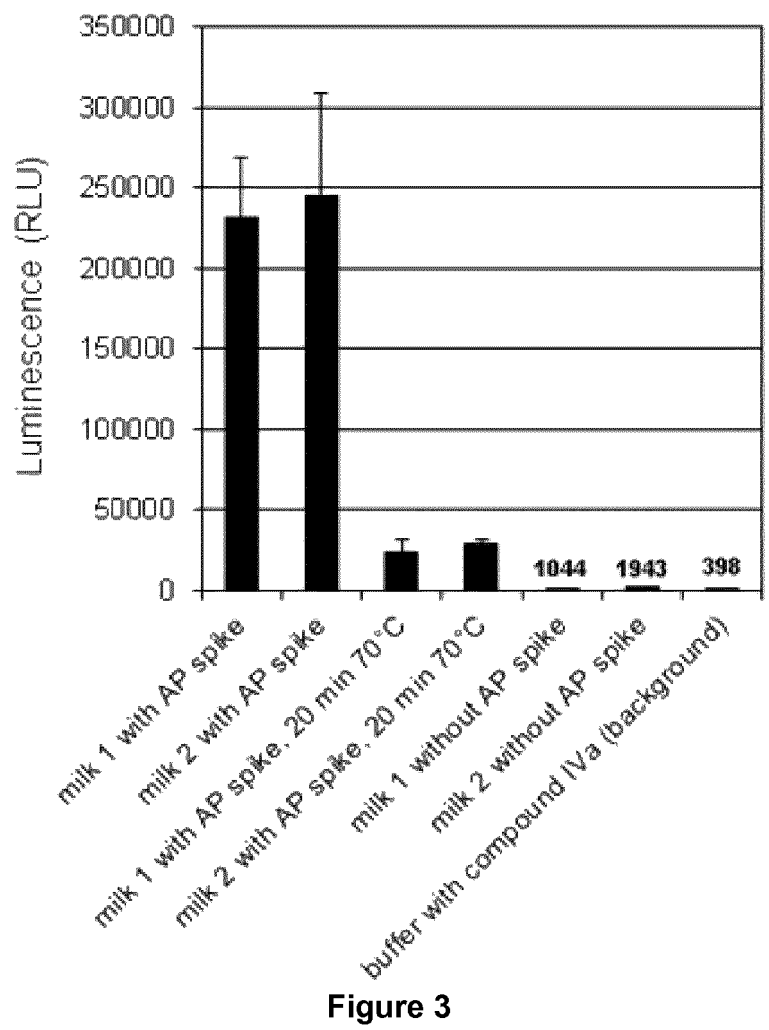
FIG. 3 shows chemiluminometric analysis of the effect of pasteurization on alkaline phosphatase (AP) activity in milk using Compound IVa. Mean values and standard deviations of n=3 replicate experiments

UHT whole milk (milk 1) and pasteurized whole milk (milk 2) were obtained from a Swiss super market. Alkaline phosphatase (AP) from calf intestine was added to milk samples at a final concentration of 0.5 U/mL. Triplicate milk samples in polypropylene test tubes (spiked with alkaline phosphatase) were heated for 20 min at 70° C. in a water bath, similar reference samples were kept at room temperature. Alkaline phosphatase activity of heated and non-heated milk samples was analyzed in a white microtiter plate by adding 2:1 v/v detection mix (20 µM of compound IVa, 100 mM Tris(hydroxymethyl)-aminomethane hydrochloride pH 9.7, 1 mM magnesium chloride, pre-incubated for 20 min at room temperature). Luminescence was recorded with a SpectraMax M5 plate reader, total assay volume was 0.3 mL. Mean RLU (relative light unit) values of pasteurized milk samples were 8 to 10-fold lower compared to samples kept at room temperature (FIG. 3: Chemiluminometric analysis of the effect of pasteurization on alkaline phosphatase activity in milk using Compound IVa. Mean values and standard deviations of n=3 replicate experiments). It was also possible to detect residual alkaline phosphatase activity in non-spiked milk, and the measured RLU values indicated that alkaline phosphatase activity in UHT milk (milk 1) was lower than that in pasteurized milk (milk 2).

Conclusion: Compound IVa and related compounds are suitable for the monitoring of milk pasteurization and similar processes.

Example 8

Figure 4:
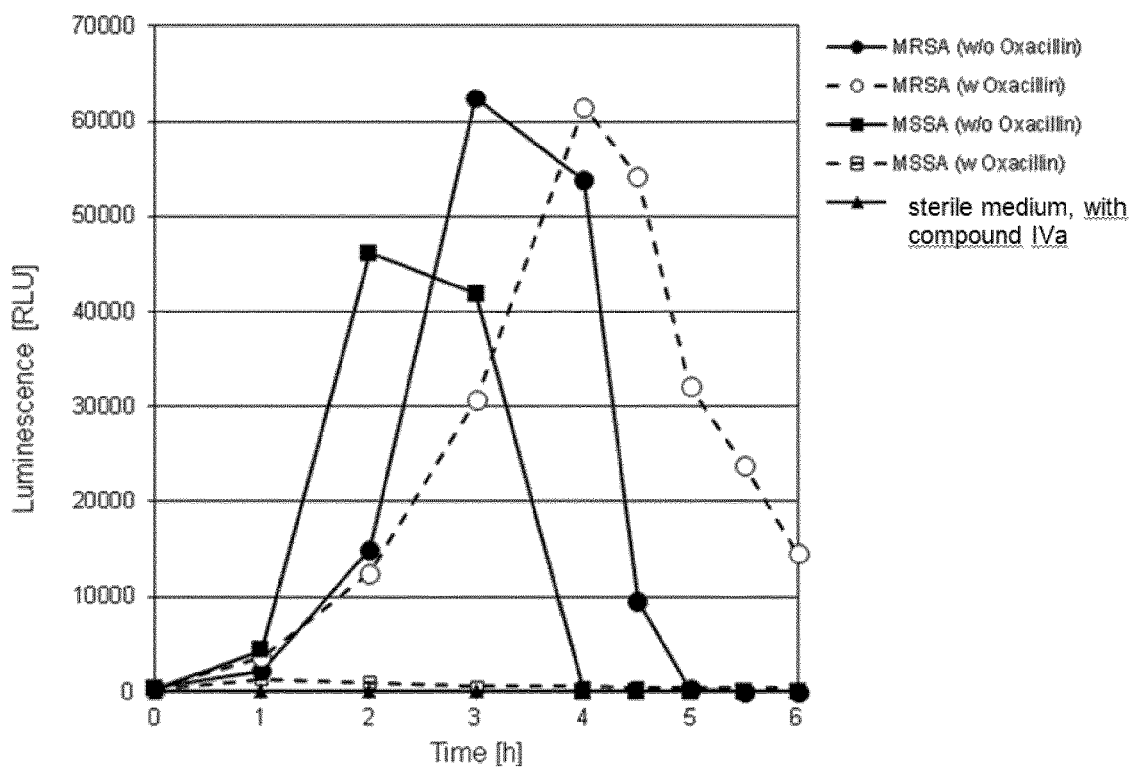
FIG. 4 shows luminescence development in cultures of methicillin-resistant *Staphylococcus aureus* (MRSA) and methicillin-susceptible *Staphylococcus aureus* ATCC 29213 (MSSA) in the presence and absence of the antibiotic oxacillin.

Detection of Methicillin-Resistant *Staphylococcus aureus* (MRSA) with Compound IVa Methicillin-resistant *Staphylococcus aureus* ATCC 33592 (MRSA), a strain which is resistant to penicillin derivatives such as methicillin and oxacillin, and methicillin-susceptible *Staphylococcus aureus* ATCC 29213 (MSSA) were cultivated overnight at 37° C. in nutrient broth (5 g/L peptone, 5 g/L sodium chloride, 2 g/L yeast extract, 1 g/L meat extract, pH 7.4) and diluted in sterile saline. MRSA and MSSA strains were inoculated at approx. $10^6$ CFU/mL in nutrient broth containing compound IVa at a final concentration of 10 µM. For each strain, one culture was supplemented with oxacillin (20 mg/L final concentration) and one culture was left without antibiotics. Tube cultures were incubated at 37° C. and 150 rpm. A sterile control (nutrient broth with 10 µM of compound IVa) was incubated in parallel. Luminescence of culture samples (0.2 mL in a white microtiter plate) was recorded at regular intervals for 6 h with a SpectraMax M5 plate reader (FIG. 4: Luminescence development in cultures of MRSA and MSSA in the presence and absence of the antibiotic oxacillin). The time course of luminescence intensity indicated that the MRSA strain multiplied both in the presence and the absence of oxacillin, while the MSSA strain showed an increase in luminescence only in the antibiotic-free culture. Growing and non-growing cultures could be distinguished after 1 h of incubation.

Conclusion: compound IVa and related compounds are suitable for the detection of methicillin resistant *S. aureus* (MRSA) in a short time (1 to 2 h).

Example 9

Detection of *Escherichia coli* with Compound Va and Comparison to D-Luciferin-6-O-Beta-D-Galactopyranoside

*Escherichia coli* ATCC 25922 (E.c., beta-galactosidase positive) and *Salmonella Enteritidis* RKI 05/07992 (S.E., beta-galactosidase negative) were cultivated in Nutrient Broth for 17 h and then serially diluted in sterile saline (0.9% NaCl). Diluted cell suspensions were inoculated 1:100 v/v in test tubes with either full-strength LB medium (10 g/L tryptone, 5 g/L yeast extract, 5 g/L NaCl) or LB medium diluted 1:20 v/v with ultrapure water (LB1:20). All media contained 1 mM IPTG for induction of beta-galactosidase. Sterile saline was added to negative control tubes. After 6 h of cultivation at 37° C. and 150 rpm, samples (0.255 mL) were withdrawn from cultures and mixed with 45 µL stock solution of compound Va in ethanol in a white microtiter plate. Final concentration of compound Va was 20 µM, final concentration of ethanol was 15% v/v. Light emission was recorded with a SpectraMax M5 plate reader. Mean RLU (relative light unit) values of the time period 9-10 min after addition of chemiluminescent substrate were compared (Table Via). For comparison, the same *E. coli* strain was pre-cultured and diluted in a similar way and then inoculated in diluted Mueller-Hinton broth (MH1:20, full-strength medium diluted 1:20 v/v with 20 mM phosphate buffer pH 7.2). The medium was supplemented with 1 mM IPTG. After 6 h of cultivation at 37° C. and 150 rpm, culture samples (45 µL) were transferred to a microtiter plate and mixed with 5 µL of 10x lysis reagent which contained 2% w/v dodecyl-trimethylammonium bromide, 1 mM D-Luciferin-6-O-beta-D-galactopyranoside (commercially available, Biosynth Cat. No. L-8600) and 10 mM magnesium chloride. Lysis and reaction with D-Luciferin-6-O-beta-D-galactopyranoside was carried out for 1 h at 37° C. Then 0.2 mL of luciferase assay mix was added (5:1 v/v). The assay mix contained 62.5 mM Tris acetate (pH 7.8), 12.5 mM magnesium sulfate, 2.5 g/L bovine serum albumin, 7.5 mM D/L-cysteine, 1.25 mM ethylene diamine tetraacetate, 25 µM sodium pyrophosphate, 10 g/L cyclodextrin, 1.25 mM adenosine 5-triphosphate and 13.1 µg/mL commercially available Photinus pyralis luciferase (recombinant). Light emission was recorded with a SpectraMax M5 plate reader. The mean relative light units (RLU) of the first two minutes of measurement are shown in Table VIb.

Conclusion: The signal to noise ratio achieved for the lowest tested inoculation density of $E.$ $coli$ was 9-fold higher when detection of beta-galactosidase relied on compound Va instead of D-Luciferin-6-O-beta-D-galactopyranoside, in spite of using a 5-fold lower working concentration TABLE VIa Luminescence of Escherichia coli culture samples after addition of Compound Va in combination with 15% v/v ethanol

| Inoculation density (CFU/mL) | Organism | RLU, 6 h LB | RLU, 6 h LB1:20 | Signal to noise ratio, LB1:20 (to sterile) |
|---|---|---|---|---|
| $10^6$ | S.E. | 66 | 125 | 1 |
| $10^6$ | E.c. | 18830 | 84511 | 871 |
| $10^5$ | E.c. | 43412 | 164721 | 1698 |
| $10^4$ | E.c. | 49434 | 105252 | 1085 |
| $10^3$ | E.c. | 3317 | 7690 | 79 |
| $10^2$ | E.c. | 551 | 1369 | 14 |
| 0 | sterile | 62 | 97 | 1 |

TABLE VIb

Luminescence of Escherichia coli culture samples after lysis in the presence of Luciferin-6-O-beta-D-qalactopyranoside and addition of luciferase assay mix

| Inoculation density (CFU/mL) | Organism | RLU, 6 h MH1:20 | Signal to noise ratio (to sterile) |
|---|---|---|---|
| $10^6$ | E.c. | 4777613 | 544 |
| $10^4$ | E.c. | 3306967 | 377 |
| $10^2$ | E.c. | 13367 | 1.5 |
| 0 | sterile | 8780 | 1 |

Example 10

Detection of Salmonella enterica with D-Luciferin-6-O-Phenyl-Caprylate

D-luciferin-6-O-phenyl-caprylate was synthesized according to procedures known to persons skilled in the art. Salmonella Enteritidis RKI 05/07992 (S.E., Salmonella enterica ssp. enterica ser. Enteritidis, C8 esterase positive) was cultivated in Nutrient Broth (5 g/L peptone, 5 g/L NaCl, 2 g/L yeast extract, 1 g/L yeast extract, pH 7.4) for 16 h and then serially diluted in sterile saline (0.9% NaCl). Diluted cell suspensions were inoculated 1:100 v/v in test tubes with Nutrient Broth containing 0.1 mM D-luciferin-6-O-phenyl-caprylate. After 6.5 h of cultivation at 37° C. and 150 rpm, samples (50 µL) were withdrawn from cultures and mixed with 0.2 mL luciferase assay mix (composition described in example 9) in a microtiter plate. Use of a cell lysis reagent such as dodecyl trimethyl ammonium bromide was not required (data not shown). Light emission was recorded with a plate reader equipped with a luminescence detection system. Mean RLU (relative light unit) values of first 3 min after addition of luciferase assay mix were compared (Table VII).

Conclusion: The signal-to-noise ratio achieved with compound IIa at similar concentrations of Salmonella enterica was 9 to 170-fold higher compared to D-luciferin-6-O-caprylate, facilitating a lower limit of detection (see example 2).

TABLE VII

Luminescence of Salmonella enterica cultures samples containing D-luciferin-6-O-phenyl-caprylate after mixing with luciferase assay mix

| Inoculation density (CFU/mL) | Organism | RLU, 6 h | Signal to noise ratio (to sterile) |
|---|---|---|---|
| $10^6$ | S.E. | 417195 | 24 |
| $10^4$ | S.E. | 27783 | 1.6 |
| $10^2$ | S.E. | 18354 | 1.1 |
| 0 | sterile | 17154 | 1 |

Example 11

Figure 5:
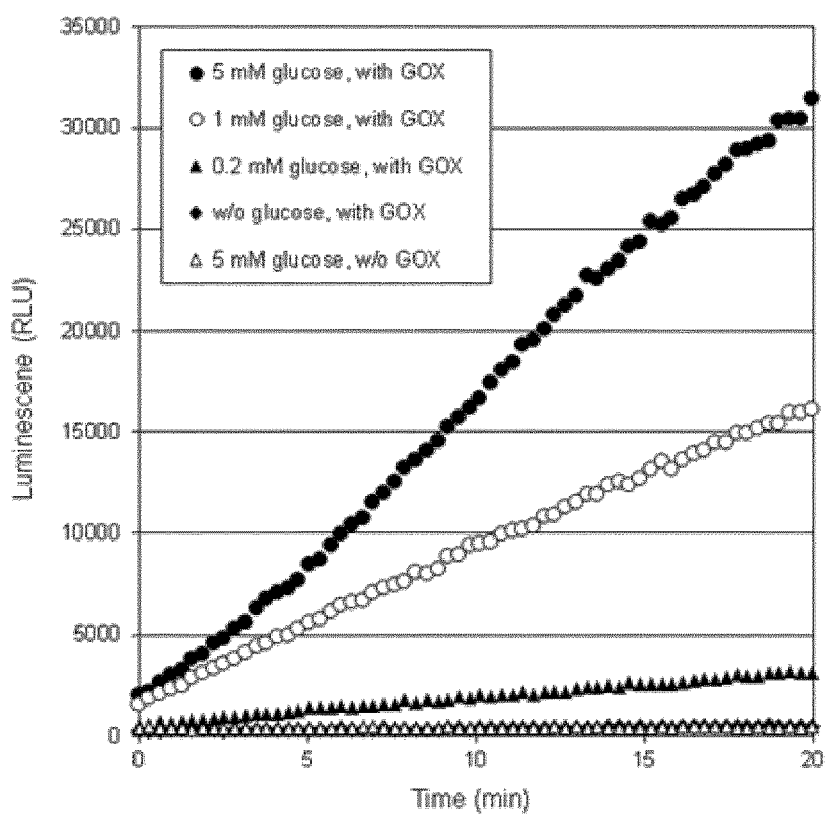
FIG. 5 shows detection of glucose directly in *Escherichia coli* culture supernatants using the hydrogen peroxide-triggered chemiluminescent substrate compound VIa in combination with glucose oxidase (GOX).

Detection of Glucose in Culture Supernatant of Escherichia coli Using Compound Via in Combination with Glucose Oxidase Escherichia coli ATCC 25922 was cultivated in Nutrient Broth (5 g/L peptone, 5 g/L NaCl, 2 g/L yeast extract, 1 g/L yeast extract, pH h 7.4) for 16 h. Cells were separated from culture supernatant by centrifugation (13'000×g, 2 min). Varying concentrations of glucose were added to culture supernatant from 100-fold concentrated stock solutions in water, a similar amount of water was added to the negative control. A second negative control also contained 5 mM glucose, but no glucose oxidase. Culture supernatant with and without glucose (0.1 mL) was mixed in a white microtiter plate with 0.1 mL of HEPES buffer (100 mM, pH 7.0) containing 40 µM of compound VIa, reacting with hydrogen peroxide) and 1 mg/mL commercially available glucose oxidase from Aspergillus niger. The time course of luminescence was recorded for 20 min with a SpectraMAx M5 plate reader, results are shown in FIG. 5 (Detection of glucose directly in Escherichia coli culture supernatants using the hydrogen peroxide-triggered chemiluminescent substrate compound VIa in combination with glucose oxidase (GOX)). Presence of glucose lead to continuously increasing luminescence when compound Via and glucose oxidase were also present. The rate of increase showed a positive correlation with the glucose concentration.

Conclusion: Growth substrates and metabolites such as glucose can be detected directly in supernatants of microbial cultures by chemiluminescence when using compound Via or related compounds in combination with suitable hydrogen peroxide-releasing enzymes (e.g. oxidases).

Example 12

Detection of Carbapenem-Resistant Bacteria with Compound VIIa

Carbapenem resistant bacterial strains Pseudomonas aeruginosa RKI 48/09 (IMP-2) (P.a.-Imp$^R$) and Klebsiella

*pneumoniae* RKI 92/08 (KPC-2) (K.p.-Imp$^R$) were cultivated on trypticase soy agar supplemented with 8 mg/L and 4 mg/mL imipenem, respectively. Carbapenem sensitive strain *Escherichia coli* ATCC 25922 (E.c.) was cultivated on trypticase soy agar. Nutrient broth (for composition and pH see previous examples, 3 mL in 15 mL tubes) with and without imipenem was inoculated with imipenem resistant and sensitive bacteria from agar plates. Tube cultures were incubated for 6 h at 37° C. and 150 rpm. Culture samples (0.255 mL) were transferred to wells of a white microtiter plate and mixed with 45 µL stock solution of compound VIa in ethanol. Final concentrations of compound VIa, ethanol and dimethyl sulfoxide were 10 µM, 14% v/v and 1% v/v, respectively. Luminescence was recorded after addition of compound VIa for 30 min with a plate reader. Maximal luminescence signals (relative light units) of the measurement period are shown in table VII.

Conclusion: Carbapenem resistant bacteria can be distinguished from carbapenem sensitive bacteria by adding compound VIa to culture samples and recording luminescence.

TABLE VII

Luminescence of culture samples of carbapenem resistant and sensitive bacteria after addition of compound VIIa

| Strain | Imipenem (mg/L) | OD$_{600}$ 6 h | RLU max. (with 10 µM VI) | Signal to noise ratio (to E.c.) |
|---|---|---|---|---|
| P.a.-Imp$^R$ | 8 | 0.48 | 21028 | 2.6 |
| P.a.-Imp$^R$ | 0 | 0.67 | 19940 | 2.4 |
| K.p.-Imp$^R$ | 4 | 0.50 | 72272 | 8.8 |
| K.p.-Imp$^R$ | 0 | 0.66 | 72951 | 8.9 |
| E.c. | 4 | 0.01 | 7992 | n.a. |
| E.c. | 0 | 0.73 | 8181 | n.a. |
| Sterile | 0 | 0 | 8812 | n.a. |

Example 13

Luminescent Properties of Compounds Comprising Different Substituents R$^A$, R$^B$ and R$^C$ The chemiluminescence kinetic profile and total light emitted of Compound A, Compound B and Compound C has been determined in PBS buffer solution (10% DMSO), [1 µM], at a pH of 7.4.

Compound A

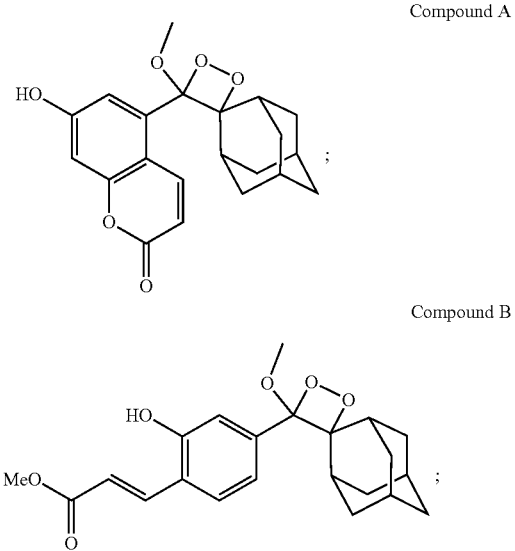

Compound B

Compound C

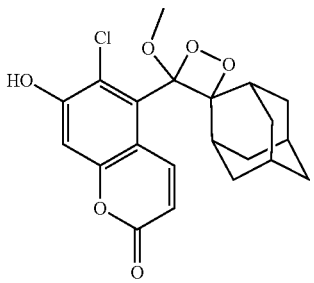

Compounds A, B and C represent the (luminescent) species that is formed from a respective compound of Formula I upon interaction of R$^1$ with an analyte.

Figure 6A:
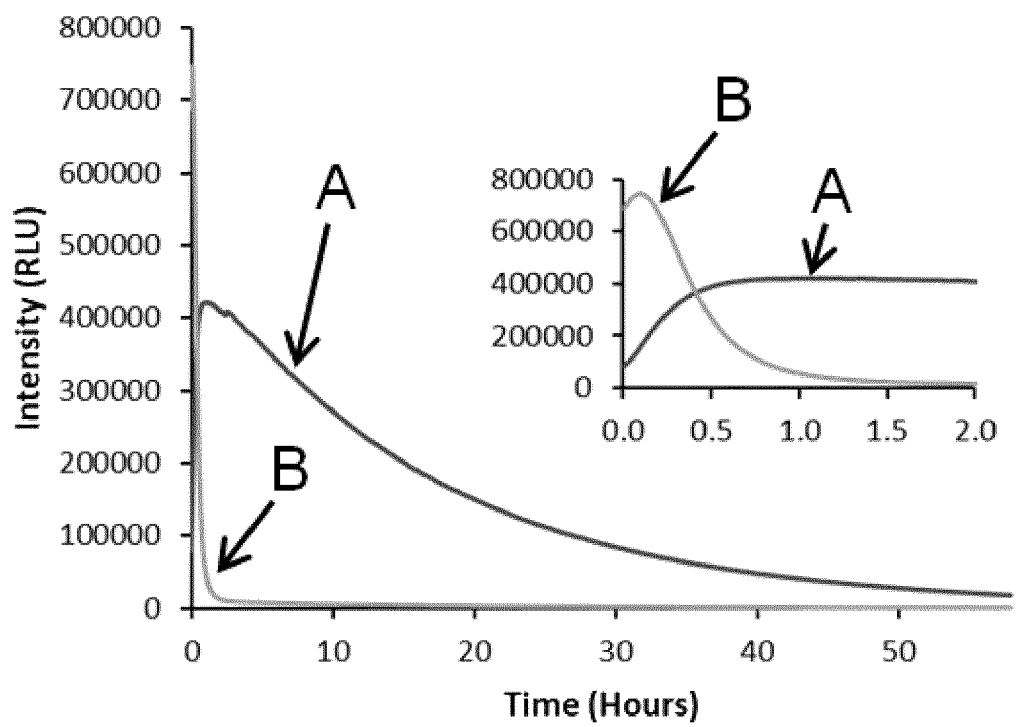
FIGS. 6A-6B show the chemiluminescence kinetic profiles of Compounds A and B (6A; insert: zoom on first 2 hours); and the total light emitted of Compounds A and B (6B).
Figure 6B:
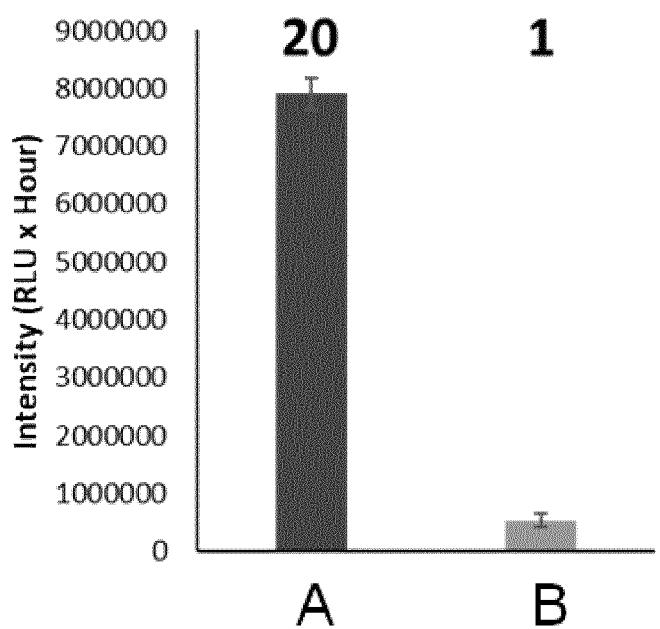

The chemiluminescence kinetic profiles of Compounds A and B are compared in FIG. 6A (insert: zoom on first 2 hours); the total light emitted of Compounds A and B is compared in FIG. 6B.

Figure 7A:
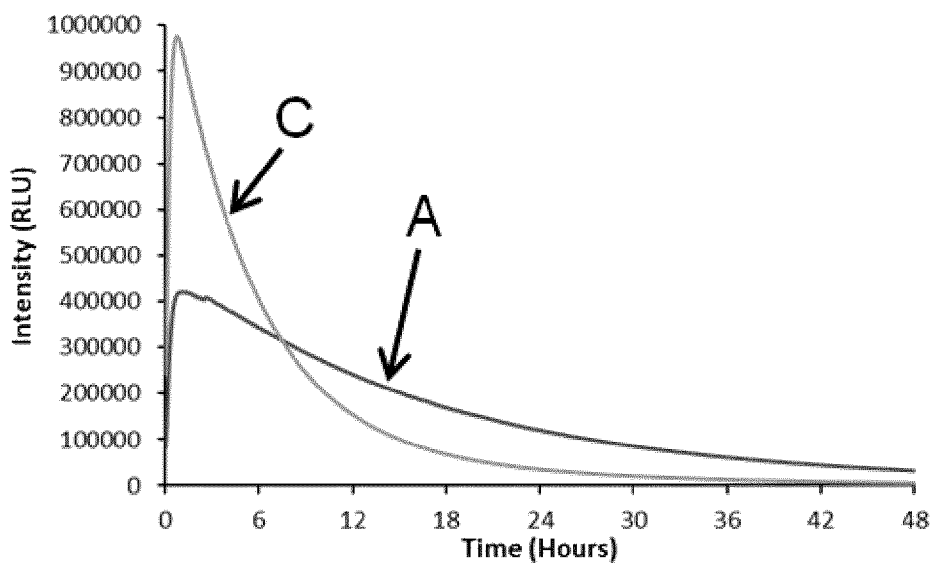
FIGS. 7A-7B the chemiluminescence kinetic profiles of Compounds A and C (7A); and the total light emitted of Compounds A and C (7B).
Figure 7B:
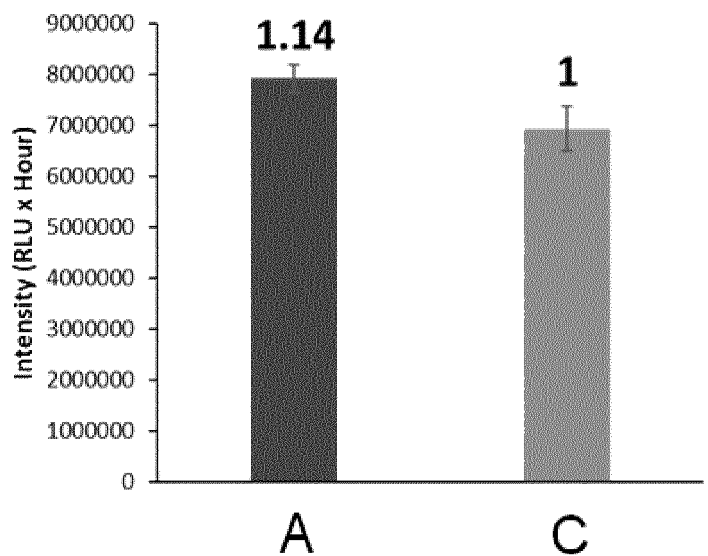

The chemiluminescence kinetic profiles of Compounds A and C are compared in FIG. 7A; the total light emitted of Compounds A and C is compared in FIG. 7B.

What is claimed is:
1. A compound of the Formula I:

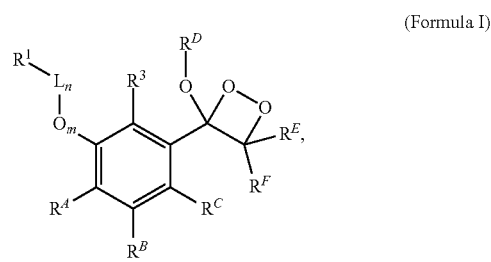

(Formula I)

wherein

R$^1$ is an analyte-responsive group selected from the group consisting of an enzyme-labile group and a boron-containing group having the formula —B(Z)(Z') or —B(Z")$_3$$^-$Kat$^+$;

Z and Z' are independently selected from the group consisting of R$^4$ and OR$^5$, wherein R$^4$ is selected from the group consisting of —OH, —O$^-$Kat$^+$, C1-C4 alkyl, C2-C4 heteroalkyl, C2-C4 alkenyl, C2-C4 heteroalkenyl, C2-C4 alkynyl, C2-C4 heteroalkynyl, C5-C6 aryl, C5-C6 heteroaryl, C6-C10 aralkyl, and C6-C10 heteroaralkyl, and R$^5$ is selected from the group consisting of —H, C1-C4 alkyl, C2-C4 heteroalkyl, C2-C4 alkenyl, C2-C4 heteroalkenyl, C2-C4 alkynyl, C2-C4 heteroalkynyl, C5-C6 aryl, C5-C6 heteroaryl, C6-C10 aralkyl, and C6-C10 heteroaralkyl, or wherein two R$^4$, two R$^5$ or one R$^4$ and one R$^5$ together with their intervening atoms form a 5- to 7-membered heterocyclic ring;

Z" is selected from the group consisting of F, Cl, Br, and I;

Kat$^+$ is an organic or inorganic cation;

L is a self-immolative linker selected from the group consisting of

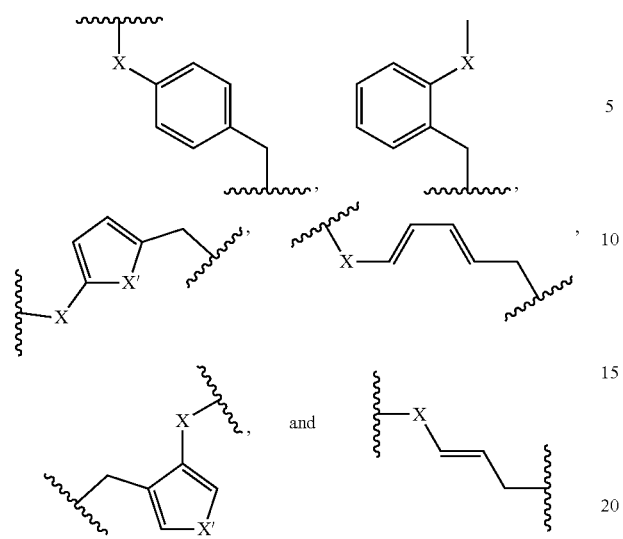

which, upon acting of an analyte on the analyte-responsive group $R^1$, is released from the remainder part of the compound of Formula I, wherein X is connected to $R^1$ and is either absent or selected from the group selected from —O—, —NH—, and $-N^+(R^G)_2$—, provided that when $R^1$ is —B(Z)(Z') or $-NO_2$, X is absent; X' is selected from the group consisting of S, O, NH, and $NR^G$; and L is optionally functionalized with a peptide, an endolysine or a protein; provided that:

when $R^1$ is an enzyme-labile group, n is 1 and m is 1 or n is 0 and m is 1;

when $R^1$ is —B(Z)(Z') or —B(Z")$_3$⁻Kat⁺, n and m are both 0 or both 1; and when $R^1$ is the enzyme-labile group

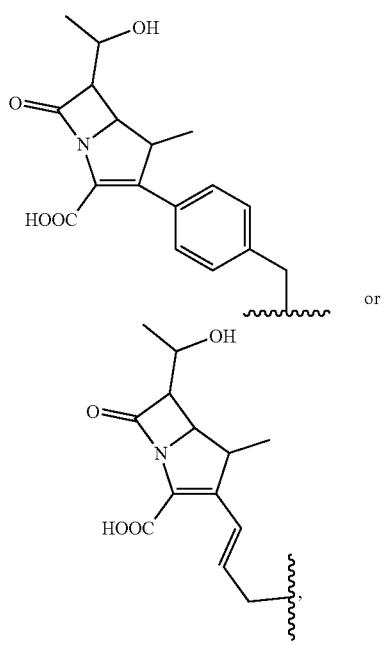

n is 0 and m is 1;
$R^A$ is H;
$R^C$ together with $R^B$ forms a 6-membered ring selected from the group consisting of $R^2$ is a group selected from the group consisting of cyano, nitro, aryl, alkenyl,

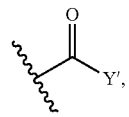

carbonyl having the structure

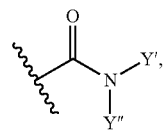

and amide having the structure wherein Y is H, a C1-C12 alkyl, or an alkali metal ion, and Y' and Y" each independently is selected from the group consisting of H and C1-C12 alkyl, or together with the nitrogen atom form a heterocyclic structure;

$R^3$ is H, F, Cl, Br, I, $CF_3$ or $R^2$-Q-;

Q is group comprising a pi-system that is conjugated with the pi-system of the central aromatic ring of the compound of Formula I;

$R^D$ is selected from the group consisting of a linear or branched C1-C18 alkyl and C3-C7 cycloalkyl;

$R^E$ and $R^F$ each independently is selected from the group consisting of a branched C3-C18 alkyl or C3-C7 cycloalkyl, or $R^E$ and $R^F$ together with the carbon atom to which they are attached form a fused, spiro or polycyclic ring; and $R^G$ each independently is selected from C1-C12 alkyl.

2. The compound according to claim 1, selected from the group consisting of:

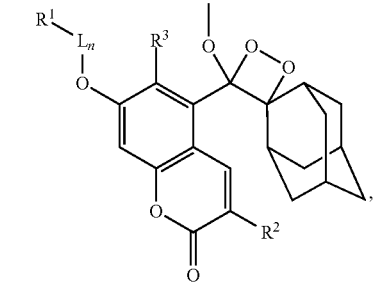

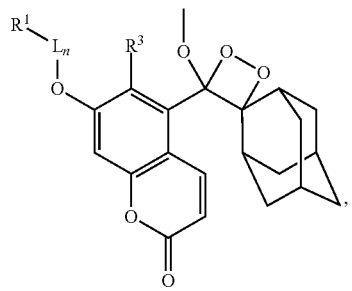

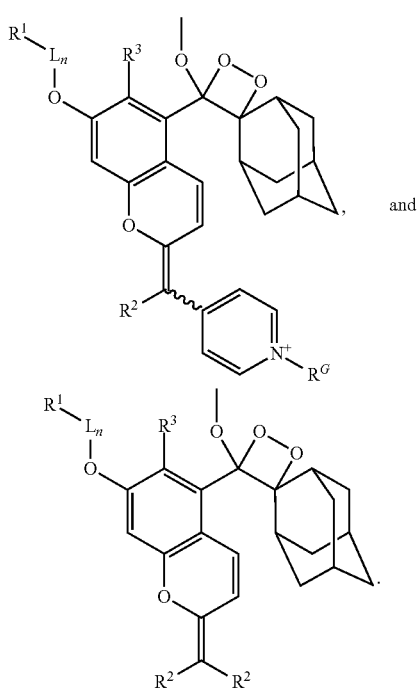

3. A method for the detection of a target analyte, a target microorganism or a target metabolite, comprising the steps of
   a) providing a medium comprising one or more target analytes, target microorganisms or target metabolites,
   b) adding a dioxetane compound to the medium so that the dioxetane compound emits light, and
   c) detecting the emitted light, wherein said dioxetane compound has the Formula I:

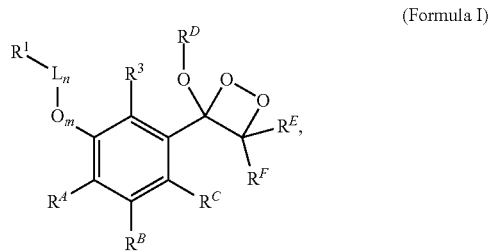

(Formula I)

wherein
R¹ is an analyte-responsive group selected from the group consisting of an enzyme-labile group and a boron-containing group having the formula —B(Z)(Z') or —B(Z")₃⁻Kat⁺;
Z and Z' are independently selected from the group consisting of R⁴ and OR⁵,
wherein R⁴ is selected from the group consisting of —OH, —O⁻Kat⁺, C1-C4 alkyl, C2-C4 heteroalkyl, C2-C4 alkenyl, C2-C4 heteroalkenyl, C2-C4 alkynyl, C2-C4 heteroalkynyl, C5-C6 aryl, C5-C6 heteroaryl, C6-C10 aralkyl, and C6-C10 heteroaralkyl,
and R⁵ is selected from the group consisting of —H, C1-C4 alkyl, C2-C4 heteroalkyl, C2-C4 alkenyl, C2-C4 heteroalkenyl, C2-C4 alkynyl, C2-C4 heteroalkynyl, C5-C6 aryl, C5-C6 heteroaryl, C6-C10 aralkyl, and C6-C10 heteroaralkyl, or
wherein two R⁴, two R⁵ or one R⁴ and one R⁵ together with their intervening atoms form a 5- to 7-membered heterocyclic ring;
Z" is selected from the group consisting of F, Cl, Br, and I;
Kat⁺ is an organic or inorganic cation;
L is a self-immolative linker selected from the group consisting of

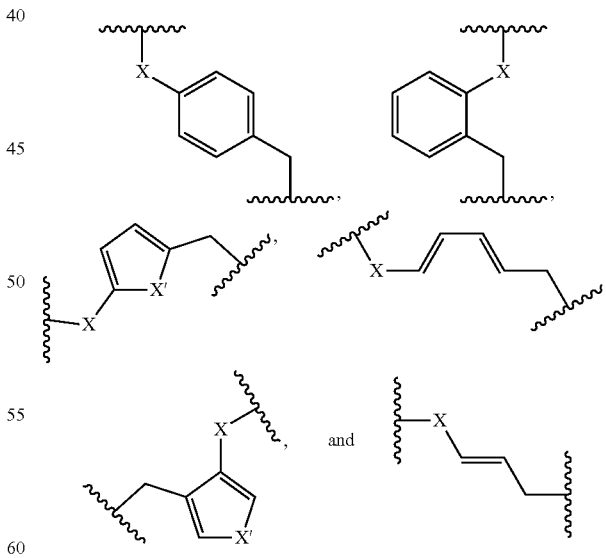

which, upon acting of an analyte on the analyte-responsive group R¹, is released from the remainder part of the compound of Formula I, wherein X is connected to R¹ and is either absent or selected from the group selected from —O—, —NH—, and —N⁺(R^G)₂—, provided that when R¹ is —B(Z)(Z') or —NO₂, X is absent; X' is selected from the group consisting of S, O, NH, and NR$^G$; and L is optionally functionalized with a peptide, an endolysine or a protein;

provided that:

when R$^1$ is an enzyme-labile group, n is 1 and m is 1 or n is 0 and m is 1;

when R$^1$ is —B(Z)(Z') or —B(Z")$_3$⁻Kat⁺, n and m are both 0 or both 1; and when R$^1$ is the enzyme-labile group

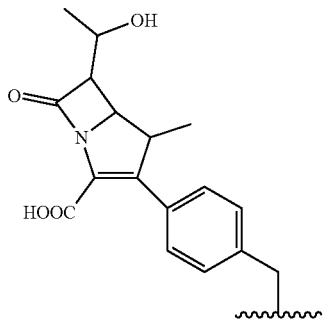

or

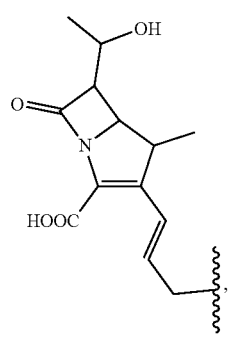

n is 0 and m is 1;

R$^A$ is H;

R$^C$ together with R$^B$ forms a 6-membered ring selected from the group consisting of

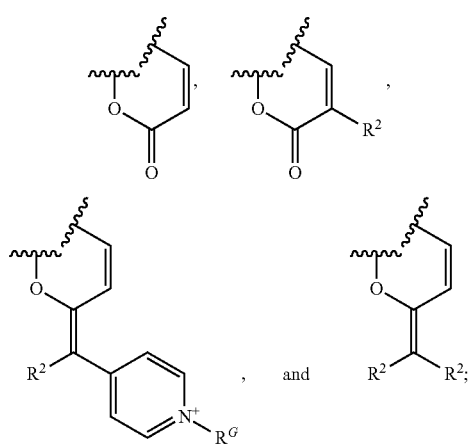

R$^2$ is a group selected from the group consisting of cyano, nitro, aryl, alkenyl,

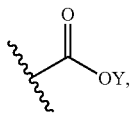

carbonyl having the structure

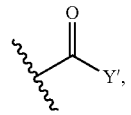

and amide having the structure

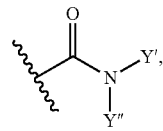

wherein Y is H, a C1-C12 alkyl, or an alkali metal ion, and Y' and Y" each independently is selected from the group consisting of H, and C1-C12 alkyl or together with the nitrogen atom form a heterocyclic structure;

R$^3$ is H, F, Cl, Br, I, CF$_3$ or R$^2$-Q-;

Q is group comprising a pi-system that is conjugated with the pi-system of the central aromatic ring of the compound of Formula I;

R$^D$ is selected from the group consisting of a linear or branched C1-C18 alkyl and C3-C7 cycloalkyl;

R$^E$ and R$^F$ each independently is selected from the group consisting of a branched C3-C18 alkyl or C3-C7 cycloalkyl, or R$^E$ and R$^F$ together with the carbon atom to which they are attached form a fused, spiro or polycyclic ring; and R$^G$ each independently is selected from C1-C12 alkyl.

4. The method according to claim 3, wherein the method is for the detection of a target microorganism.

5. The method according to claim 3, wherein
(i) the method is for the detection of growth substrates, nutrients, and/or metabolites by enzymatic oxidation of said growth substrates, nutrients, and metabolites, the method comprising the steps of:
 a) providing a medium comprising a growth substrate, nutrient, and/or metabolite capable of being oxidized by an enzyme,
 b) (b1) adding an enzyme capable of oxidizing the growth substrate, nutrient, and/or metabolite and thereby producing hydrogen peroxide,
  (b2) adding said compound of the Formula I, wherein R$^1$ is —B(Z)(Z') or —B(Z")$_3$⁻Kat⁺, to the medium so that the compound of Formula I emits light upon contact with hydrogen peroxide, wherein steps (b1) and (b2) may be performed simultaneously or subsequently, and
 c) detecting the emitted light; or
(ii) the method is for the detection of bacterial endotoxins via detection of limulus factor C, in which said compound of the Formula I, wherein R$^1$ is Boc-Val-Pro- Argininyl or Boc-Asp(OBzl)-Pro-Argininyl, and limulus factor C are added to an endotoxin-comprising medium, and the emitted light is detected; or (iii) the method is for testing pasteurization of dairy products the method comprising the steps of:
  a) providing a dairy product medium,
  b) pasteurization of said dairy product medium,
  c) adding said compound of the Formula I, wherein $R^1$ is phosphoryl, to the medium, optionally in combination with a buffer, so that the compound emits light, and
  d) detecting the emitted light; or (iv) the method is for testing of an antibiotic resistance in microorganisms, the method comprising the steps of:
  a) providing a medium comprising one or more microorganisms,
  b) adding said compound of the Formula I, wherein $R^1$ is a beta-lactamase-labile group to the medium so that the compound emits light when antibiotic resistant microorganisms are present in the medium, and
  c) detecting the emitted light; or (v) the method is for detecting inorganic phosphate, the method comprising the steps of:
  a) providing a medium comprising inorganic phosphate,
  b) adding said compound of the Formula I, wherein $R^1$ is oxalylester, to the medium so that the compound emits light, and
  c) detecting the emitted light; or (vi) the method is for monitoring of a sterilization process, the method comprising the steps of:
  a) a1) providing a medium comprising a microorganism that produces alpha-glucosidase,
     a2) sterilizing the medium,
  b) adding said compound of the Formula I, wherein $R^1$ is alpha-D-glucopyranosidyl, to the medium, and
  c) detecting the emitted light;

(vii) the method is for detection of antibiotic resistance of bacteria and for antibiotic susceptibility testing, the method comprising the steps of:
  a) providing a medium comprising said bacteria,
  b) adding an antibiotic,
  c) adding said compound of the Formula I, wherein $R^1$ is an enzyme-labile group that is either removable or modified by an enzyme of said bacteria such that luminescence of said compound is triggered, wherein step c) may be performed before, together with, or after step b),
  d) detecting the emitted light, if any.

6. The method according to claim 3, wherein $R^1$ and the respective target analyte, target microorganism or target metabolite are defined as shown in the following table:

| $R^1$ | Target analyte/target microorganism/target metabolite |
|---|---|
| acetyl | a microorganism |
| butyryl | a microorganism |
| octanoyl | Salmonella |
| nonanoyl | Salmonella |
| myo-inositol phosphoryl | Listeria monocytogenes; Bacillus; Staphylococcus; Clostridium; Mycobacterium tuberculosis |
| phosphoryl | Staphylococcus aureus; Clostridium perfringens; S. agalactiae; Candida spp.; MRSA |
| L-alaninyl | Gram-negative bacteria; Yeast and molds |
| L-leucinyl | Yeast and molds |
| B-alanyl | Pseudomonas aeruginosa |
| L-pyroglutamic acidyl | Enterococci; Streptococcus pyogenes; Citrobacter |
| beta-D-galactopyranosidyl | Coliform; E. coli |
| alpha-D-galactopyranosidyl | Salmonella |
| alpha-D-glucopyranosidyl | Cronobacter sakazakii; Staphylococcus aureus; MRSA; VRE; Geobacillus stearothermophilus |
| beta-D-glucopyranosidyl | i spp ESBL producing enterobacteria Vibrio Enterococci VRE Candida spp. Clostridium difficile |
| beta-D-glucuronyl | E. coli; Streptococcus agalactiae |
| beta-D-glucuronyl sodium salt | E. coli; Streptococcus agalactiae |
| n-acetyl-beta-D-galactosaminidyl | Candida albicans |
| N-acetylneuraminidyl | Prevotella |
| cellobio sidy 1 | Cronobacter sakazakii |
| ribofuranosidyl | Shigella |
| choline phosphoryl | Bacillus |
| -B(Z)(Z'), | 1) $H_2O_2$ released by a variety of microbial oxidases |
| -B(Z")$_3^-$Kat$^+$ | 2) $H_2O_2$ released by an oxidase reacting on a microbial metabolite/substrate |
| -$NO_2$ | a microorganism |
| oxalylester | Apyrase |
| Boc-Val-Pro-Argininyl | Bacterial Endotoxines |
| Boc-Asp(OBzl)-Pro-Argininyl | Bacterial Endotoxines |
| SucOMe-Arg-Pro-Tyrosinyl | Legionella pneumophila |
| A beta-lactamase-labile group, penicillin, a cephalosporin of | Antibiotic resistant microorganisms |
| Ac-QLQ- | |
| Ac-FQLQ- | |
| Ac-EFQLQ- | |
| Ac-DEFQLQ- | a norovirus |
| Amides of 5-substituted-o-antranilic acid methyl ester | Campylobacter jejuni |
| Acrylic acid ester | Cysteine. |

7. The method according to claim 3, wherein said dioxetane compound is selected from the group consisting of:

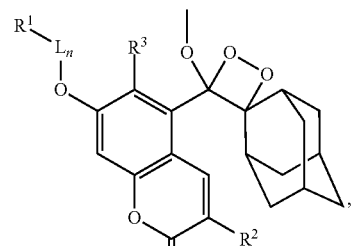

,

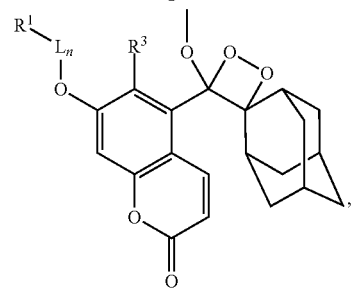

,

-continued

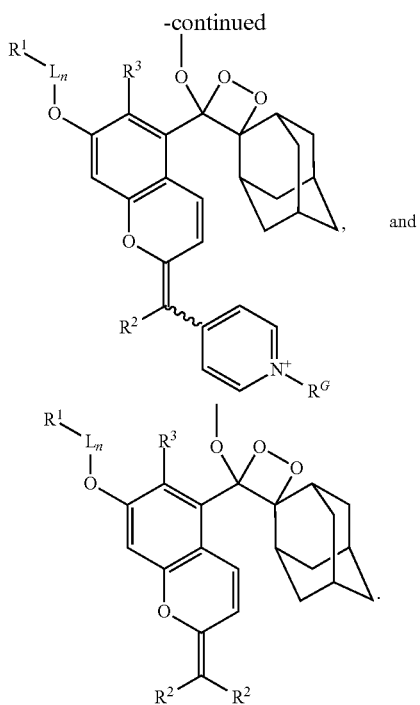

8. The method according to claim 4, wherein said target microorganism is selected from a bacteria, yeast, mold, and virus.

9. The method according to claim 8, wherein said bacteria is selected from the group consisting of a *Salmonella*; *Listeria*; *Staphylococcus*; *E. coli*; carbapenem-resistant bacteria; *Campylobacter*; *Bacillus*; *Clostridium*; *Mycobacterium*; *Streptococcus*; *Pseudomonas*; *Enterococcus*; *Citrobacter*; *Coliform*; *Cronobacter sakazakii*; *Geobacillus stearothermophilus*; *Vibrio*; *Legionella pneumophilia*; apyrase-containing bacterium; extended-spectrum beta-lactamase (ESBL)-producing enterobacterium; and *Prevotella*; said yeast is a *Candida*; and said virus is a virus of the Caliciviridae family.

10. The method of claim 9, wherein said *Salmonella* is *S. enterica*; said *Listeria* is *L. monocytogenes*; said *Staphylococcus* is *S. aureus* or a methicillin-resistant *Staphylococcus aureus* (MRSA); said carbapenem-resistant bacteria is *Pseudomonas aeruginosa* or *Klebsiella pneumonia*; said *Campylobacter* is *C. jejuni*, *C. coli*, or *C. lari*; said *Clostridium* is *C. perfringens* or *C. difficile*; said *Mycobacterium* is *M. tuberculosis*; said *Streptococcus* is *S. agalactiae* or *S. pyogenes*; said *Pseudomonas* is *P. aeruginosa*; said *Enterococcus* is vancomycin-resistant *Enterococcus* (VRE); said apyrase-containing bacterium is *Shigella*; said *Candida* is *Candida albicans*; said virus of the Caliciviridae family is a Lagovirus, Norovirus, Sapovirus, Nebovirus, or Recovirus.

11. The compound according to claim 1, wherein L is

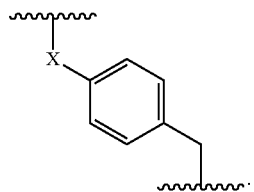

12. The method according to claim 3, wherein L is

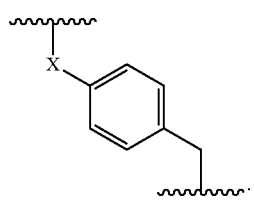

13. The compound according to claim 1, wherein X is —O— or —N⁺(CH₃)₂—.

14. The method according to claim 3, wherein X is —O— or —N⁺(CH₃)₂—.

15. The method of claim 6, wherein:
(i) $R^1$ is acetyl, and said microorganism is *Campylobacter jejuni*, *C. coli* or *C. lari*;
(ii) $R^1$ is butyryl, and said microorganism is *Moraxella catarrhalis*; or
(iii) $R^1$ is a beta-lactamase-labile group, and said beta-lactamase-labile group is a beta-lactam antibiotic.

16. The method of claim 15, wherein said beta-lactam antibiotic is a penicillin, a cephalosporin of generation 1 to 5, a cephamycin, or a carbapenem.

* * * * *